(12) United States Patent
Okada et al.

(10) Patent No.: US 7,780,659 B2
(45) Date of Patent: *Aug. 24, 2010

(54) ULTRASOUND TREATMENT SYSTEM

(75) Inventors: Mitsumasa Okada, Hachioji (JP); Toshiya Sugai, Hachioji (JP); Yoshitaka Honda, Tokorozawa (JP); Manabu Ishikawa, Hachioji (JP); Tomohisa Sakurai, Sagamihara (JP)

(73) Assignee: Olympus Corporation, Tokyo (JP)

( * ) Notice: Subject to any disclaimer, the term of this patent is extended or adjusted under 35 U.S.C. 154(b) by 148 days.

This patent is subject to a terminal disclaimer.

(21) Appl. No.: 10/650,759

(22) Filed: Aug. 29, 2003

(65) Prior Publication Data

US 2005/0004589 A1  Jan. 6, 2005

Related U.S. Application Data

(60) Division of application No. 09/353,652, filed on Jul. 15, 1999, now Pat. No. 6,669,690, which is a continuation-in-part of application No. 09/345,794, filed on Jul. 1, 1999, now abandoned, which is a division of application No. 08/938,523, filed on Sep. 26, 1997, now Pat. No. 6,056,735, which is a continuation-in-part of application No. 08/627,500, filed on Apr. 4, 1996, now abandoned.

(30) Foreign Application Priority Data

| Apr. 6, 1995 | (JP) | ................................. H7-081466 |
| May 11, 1995 | (JP) | ................................. H7-113410 |
| Jul. 28, 1995 | (JP) | ................................. H7-193250 |
| Jul. 31, 1995 | (JP) | ................................. H7-195155 |
| Jul. 31, 1995 | (JP) | ................................. H7-195156 |
| Oct. 6, 1995 | (JP) | ................................. H7-259990 |
| Nov. 10, 1995 | (JP) | ................................. H7-292938 |
| Jul. 16, 1998 | (JP) | ................................. H10-201965 |

(51) Int. Cl.
*A61B 18/18* (2006.01)

(52) U.S. Cl. .............................. 606/40; 623/49; 623/51; 623/52; 623/169

(58) Field of Classification Search .................. 606/40, 606/49, 51, 52, 166, 169, 170, 171, 1, 2; 604/22, 48

See application file for complete search history.

(56) References Cited

U.S. PATENT DOCUMENTS 2,002,594 A * 5/1935 Wappler et al. ............... 606/46

(Continued)

FOREIGN PATENT DOCUMENTS

EP  0830845 A  3/1998

*Primary Examiner*—Paul Prebilic
(74) *Attorney, Agent, or Firm*—Kratz, Quintos & Hanson, LLP

(57) ABSTRACT

An ultrasound treatment system in accordance with the present invention comprises an ultrasonic transducer, a handpiece, a probe, a sheath, a clamping member, an operation unit, an operating member, a suction base, and a perfusion base. The ultrasonic transducer generates ultrasonic vibrations. The handpiece has the ultrasonic transducer incorporated therein and serves as an operation unit. The probe is connected to the ultrasonic transducer, and serves as a vibration transmitting member for transmitting ultrasonic vibrations to a distal member realizing a stationary portion that is a treatment portion for treating a living tissue. The sheath serves as a protecting member for shielding the probe. The clamping member is opposed to the distal member at the distal end of the sheath, and realizes a movable portion that is another treatment portion for clamping a living tissue in cooperation with the distal member. The operation unit is manipulated for clamping a living tissue with the clamping member and distal member or freeing the living tissue therefrom.

17 Claims, 58 Drawing Sheets

U.S. PATENT DOCUMENTS

| | | | |
|---|---|---|---|
| 3,589,363 A * | 6/1971 | Banko et al. | 604/22 |
| 3,645,255 A * | 2/1972 | Robinson | 601/2 |
| 3,862,630 A | 1/1975 | Balamuth | |
| 4,989,588 A | 2/1991 | Kubota et al. | |
| 5,176,677 A | 1/1993 | Wuchinich | |
| 5,217,460 A * | 6/1993 | Knoepfler | 606/52 |
| 5,322,055 A * | 6/1994 | Davison et al. | 601/2 |
| 5,334,183 A | 8/1994 | Wuchinich | |
| 5,456,689 A | 10/1995 | Kresch et al. | |
| 5,606,974 A * | 3/1997 | Castellano et al. | 600/462 |
| 5,797,939 A | 8/1998 | Yoon | |
| 5,800,448 A | 9/1998 | Banko | 606/169 |
| 5,836,897 A | 11/1998 | Sakurai et al. | |
| 5,893,835 A | 4/1999 | Witt et al. | 601/2 |
| 5,984,939 A | 11/1999 | Yoon | 606/139 |
| 6,024,750 A * | 2/2000 | Mastri et al. | 606/169 |
| 6,036,667 A * | 3/2000 | Manna et al. | 604/22 |
| 6,056,735 A * | 5/2000 | Okada et al. | 606/1 |
| 6,083,223 A | 7/2000 | Baker | |
| 6,129,735 A * | 10/2000 | Okada et al. | 606/169 |
| 6,340,352 B1 | 1/2002 | Okada et al. | 604/22 |
| 6,454,781 B1 * | 9/2002 | Witt et al. | 606/169 |
| 6,669,690 B1 * | 12/2003 | Okada et al. | 606/40 |
| 6,682,544 B2 * | 1/2004 | Mastri et al. | 606/169 |
| 6,790,216 B1 * | 9/2004 | Ishikawa | 606/169 |
| 6,887,252 B1 * | 5/2005 | Okada et al. | 606/169 |

* cited by examiner

FIG.6
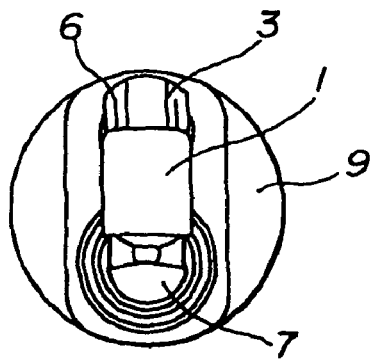
FIG.7A    FIG.7B    FIG.7C
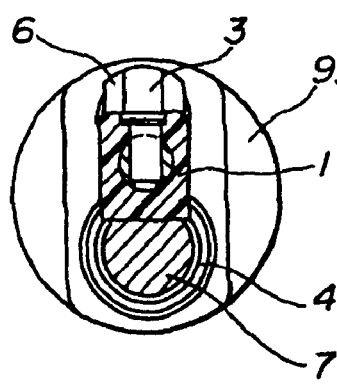 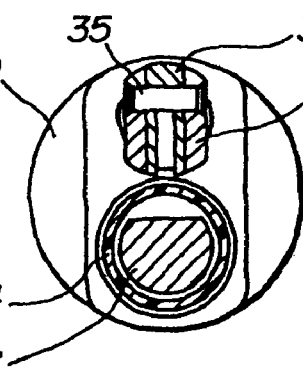 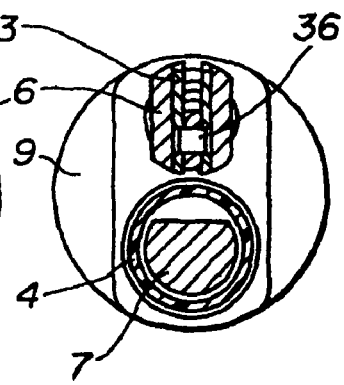
FIG.7D    FIG.7E    FIG.7F
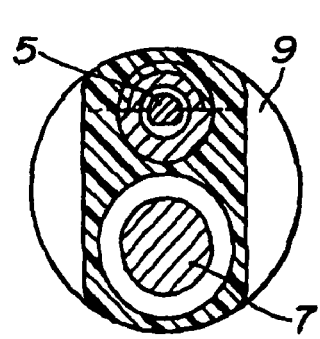 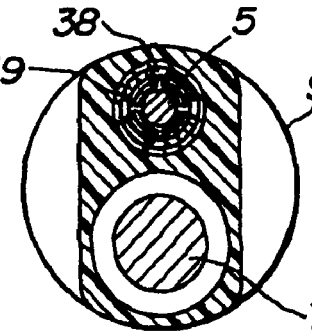 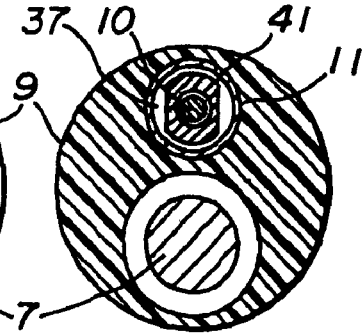

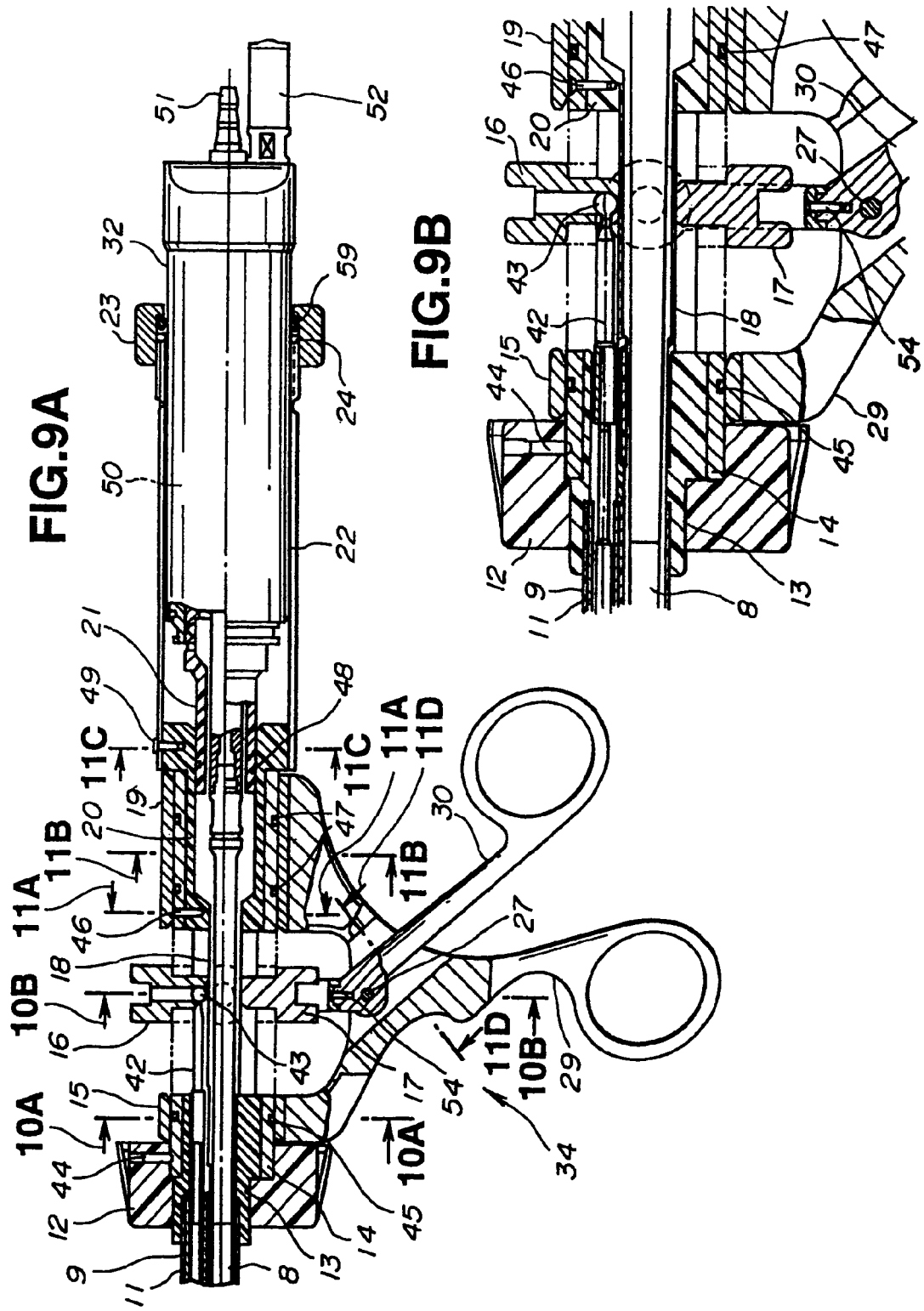

FIG.12B FIG.12A
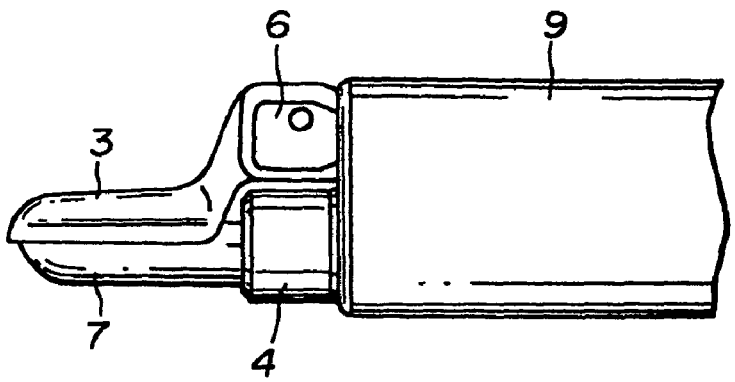
FIG.13A
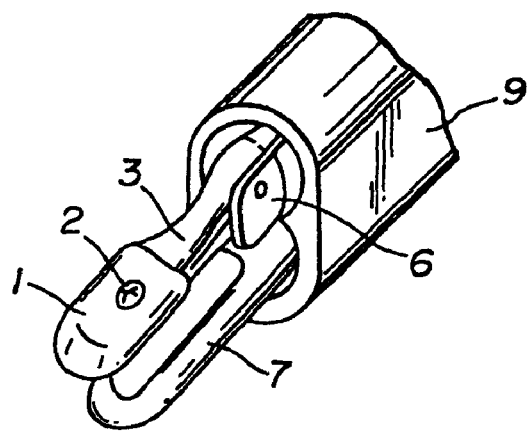
FIG.13B
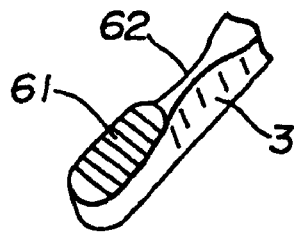

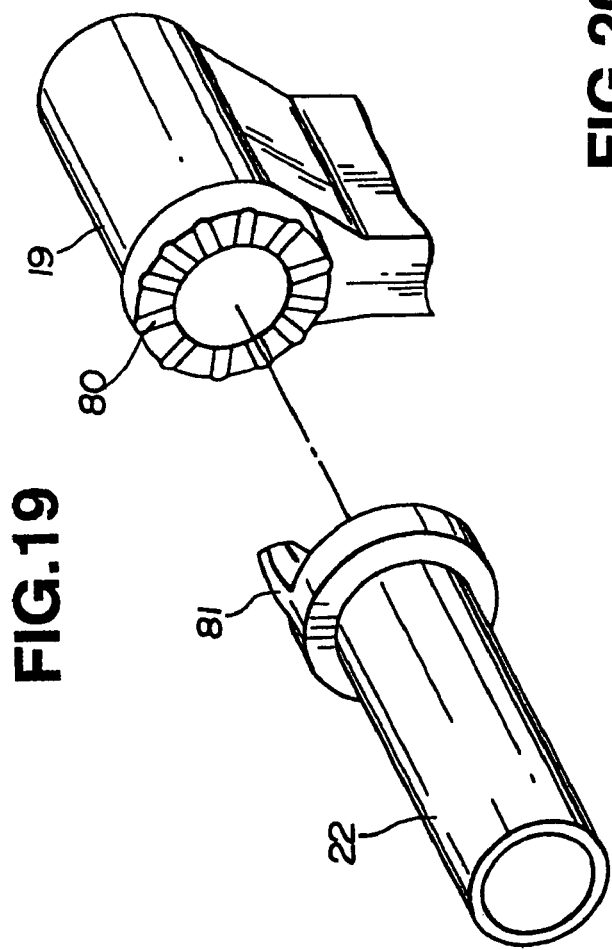
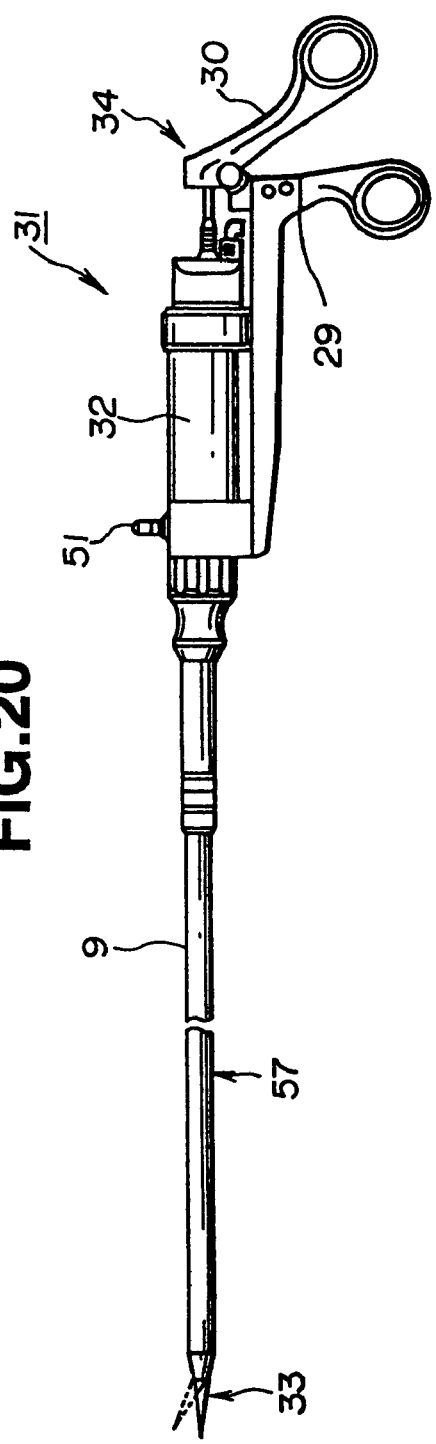
FIG.19
FIG.20

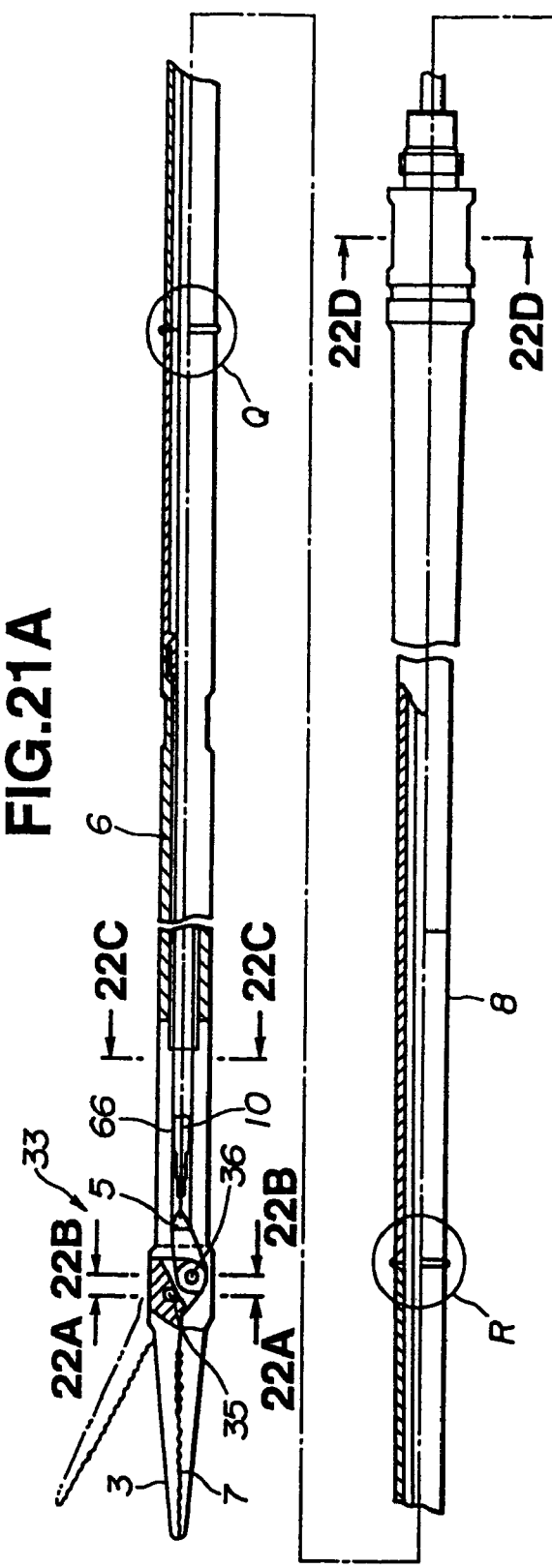
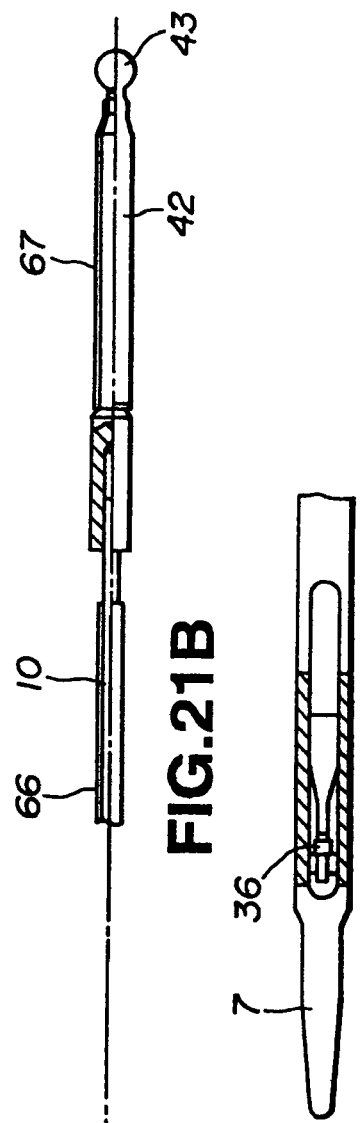
FIG.21A
FIG.21B

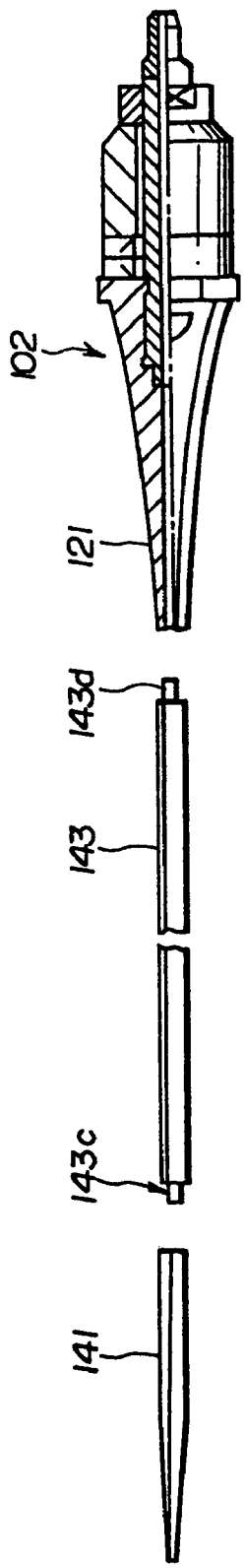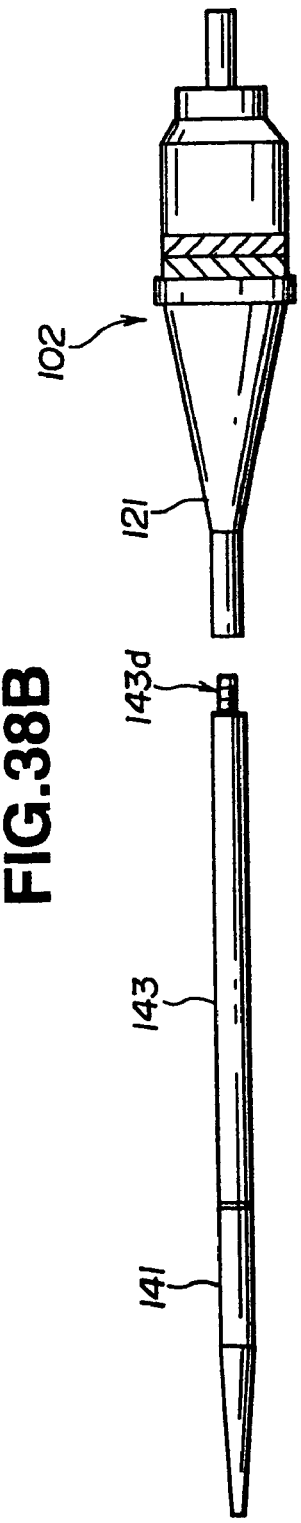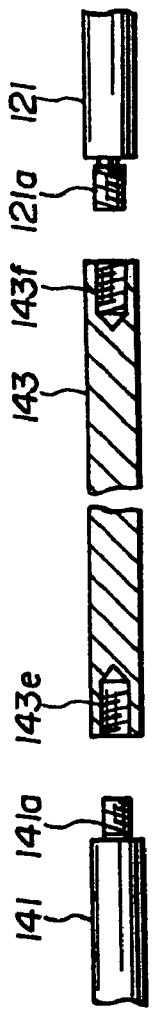
FIG.38A
FIG.38B
FIG.38C

FIG.82
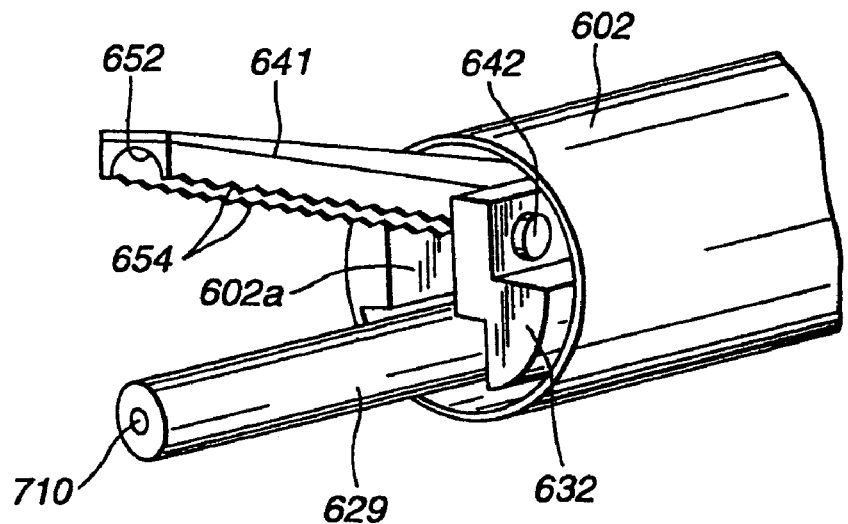
FIG.83A
FIG.83B
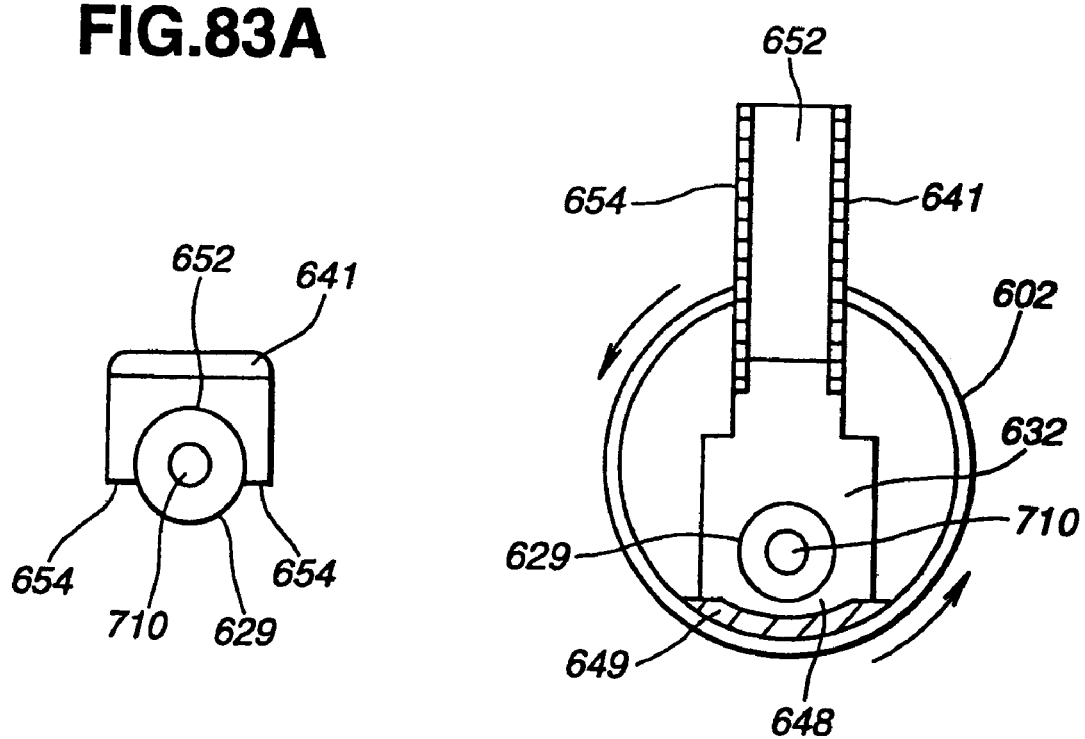

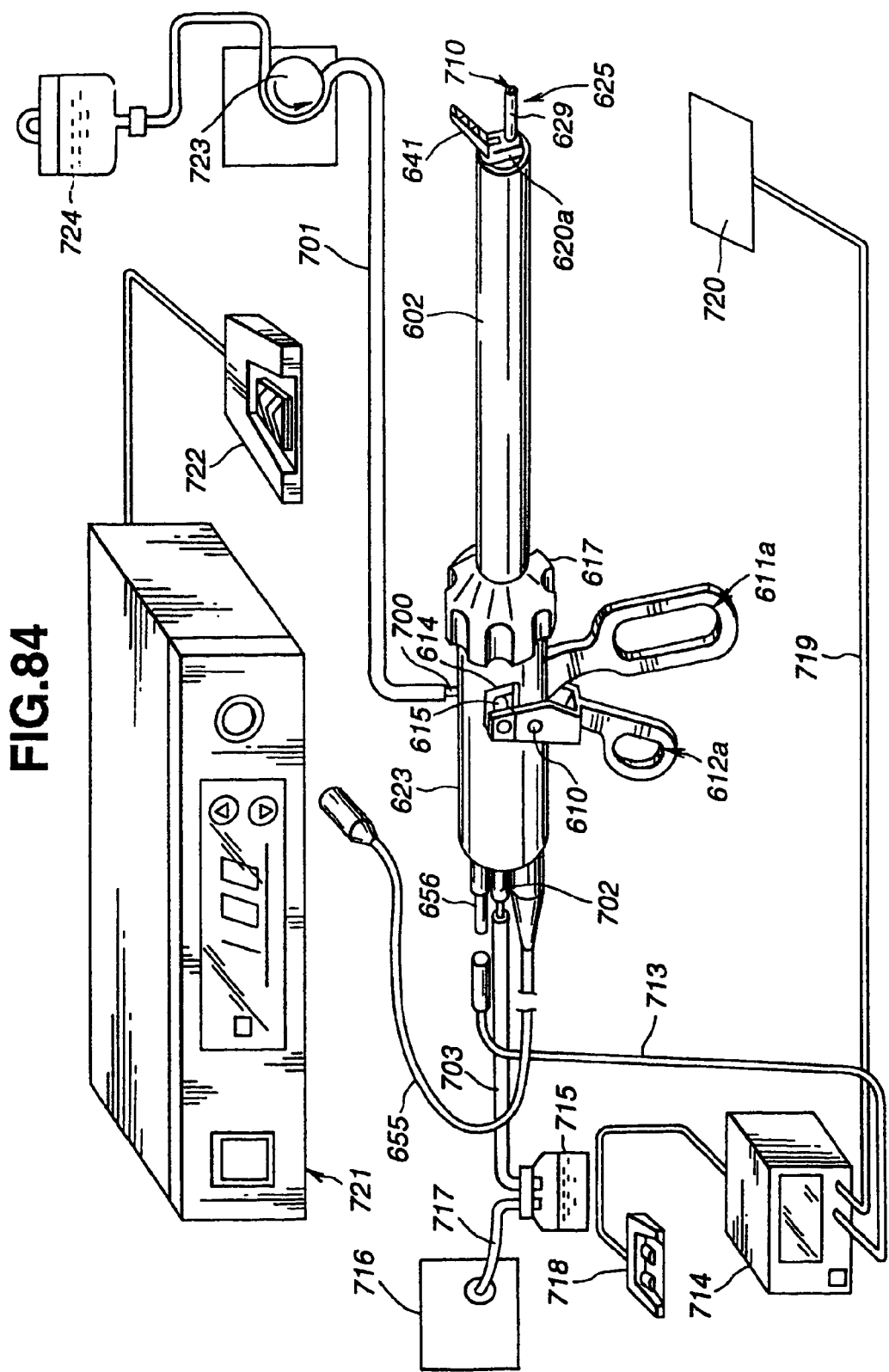

ULTRASOUND TREATMENT SYSTEM

This is a Divisional of U.S. Ser. No. 09/353,652 filed Jul. 15, 1999, now U.S. Pat. No. 6,669,690, which is a Continuation-In-Part of U.S. Ser. No. 09/345,794 filed Jul. 1, 1999, now abandoned, which is a Divisional of U.S. Ser. No. 08/938,523 filed Sep. 26, 1997, now U.S. Pat. No. 6,056,735, which is in turn a Continuation-In-Part application of U.S. Ser. No. 08/627,500 filed Apr. 4, 1996, now abandoned.

BACKGROUND OF THE INVENTION

1. Field of the Invention

The present invention relates to an ultrasound treatment system for coagulating or resecting the region of a living tissue to be treated.

2. Description of the Related Art

In recent years, it has become a matter of common practice that an endoscope is inserted in a body cavity in order not only to observe an organ in the body cavity but also to conduct various kinds of curative procedures and treatments under the observation through the endoscope.

A means for conducting a curative treatment under endoscopic observation includes an ultrasound aspiration system that utilizes ultrasonic vibrations for aspiration and an ultrasound knife system that utilizes ultrasonic vibrations for incision or the like. Moreover, there is a cautery knife system that applies a high-frequency signal to a living tissue through the tip of a probe for the purpose of incision or the like.

For example, Japanese Patent Laid-Open No. 62-127042 describes that a stone is clamped and crushed by means of ultrasonic vibrations. Japanese Patent Laid-Open 1-232944 describes that a living tissue is clamped and immobilized using clamp forceps and incised by a probe making ultrasonic vibrations. Japanese Patent Laid-Open No. 1-232945 describes that a living tissue is sucked for immobilization and then incised by a knife making ultrasonic vibrations.

Furthermore, Japanese Patent Laid-Open No. 1-232948 describes that ultrasonic vibrations are imposed on cutting forceps for efficient resection of a living tissue. Japanese Patent Laid-Open No. 1-232949 describes similarly to the Japanese Patent Laid-Open No. 1-232944 that a living tissue is immobilized using a clamping means and then treated by means of a treatment member on which ultrasonic vibrations are imposed. U.S. Pat. No. 5,322,055 has proposed an ultrasound surgical appliance shown in FIG. 1. The ultrasound surgical appliance has a holding member 991 attached to the tip of a sheath 990 at a point. A bar 992 lying through the sheath 990 is used to cause the holding member 991 to pivot. An ultrasound probe 993 is inserted in the sheath 990 so that the ultrasound probe 993 can turn about an axis. The ultrasound probe 993 has a knife-like incision area 994 formed on one side of the distal portion thereof, and has a substantially round coagulation surface 995 formed on the other side thereof. When the ultrasound probe 993 is turned by manipulating the appliance at a proximal position of the appliance, the incision area 994 or coagulation surface 995 is selected. Thus, the appliance has a composite structure.

To be more specific, for ultrasonic coagulation of a living tissue, as shown in FIG. 1, setting is such that the coagulation surface 995 is oriented toward the holding member 991. The living tissue is clamped by the holding member 991 and coagulation surface 995 and then subjected to ultrasonic coagulation. By contrast, for incising a living tissue, setting is such that the incision area 994 is oriented toward the holding member 991. The living tissue is clamped by the holding member 991 and incision area 994 and subjected to ultrasonic incision. Thus, one ultrasound surgical appliance is used to conduct ultrasonic coagulation and ultrasonic incision selectively.

In the ultrasound surgical appliance, one side of the distal portion of the ultrasound probe 993 exposed from the tip of the sheath 990 is the coagulation surface 995 having a substantially circular and blunt contour. The opposite side thereof includes the incision area 994 having a sharp contour suitable for incision. As shown in FIG. 1, during coagulation, in particular, since the sharp blade section is oriented in a direction opposite to an object tissue or is facing outward opposite to the holding member 991, there is a possibility that not only a burn but also an injury of a tissue by the blade section may occur. For avoiding these incidents, time-consuming and annoying check work is needed. This becomes one of causes deteriorating maneuverability.

Moreover, in the ultrasound surgical appliance, the clamp unit and surgical blade are used to clamp a tissue. This poses problems that a clamped area is limited and sufficient force is not applied to a region to be cut out.

In particular, for example, as far as a ligament containing lots of fibers is concerned, there is a problem that the ligament cannot be cut off reliably, or a problem that since it takes much time to perfectly cut off the ligament, a surgical blade may dissipate heat very much to burn any other living tissue in contact with the surgical blade.

As far as existing treatment appliances used for a surgical procedure under endoscopic observation are concerned, a treatment unit used to treat a living tissue is usually located at the distal end of a sheath that is an insertion unit for inserting the treatment unit into a living body, and a manipulating means for use in manipulating the treatment unit is located at the proximal end of the insertion unit.

In these treatment appliances for surgery under endoscopic observation, a structure, in which as described in DE G92 14059.9 or U.S. Pat. No. 5,290,308, an insertion unit and a treatment unit can be turned relative to a manipulating means, is well-known. According to Japanese Patent Laid-Open No. 6-167728 or DE G91 14 306.3, a frictional means is used to adjust a torque. Japanese Examined Patent Publication No. 5-86223 describes that a ball click is used to fix an angle of a turn.

As mentioned above, when an ultrasound treatment appliance is used to clamp a living tissue, it is essential to isolate a probe from a sheath or the like in terms of vibrations because of the presence of a transducer unit. Since there is a structural restriction that the probe cannot be turned because the center axis of the probe does not align with the center axis of a conveying means, an ultrasound treatment appliance in which a treatment unit can be turned freely relative to a manipulating means is unavailable. Depending on the situation of a living tissue, a hand handling a manipulating means may be obliged to be twisted or to handle the manipulating means in any other unnatural manner. Thus, the ultrasound treatment appliance still has drawbacks that must be overcome for practical use.

For resolving these drawbacks, making better approaches to a living tissue, and improving maneuverability, Japanese Examined Utility Model Publication No. 6-6809 has revealed that an insertion unit of an ultrasound treatment appliance is curved. However, in this appliance, since a handpiece serving as a manipulating means is circular and devoid of directivity, good maneuverability is ensured. In an ultrasound treatment appliance having a directive handle as a manipulating means, the aforesaid problems cannot be solved completely.

Furthermore, when an ultrasound treatment appliance is cleaned and sterilized, each component must be cleaned and sterilized with the greatest care. This work is quite laborious and cumbersome. For omitting the labor, the appliance may be designed to be disposable. However, there is a problem, which must be solved, concerning the reduction of medical expenses, diminishment of polluted wastes, and saving of resources. If any one part should be broken, the whole appliance would have to be repaired or replaced with a new one.

Furthermore, for example, the first related art described in Japanese Patent Laid-Open No. 60-80446 is an ultrasound surgical system that has the capability of a cautery knife so as to crush a living tissue using ultrasonic waves, and that feeds a high-frequency current to a horn at a distal end so as to arrest bleeding through part of a vessel. By handling switches, ultrasonic waves can be supplied or a high-frequency current can be fed.

Moreover, for example, the second related art described in Japanese Patent Laid-Open No. 60-227748 is a disclosure of an appliance that is a combination of the capability of an ultrasound knife with that of a cautery knife.

In this second related art, an effort is made to wield the outputs of the ultrasound and cautery knives simultaneously.

However, the appliance becomes large in size and expensive. The cautery knife has the hazard of a leakage current. It must be avoided that the hazard is intensified by combining the cautery knife with the ultrasound knife. Moreover, since the cautery knife and ultrasound knife are different from each other in terms of medical functions and advantages, they may not sometimes be acted simultaneously.

Additionally, the ultrasonic coagulation/incision system disclosed in the U.S. Pat. No. 5,322,055 oscillates with a living tissue clamped using the distal part of the probe and the clamping member. Resultant ultrasonic vibrations are transmitted to the probe, whereby a living tissue is coagulated or incised. If a large amount of blood or a fatty tissue is present in a surgical region, the blood or fatty tissue may be sucked into the sheath shielding the probe.

A driving mechanism for driving the clamping member is incorporated in the sheath of the ultrasonic coagulation/incision system. When compared with an ultrasonic suction apparatus having a very simple intra-sheath structure, the intra-sheath structure of the ultrasonic coagulation/incision system is very complex. Once blood or a fatty tissue sucked into the sheath adheres to the inside of the probe, it is very hard to remove the blood or fatty tissue.

When blood or a fatty tissue adheres to the inside of the probe, the impedance of the probe rises outstandingly. Consequently, the ultrasonic coagulation/incision system fails to ultrasonically oscillate. Specifically, the impedance characteristic of the probe is disordered, and the resonant frequency of a resonant circuit becomes uncertain. This poses a problem in that the ultrasonic coagulation/incision system cannot ultrasonically oscillate any longer.

In this type of ultrasonic coagulation/incision system, a living tissue to be coagulated and resected is clamped by the distal part of the probe and the clamping member. When the living tissue is clamped and immobilized, energy of ultrasonic vibrations is converted into frictional heat. The living tissue is gradually coagulated and then resected.

At this time, the frictional heat should merely be transmitted to a clamped portion of the living tissue. In practice, however, the frictional heat is dispersed over a plane on which the living tissue is clamped. There is a fear that a living tissue other than the intended living tissue may be affected by the heat.

For example, a nervous tissue is a region in which a problem may stem from transmission of heat. It is a matter of common practice that when treatment is conducted using the foregoing ultrasonic treatment appliance near the nervous tissue, the ultrasonic treatment appliance is separated by at least a certain distance from the region.

However, a region that must not be affected by heat may be sunk in a fatty tissue or hidden behind a treatment portion. In this case, the region may not be able to be observed. Furthermore, if a region susceptible to heat and the treatment portion are located mutually closely, ultrasonic treatment cannot be conducted. This poses a problem in that usable ultrasonic treatment appliances are limited.

Another problem will be described below. When the probe of the ultrasonic coagulation/incision system is vibrated ultrasonically, it may oscillate at a frequency other than predetermined frequencies (referred to as transverse vibration). In this case, an unbearable abnormal sound may be heard. Furthermore, in this mode, energy causing longitudinal vibration that is a normal oscillation form is converted into energy causing transverse vibration. This leads to a reduction in vibrational energy to be applied to the distal end of the probe. Eventually, deterioration in the functions of coagulation and incision is invited.

Furthermore, when the ultrasonic coagulation/incision system is used, mist is generated from the distal part thereof for clamping a living tissue and coagulating and for resecting it with ultrasonic vibrations. The mist clouds the interior of a body cavity during a surgical procedure under endoscopic observation. This hinders observation of a surgical field. Moreover, the endoscope itself is clouded. This poses a serious problem.

Furthermore, when the ultrasonic coagulation/incision system is used, as long as a blood vessel to be treated or an organ is exposed to the surface, no problem occurs. However, the organ may be sunk in a fatty tissue or the like, the organ may adhere to another region, or the treatment portion may be hidden behind a liquid such as blood. In this case, the region to be treated must be peeled and exposed beforehand. Various forceps or the like may therefore be used. An ultrasonic suction apparatus may be used to perform suction or any other treatment by taking a sufficiently long time. After the region to be treated is peeled and exposed, the ultrasonic coagulation/incision system is used to carry out the work of coagulation and hemostasis. However, especially in the field of surgery to be conducted under endoscopic observation, the work coagulation and hemostasis brings about the necessity of putting or removing a plurality of tools using a trocar and cannula. Otherwise, a plurality of operators must work in cooperation with one another. This is time-consuming. Since the work cannot be carried on continuously, a long time is required for a surgery. Besides, a patient load is enormous.

SUMMARY OF THE INVENTION

Briefly, an ultrasound treatment system of the present invention comprises: ultrasonic transducers for generating ultrasonic vibrations; a handpiece having the ultrasonic transducers therein and serving as an operation unit; a probe connected to the ultrasonic transducers and serving as a vibration conveying member for conveying ultrasonic vibrations to a distal member constituting a stationary section of a treatment unit used to treat a living tissue; a sheath serving as a protective member for covering the probe; a holding member opposed to the distal member and constituting a movable section of the treatment unit for clamping a living tissue in cooperation with the distal member; a manipulating means to be handled for clamping or freeing a living tissue using the holding member and distal member; an operation member for driving the holding member responsively to a movement of the manipulating means; and a turning mechanism for turning the treatment unit relative to the manipulating means with the axial direction of the ultrasonic transducers as a center.

Further, an ultrasound treatment system in accordance with the present invention comprises an ultrasonic transducer, a handpiece, a probe, a sheath, a clamping member, an operating means, an operating member, a suction base, and a perfusion base. The ultrasonic transducer generates ultrasonic vibrations. The handpiece has the ultrasonic transducer incorporated therein and serves as an operation unit. The probe is connected to the ultrasonic transducer and transmits ultrasonic vibrations to a distal member realizing a stationary portion that is a treatment portion for treating a living tissue. The sheath serves as a protecting member for shielding the probe. The clamping member is opposed to the distal member at the distal end of the sheath, and realizes a movable portion that is another treatment portion for clamping a living tissue in cooperation with the distal member. The operating means is manipulated for clamping a living tissue with the clamping member and distal member or freeing the living tissue therefrom. The suction base is formed on the back end of the handpiece and communicating with a through hole bored substantially along the center axes of the probe and ultrasonic transducer. The suction base is formed on the outer circumference of the handpiece and communicating with the lumen of the sheath.

OBJECTS OF THE INVENTION

An object of the present invention is to provide an ultrasound treatment system in which a treatment unit of an ultrasound treatment appliance can turn relative to a manipulating means and the ultrasound treatment appliance can therefore be used under endoscopic observation or the like with good maneuverability in the same manner as a surgical appliance.

Another object of the present invention is to provide an ultrasound treatment system in which an ultrasound treatment appliance offers superb maneuverability and the components of the ultrasound treatment appliance can be disassembled and assembled readily.

Another object of the present invention is to provide an ultrasound treatment system making it possible to conduct both a treatment by ultrasonic vibrations and a treatment by a high-frequency current properly and readily with safety ensured.

Yet another object of the present invention is to provide an ultrasound treatment system making it possible to prevent a treatment member from touching a normal tissue unnecessarily, to simplify the work of safety inspection, to improve the maneuverability for treatments, and to in general conduct surgery safely.

Yet another object of the present invention is to provide an ultrasound treatment system capable of incising and coagulating a living tissue and evacuating a crushed tissue out of a body by utilizing an ultrasonic coagulation/incision function and suction function.

Still another object of the present invention is to provide an ultrasound treatment system capable of incising a living tissue readily and reliably while coagulating it.

A further object of the present invention is to provide an ultrasound treatment system for enabling smooth discharge of a living tissue sucked into a sheath, suppressing a rise in impedance, realizing high-efficiency ultrasonic driving, and thus preventing deterioration in a treating ability. Another object of the present invention is to provide an ultrasound treatment system for confining a coagulated range of a living tissue to an intended area, and preventing a nervous tissue or the like from being thermally injured.

Still another object of the present invention is to provide an ultrasound treatment system making it possible to uninterruptedly carry out a series of work steps of peeling and exposing a living tissue, emulsifying it, crushing it, sucking it, and discharging it to outside a body at the time of coagulating or incising the living tissue of an intended region.

Still another object of the present invention is to provide an ultrasound treatment system contributing to further improvement of maneuverability and a drastic reduction in time required for a surgery.

Yet another object of the present invention is to provide an ultrasound treatment system capable of incising and coagulating a living tissue and evacuating a crushed tissue out of a body by utilizing an ultrasonic coagulation/incision function and suction function.

BRIEF DESCRIPTION OF THE DRAWINGS

FIGS. 3 to 11 are views for explaining the first embodiment of the present invention;

FIG. 3 is a plan view showing an ultrasound treatment appliance;

FIG. 4 is a sectional view for explaining the structures of a treatment unit and insertion unit of the ultrasound treatment appliance;

FIG. 5 is a D1-D2-D3-D4 sectional view of FIG. 4;

FIG. 6 is a view showing the treatment unit in FIG. 4 from the front thereof;

FIG. 7A is a 7A-7A sectional view of FIG. 4;
FIG. 7B is a 7B-7B sectional view of FIG. 4;
FIG. 7C is a 7C-7C sectional view of FIG. 4;
FIG. 7D is a 7D-7D sectional view of FIG. 4;
FIG. 7E is a 7E-7E sectional view of FIG. 4;
FIG. 7F is a 7F-7F sectional view of FIG. 4;
FIG. 8 is a plan view showing an operation unit;
FIG. 9A is a sectional view of the operation unit;
FIG. 9B is an enlarged sectional view of part of FIG. 9A.

FIGS. 12A and 12B are view for explaining the second embodiment of the present invention;

FIG. 12A is a side view for explaining the structure of a treatment unit of an ultrasound treatment appliance;

FIG. 12B is a front view for explaining the structure of the treatment unit of the ultrasound treatment appliance;

FIGS. 13A and 13B are views for explaining the third embodiment of the present invention;

FIG. 13A is an oblique view of a treatment unit of an ultrasound treatment appliance;

FIG. 13B is an explanatory view showing a meshing side of a holding member constituting the treatment unit;

FIG. 17A is an oblique view showing a bearing and ball click mechanism of a manipulating means;

FIG. 17B is a sectional view for explaining a ball click and an elastic member;

FIGS. 18 and 19 are views for explaining the eighth embodiment of the present invention;

FIG. 18 is a sectional view showing the structure of an operation unit;

FIG. 19 is an oblique view showing the structure of a bearing of the operation unit;

FIGS. 20 to 25 are views for explaining the ninth embodiment of the present invention;

FIG. 20 is a plan view showing an ultrasound treatment appliance of this embodiment;

FIG. 21A is a sectional view showing part of a probe including a treatment unit of the ultrasound treatment appliance;

FIG. 21B is a sectional view showing part of the treatment unit;

FIG. 23 is a sectional view showing an insertion unit of an ultrasound treatment appliance;

FIG. 24 is a sectional view showing an operation unit;

FIGS. 27 to 39 are views for explaining the eleventh embodiment of the present invention;

FIG. 27 is an oblique view showing the outline configuration of the ultrasound treatment appliance;

FIG. 28 is an oblique view showing the ultrasound treatment appliance in a state in which a sheath is detached from an operation unit;

FIG. 29 is an oblique view showing the ultrasound treatment appliance in a state in which a vibration conveying rod and rotor are dismounted from the sheath;

FIG. 30 is a view for explaining an example of a method of locking the rotor in the operation unit;

FIG. 31 is a view for explaining another method of locking the rotor in the operation unit;

FIG. 33 is a view for explaining an example of finishing the surface of a distal member constituting a treatment unit;

FIG. 35 is a view for explaining another shape of the distal member constituting the treatment unit;

FIG. 37 is a view for explaining a structure for coupling the coupling members with the vibration conveying rod;

FIG. 38A is an explanatory view showing the structure of junctions for coupling the distal member, vibration conveying rod, and horn;

FIG. 38B is a view showing a state in which the distal member and vibration conveying rod are coupled with each other;

FIG. 38C is a view showing another structure of the junctions for coupling the distal member, vibration conveying rod, and horn;

FIG. 40 is an explanatory view showing the structure of an ultrasound treatment appliance;

FIG. 41 is an oblique view for explaining the structure of a treatment unit of the ultrasound treatment appliance;

FIG. 42 is a view for explaining the turning relationship of a holding member and a sheath relative to a distal member;

FIG. 43 is a view for explaining the turning relationship of the holding member, sheath, and protective tube relative to the distal member;

FIGS. 44 to 46 are views for explaining the thirteenth embodiment of the present invention;

FIG. 44 is an oblique view showing an ultrasound treatment appliance;

FIG. 45 is an explanatory view showing the inner structure of a sheath;

FIG. 47 is an explanatory diagram showing the overall configuration of an ultrasound treatment system;

FIG. 48 is an explanatory diagram showing an ultrasound treatment appliance and the electrical configuration of a driving system for the ultrasound treatment appliance;

FIG. 49 is a diagram for explaining in detail the configuration of a drive unit;

FIG. 50 is an explanatory diagram showing the overall configuration of an ultrasound treatment system;

FIG. 51 is an oblique view showing a treatment unit of an ultrasound treatment appliance;

FIG. 53 is an explanatory view showing the structure of an ultrasound treatment appliance;

FIG. 54 is a sectional view for explaining the distal portion of an insertion unit of the ultrasound treatment appliance and a treatment unit thereof;

FIG. 55 is a 55-55 view of FIG. 54;

FIG. 56 is a 56-56 view of FIG. 54;

FIG. 57 is a sectional view for explaining the proximal portion of an insertion unit of the ultrasound treatment appliance and an operation unit thereof;

FIG. 58 is an explanatory diagram showing the circuitry of an ultrasound treatment system;

FIGS. 63 to 65 are views for explaining the eighteenth embodiment of the present invention;

FIG. 64 is a sectional view for explaining the structure of a treatment section of an ultrasound treatment appliance;

FIG. 65 is a view for explaining a use state of the ultrasound treatment appliance;

FIG. 70A is a diagram for explaining a state before ultrasonic oscillations occur;

FIG. 70B is a diagram showing a state in which ultrasonic oscillations occur;

FIG. 72 is a plan view showing an ultrasound treatment appliance;

FIG. 73 is a view showing the structure of a treatment unit of the ultrasound treatment appliance;

FIG. 74 is a diagram for explaining the shapes of a holding member and distal member constituting the treatment unit.

FIG. 77 to FIG. 84 are diagrams for explaining the twenty-eighth embodiment of the present invention;

FIG. 77 is an oblique view showing a handpiece of an ultrasonic incision/coagulation system of the twenty-eighth embodiment;

FIG. 80 is a diagram for explaining a clamping member driving mechanism and a probe included in the internal unit of the handpiece of the ultrasonic incision/coagulation system;

FIG. 82 is an oblique view showing a treatment portion of the handpiece of the ultrasonic incision/coagulation system;

FIG. 83A is a front view showing a closed state of a clamping member that is the treatment portion of the handpiece of the ultrasonic incision/coagulation system;

FIG. 83B is a front view showing a closed state of the clamping member that is the treatment portion;

FIG. 84 shows the overall configuration of an ultrasonic incision/coagulation system;

FIG. 86 is an oblique view showing a treatment portion of a handpiece of an ultrasonic incision/coagulation system in accordance with the thirtieth embodiment of the present invention; and FIG. 87 is an oblique view showing a treatment portion of a handpiece of an ultrasonic incision/coagulation system in accordance with the thirty-first embodiment of the present invention.

DETAILED DESCRIPTION OF THE PREFERRED EMBODIMENT

Figure 1:
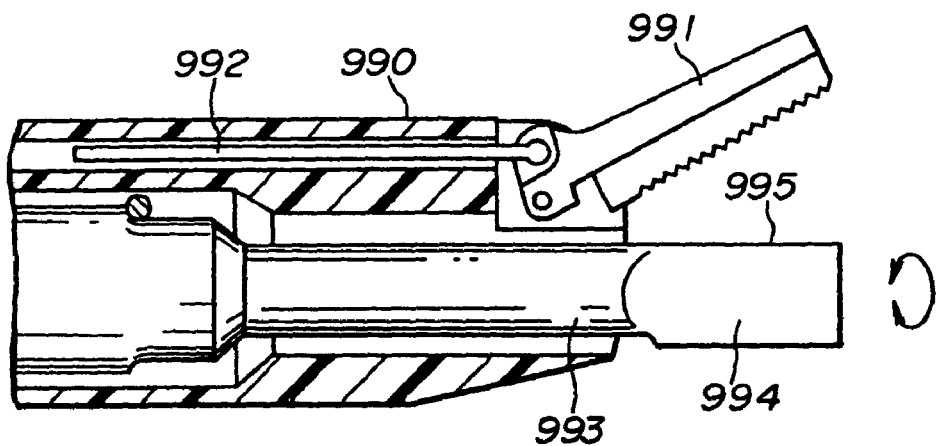
FIG. 1 is an explanatory diagram showing the structure of a treatment unit of an ultrasound treatment appliance that is a related art of the present invention.
Figure 2:
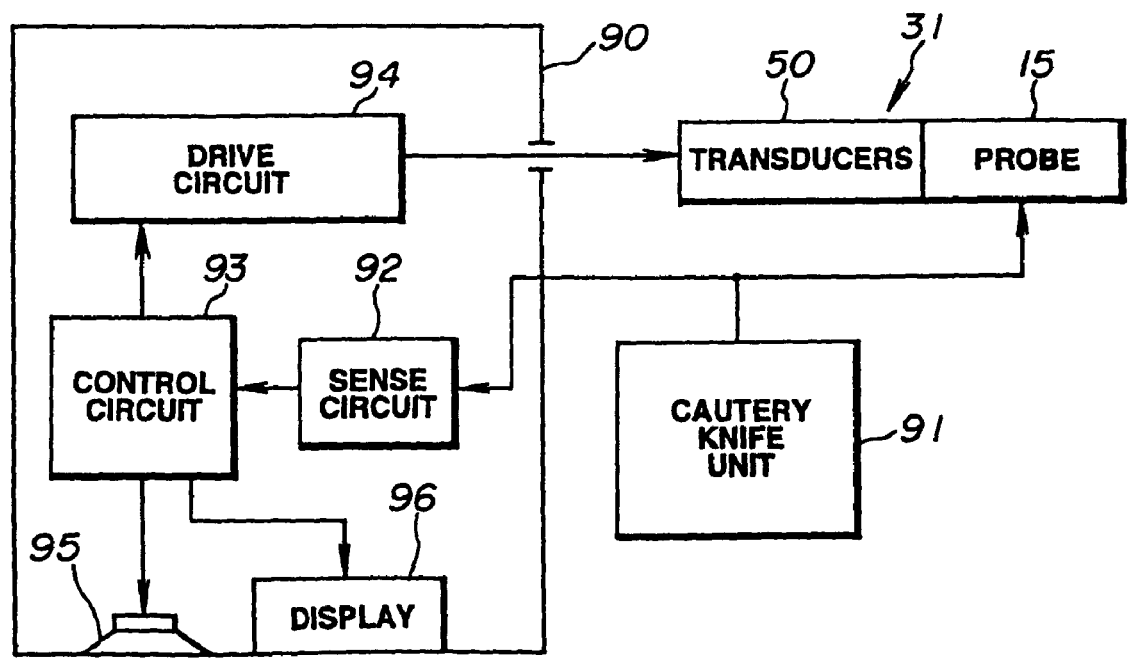
FIG. 2 is an explanatory diagram showing the conceptual configuration of the present invention.

As shown in FIG. 2, an ultrasound treatment system 99 provides superb maneuverability for the treatment of a living body by means of ultrasonic vibrations or a cautery knife, and includes an ultrasound treatment appliance 31 whose components can be disassembled or assembled readily, and a drive unit 90. The ultrasound treatment appliance includes ultrasonic transducers 50, and a probe for conveying ultrasonic vibrations to a distal portion for the purpose of a treatment such as coagulation. A driving signal is applied from a drive circuit 94 in the drive unit 90 to the ultrasonic transducers 50. The application of the driving signal brings about ultrasonic vibrations.

A cautery knife signal can be applied from a cautery knife unit 91 to the probe 8, whereby a treatment by a cautery knife can be conducted.

A sense circuit 92 for sensing whether or not a cautery knife signal is present on a line over which a cautery knife signal is transmitted is included in the drive unit 90. An output of the sense circuit 92 is output to a control circuit 93. When a cautery knife signal is detected, the control circuit 93 gives the alarm to an operator or nurse through, for example, a speaker 95, notifies them of the fact using a display 96, and switches off the drive circuit 94 so that a driving signal sent from the drive circuit 94 will not be output to the ultrasonic transducers 50. By contrast, when a cautery knife signal is not detected, the drive circuit 94 is switched on so that the driving signal will be output to the ultrasonic transducers 50.

Thus, an on-off operation of supply of a driving signal is performed according to a result of detection of a cautery knife signal. A treatment by ultrasonic waves and a treatment by a cautery knife can therefore be conducted selectively. It can be prevented that both the ultrasonic transducers and cautery knife are driven simultaneously by mistake. Safety can be ensured.

Referring to FIGS. 3 to 11, the first embodiment of the present invention will be described.

Figure 3:
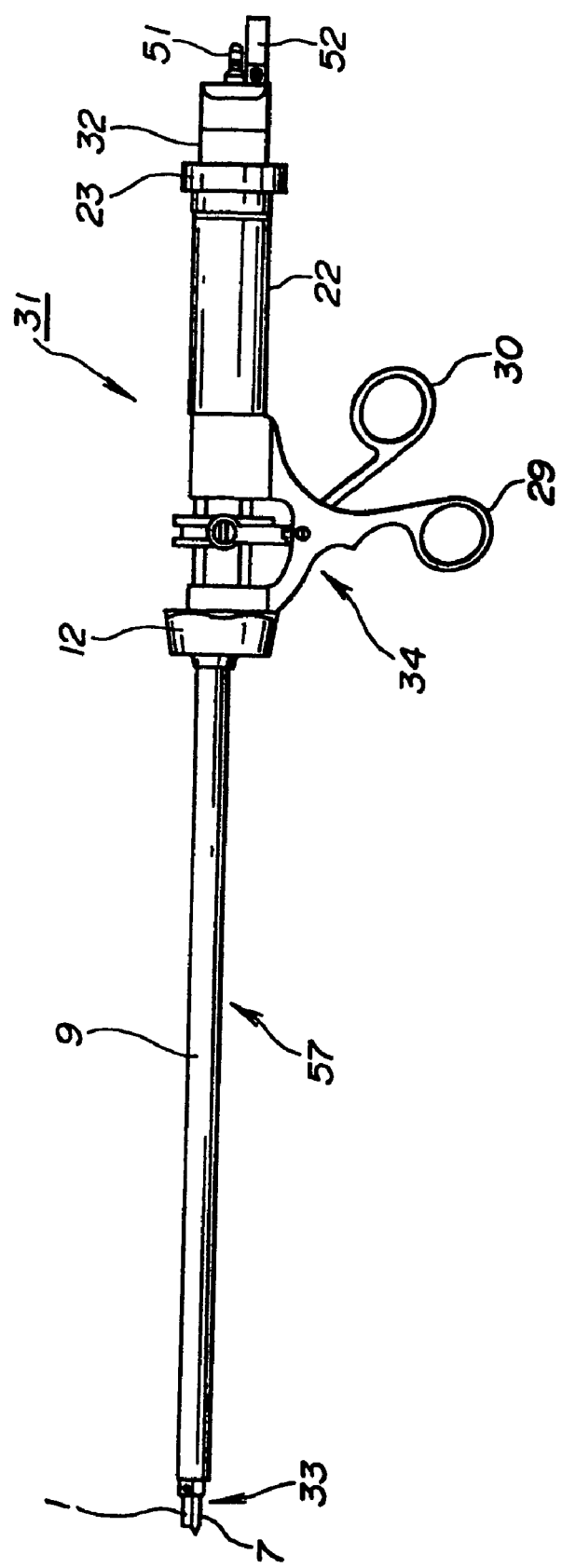

As shown in FIG. 3, an ultrasound treatment appliance 31 of the first embodiment of the present invention includes an insertion unit 57 having a treatment unit 33, which is used to conduct a treatment, attached to a distal end thereof, and a manipulating means 34 formed at the proximal end of the insertion unit 57 and used to manipulate the treatment unit 33. The insertion unit 57 has an insertion unit armor formed with an elongated sheath 9 so that the insertion unit 57 can be inserted in a living body.

At the upper proximal end of the manipulating means 34, a sheath 22 whose diameter is larger than that of the sheath 5 is located. A handpiece 32, which supplies ultrasonic vibrations used for incision and coagulation to the treatment unit 33, includes ultrasonic transducers 50 shown in FIG. 9A, and serves as a transducer unit, is formed at the proximal end of the sheath 22.

Figure 4:
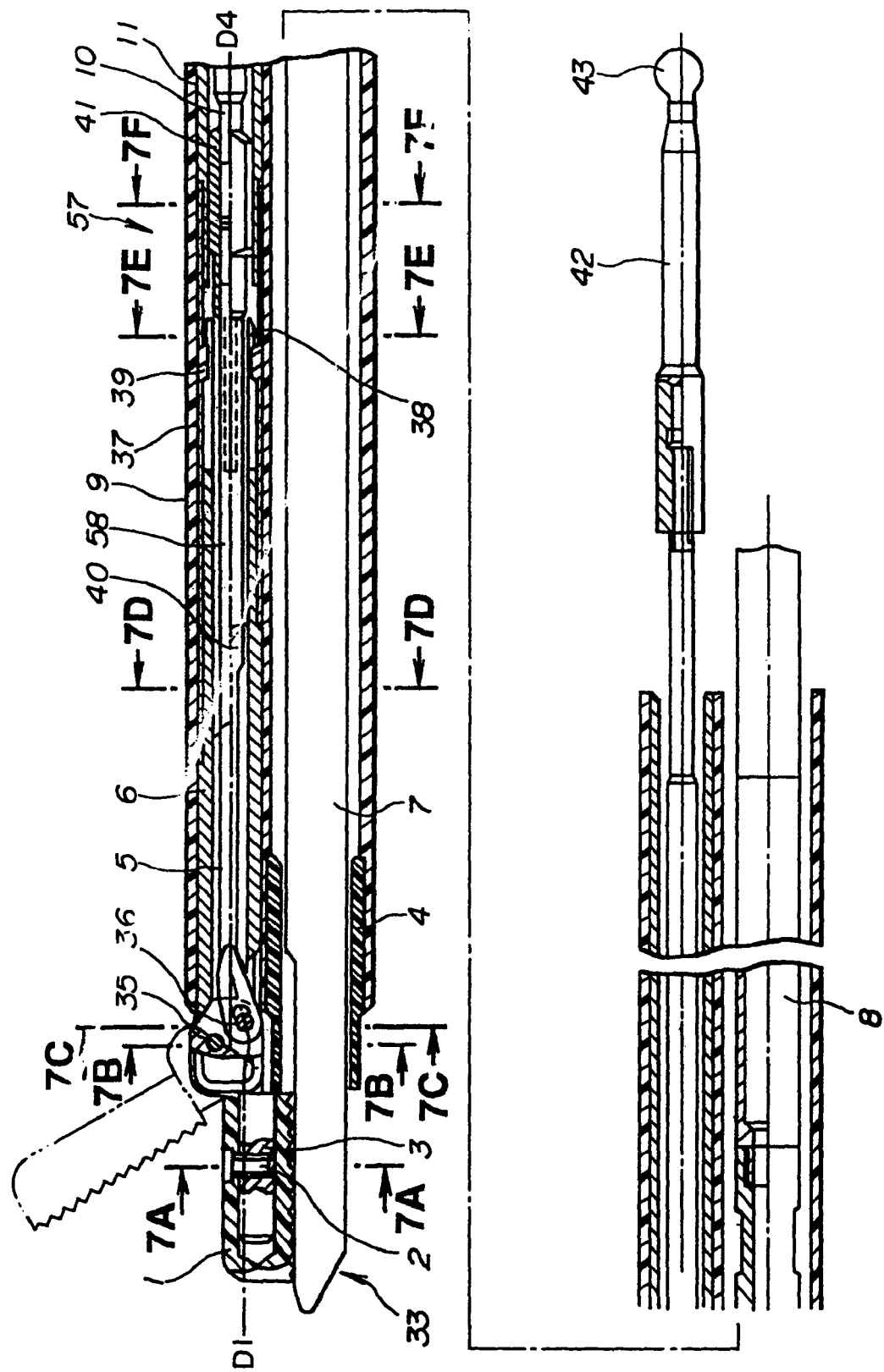

As shown in FIG. 4, the sheath 9 constituting the insertion unit 57 has, for example, two independent upper and lower channels which are protected by the sheath 9. A forceps unit 58 serving as a treatment instrument used to conduct a treatment of incision and coagulation lies through the upper channel. A probe 8 serving as a vibration conveying member for conveying ultrasonic vibrations stemming from the ultrasonic transducers 50 in the handpiece 32, and a distal member 7 screwed to the distal end of the probe 8 so that the distal member 7 will be freely detachable are inserted in the lower channel.

The treatment unit 33 and insertion unit 57 have structures shown in FIGS. 4 to 7F.

A movable member, which conveys manipulation force applied by the manipulating means 34, can advance and withdraw freely, and is shaped substantially like a cylinder, is inserted in a pipe-like armor member of the forceps unit 58. Moreover, a holding member 1 that clamps or frees a living tissue in cooperation with the distal member 7 located at the distal end of the probe 8 is attached to a movable section 3 that is the distal portion of the forceps unit 58 by a screw 2. That is to say, as shown in FIG. 6, the bottom of the holding member 1 and the top of the distal member 7 are shaped substantially like planes. The planes clamp or free a living tissue.

Figure 5:
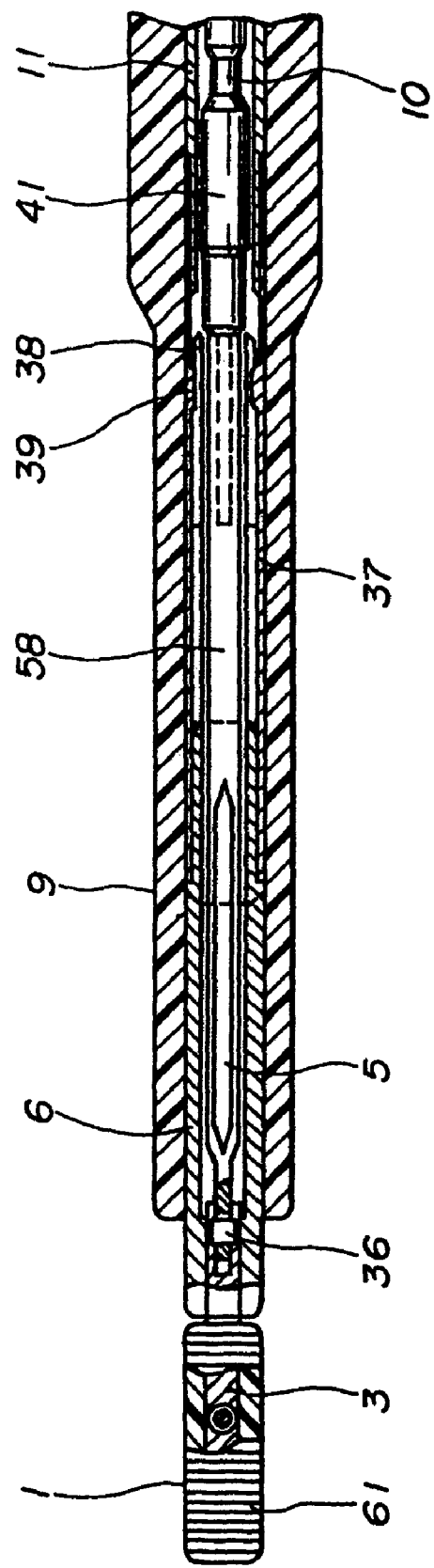

As shown in FIG. 5, coagulation ditches 61 that are transverse ditches extending transversely are formed on the bottom plane of the holding member 1 so that a tissue can be held reliably to facilitate coagulation.

As shown in FIGS. 4 and 5, the movable section 3 is supported at the distal end of a first operation member 5 serving as an operation member of the forceps unit 58 so that the movable section 3 can freely pivot with a pin 35 as a center. The movable section 3 pivots about the pin 35 as a center in relation to the advancement and withdrawal of a pin 36 fitted in an elongated hole.

A coupling member 41 is screwed tightly to the proximal end of the first operation member 5. The distal end of a second operation member 10 is screwed tightly to the coupling member 41. The proximal end of the second operation member 10 is jutting out proximally from the proximal end of the sheath 9 constituting the insertion unit 57. The distal end of an engaging member 42 is connected to the jutting proximal end of the second operation member 10 by means of a screw. In other words, the first operation member 5 constituting the forceps unit 58 is coupled with the second operation member 10, which is proximal to the first operation member 5, and the engaging member 42, which is proximal to the second operation member 10, using screws, so that these components can be disassembled and assembled.

A spherical section 43 is formed at the proximal end of the engaging member 42. The spherical section 42 is held by an upper locking mechanism of a movable manipulation handle 30 constituting the manipulating means 34 shown in FIGS. 3 9A, and 9B so that the spherical section 43 can advance or withdraw in a direction of the axis of the insertion unit 57. With the opening or closing of the movable manipulation handle 30, the engaging member 42, second operation member 10, and first operation member 5 are driven to advance or withdraw. Consequently, as mentioned above, the movable section 3 can be opened or closed.

A sheath 11 constituting an armor member of the forceps unit 58 has the proximal end thereof joined or coupled with a pipe 14 together with an outer sheath 10 thereof via a joining member 13 at a position inside a knob 12. The pipe 14 is mounted in a stationary manipulation handle 29 serving as a stationary manipulation member of the manipulating means 34.

The holding member 1 and screw 2 are molded using an insulating material such as a resin in case consideration is, as mentioned later, taken into a treatment to be conducted by feeding a high-frequency current. In any other case, the holding member 1 and screw 2 may be molded using a metal or the like.

As shown in FIGS. 4 and 5, a meshing member 37 shaped substantially like a cylinder is inserted in the upper channel of the sheath 9 through which the forceps unit 58 lies. A jut 39 jutting out radially internally is formed on the inner circumference of the proximal end of the meshing member 37. A snap-fit 38 formed at the proximal end of a distal cover 6 is engaged with the jut 39. When the snap-fit 38 of the distal cover 6 is pushed proximally beyond the jut 39, the snap-fit 38 and jut 39 can be engaged with each other. Consequently, the forceps unit 58 can be locked in the sheath 9. By strongly pulling the forceps unit 58 toward the distal end of the sheath 9, the snap-fit 38 and jut 39 are disengaged from each other. Consequently, the forceps unit 58 and sheath 9 can be disassembled; that is, the forceps unit 58 can be dismounted from the sheath 9.

At this time, if the holding member 1 is opened even slightly, the position of the coupling member 41 advances so that the distal end of the coupling member 41 will invade into the snap-fit 38. This invasion disables the snap-fit 38 from swaying in an inner circumferential direction. The forceps unit 58 cannot therefore be dismounted from the sheath 9.

In other words, for dismounting the forceps unit 58, the holding member 1 must be perfectly closed relative to the distal member 7. When the holding member 1 is not perfectly closed, for example, when the holding member 1 is used to clamp a living tissue in practical use, there is not the hazard that the forceps unit 58 may come off. The forceps unit 58 and sheath 9 can be disassembled or assembled each other with safety ensured.

At this time, since an anti-turn mechanism 40 is formed as a structure in which the portions of the meshing member 37 and distal cover 6 which engage with each other do not attain rotation symmetry, for example, a structure in which the position of the distal end of a stepped plane, which is formed on the outer circumference of the distal cover 6 so that the stepped plane can be engaged with the meshing member 37, varies in a circumferential direction of the distal cover 6, it can be prevented that the forceps unit 58 turns relative to the sheath 9. Moreover, a problem that when a living tissue is clamped, an unexpected turn occurs to deteriorate maneuverability.

The proximal end of the meshing member 37 is coupled with the sheath 11 lying in the sheath 9.

The probe 8 tightly screwed to the proximal end of the distal member 7 and designed to convey ultrasonic vibrations stemming from the ultrasonic transducers 50 to the distal member 7 is inserted in the lower channel of the sheath 9. The upper part of the distal end of the distal member 7 is a plane as shown in FIG. 7A, so that the distal member 7 can readily clamp a living tissue in cooperation with the holding member 1. The upper plane of the distal member 7 extends, as shown in FIGS. 7B and 7C, proximally farther than the holding member 1. The sectional shape of the portion of the distal member 7 proximally farther than the holding member 1 is, as shown in FIGS. 7D to 7F, circular.

The distal apex of the distal member 7 is molded substantially conically and jutting out distally farther than the holding member 1. This portion of the distal member 7 is used for ablation. The distal member 7 is freely detachable from the distal end of the probe 8 after being screwed. The holding member 1 is also freely detachable from the movable section 3 by means of the screw 2. The distal member 7 and holding member 1 can therefore be freely replaced with another ones. Thus, the distal member 7 and holding member 1 having optimal shapes can be put to use.

As shown in FIG. 4, a protective member 4 that is resistive to heat and durable to ultrasonic vibrations; such as, a member made of plytetrafluoroethylene (PTFE) or ceramic is located in a distal bore of the lower channel of the sheath 9. Owing to the protective member 4, it can be prevented that when a living tissue is clamped, if the distal member 7 reacts to bend downward, the distal member 7 and sheath 9 come into contact with each other to break.

FIGS. 8 to 11D show the manipulating means 34. The manipulating means 34 is located at the proximal end of the insertion unit 57. The sheath 9 and joining member 13 are attached to the manipulating means 34. The distal portion of the pipe 14 is attached to the outer circumference of the joining member 13. A knob 12 is engaged with the outer circumference of the distal portion of the pipe 14, and joined or fixed with or to the outer circumference thereof by a screw 44.

By loosening the screw 44, the knob 12 can be removed toward the distal end of the sheath 9. As described later, the sheath 9, pipe 14, and sheath 22 which constitute a sheath assembly can be disassembled or assembled relative to the manipulating means 34.

The pipe 14 lies through a first bearing 15 and second bearing 19 which are attached to the tops of the front and back portions of the bifurcating stationary manipulation handle 29. The pipe 14 is supported by the first bearing 15 and second bearing 19 which are fixed to the stationary manipulation handle 29 so that the pipe 14 will be freely turnable. An O ring 45 and two O rings 47 are placed on slidable interfaces between the outer circumference of the pipe 14 and the inner circumferences of the first bearing 15 and second bearing 19, thus restricting sliding at least in a circumferential direction and, in this embodiment, in a back-and-forth direction. Consequently, the magnitude of a torque for the pipe 14 relative to the bearing 15 or bearing 19 is made adjustable.

When the knob 12 is held and turned, the pipe 14 turns together with the knob 12 relative to the first bearing 15 and second bearing 19. The probe 8 lies through along the center axis of the pipe 14, while the forceps unit 58 lies through the sheath 9 off the center axis of the pipe 14. The forceps unit 58 is therefore turned about the center axis of the probe 8 which is aligned with the center axis of an ultrasonic transducers 50.

As apparent from FIG. 9 or the like, the center axis of the sheath 9 is not aligned with the center axis of the probe 8. When the knob 12 is turned, the insertion unit 57 having the treatment unit 33 attached to the distal end thereof or the sheath 9 turns in a decentered manner responsively to the turn of the pipe 14.

Figure 10A:
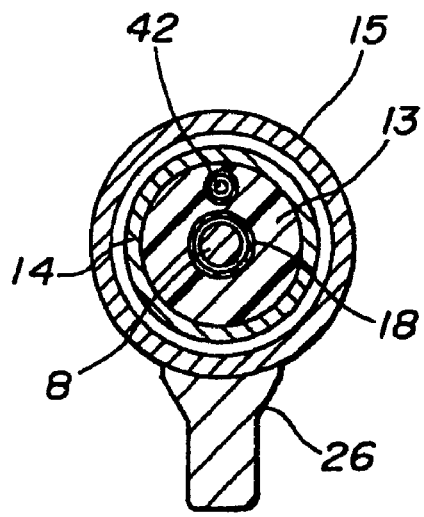
FIG. 10A is a 10A-10A sectional view of FIG. 9A.
Figure 10B:
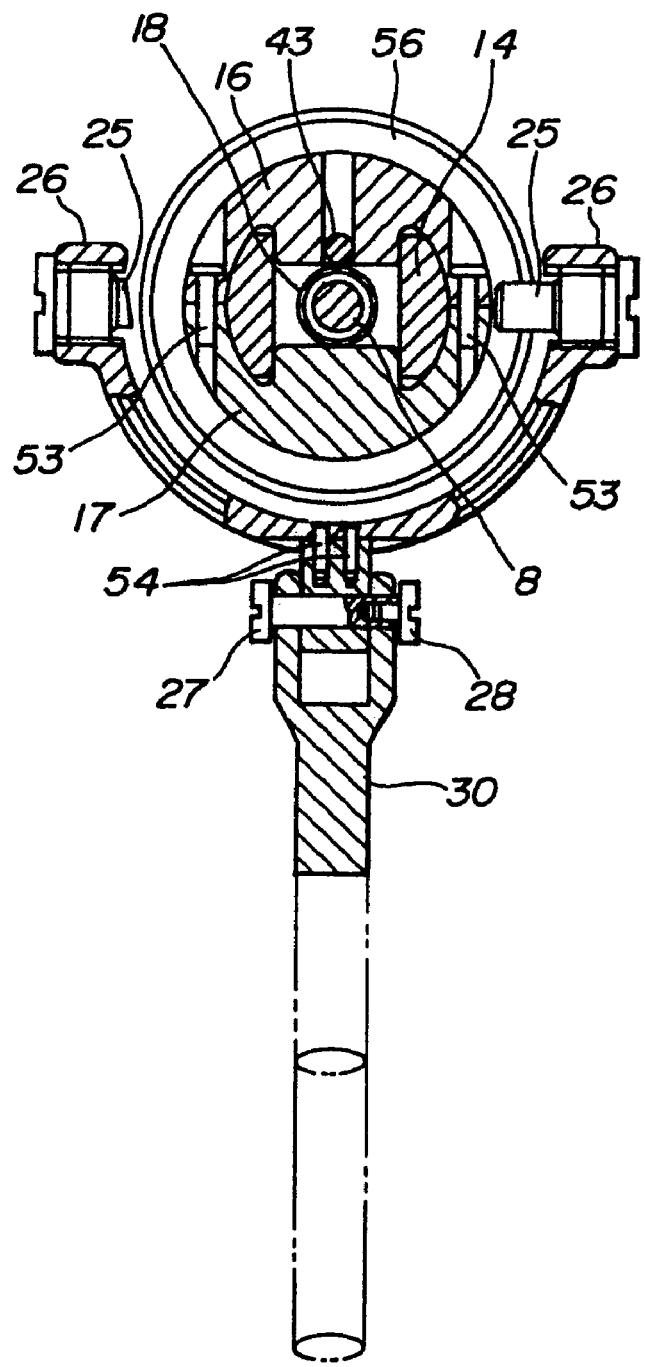
FIG. 10B is a 10B-10B sectional view of FIG. 9A.
Figure 11A:
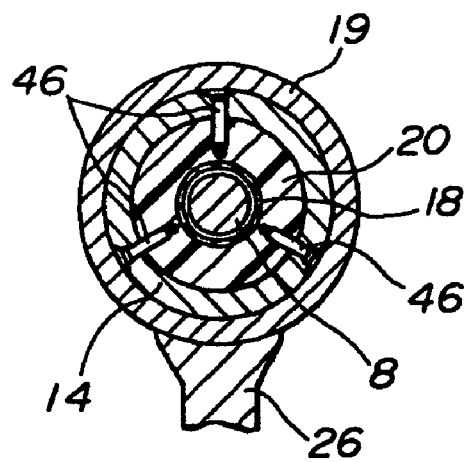
FIG. 11A is a 11A-11A sectional view of FIG. 9A.
Figure 11B:
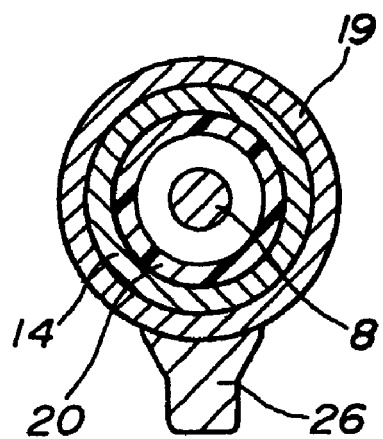
FIG. 11B is a 11B-11B sectional view of FIG. 9A.
Figure 11C:
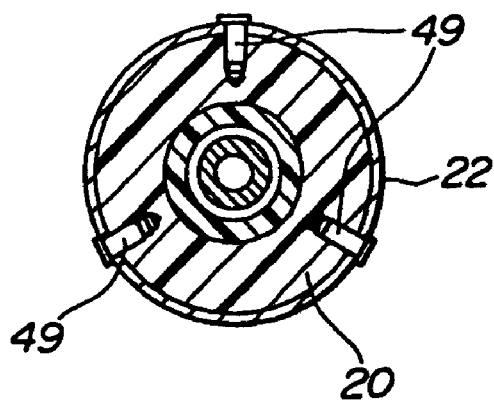
FIG. 11C is a 11C-11C sectional view of FIG. 9A.
Figure 11D:
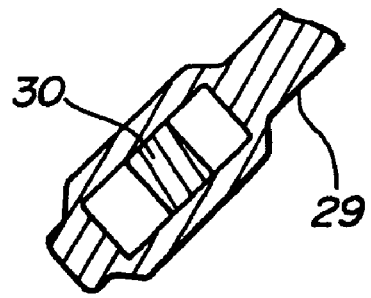
FIG. 11D is a 11D-11D sectional view of FIG. 9A.

As also shown in FIGS. 10A and 10B, the probe 8 coaxially lies through the cylindrical pipe 14 along the center axis of the pipe 14. The proximal end of the probe 8 is coupled with a vibration driving axis of the ultrasonic transducers 50, which generate ultrasonic waves and lie in the handpiece 32 that has a cylindrical outer circumference engaging with the cylindrical sheath 22 and that can slide freely, via a coupling member, for example, a screwing member. Thus, these components can be disassembled or assembled one another.

Figure 8:
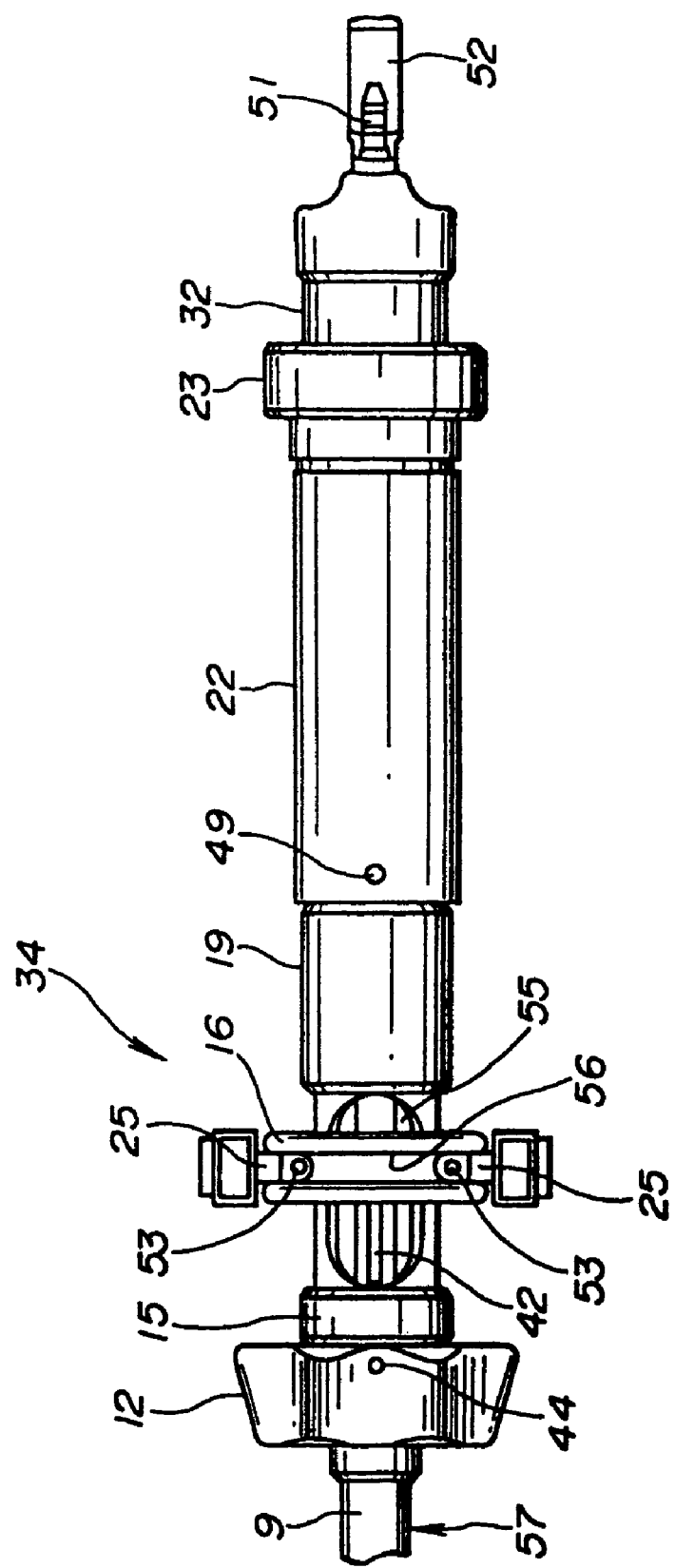

The pipe 14 has, as shown in FIG. 8, an elliptic ditch 55, which is bored vertically and elongated back and forth, formed on a portion thereof between the first bearing 15 and second bearing 19. Driving members 16 and 17 (See FIGS. 9 and 10B) that are each shaped substantially like a semi-disk are fitted vertically into the ditch 55 so that the driving members can freely move back and forth. The driving members 16 and 17 are then, as shown in FIG. 10B, joined with each other by screws 53. The driving members 16 and 17 drive the engaging member 42 so that the engaging member 42 can advance or withdraw. As mentioned above, when the operation members 10 and 5 are driven to advance or withdraw, the holding member 1 is opened or closed.

The engaging member 42 that is decentered and terminated at the middle of the pipe 14 is locked in a state in which the spherical section 43 formed at the proximal end of the engaging member 42 is fitted in an engagement ditch formed radially in the driving member 16 mounted on the top of the variable manipulation handle 30.

A joining member 20 is attached to the proximal portion of the pipe 14 by a screw 46 which joins the joining member 20 with the pipe 14 so that they can be disassembled or assembled each other. The sheath 22 in which the handpiece 32 is fitted is attached to the outer circumference of the proximal end of the joining member 20 by a screw 49. A thread is formed on the outer circumference of the proximal portion of the sheath 22. A ring 23 is mounted and engaged with the thread.

A backup ring 24 and an O ring 59 are stowed under the inner circumference of the ring 23. By turning the ring 23 in a direction in which the ring 23 is tightened to the operation unit sheath 22, the O ring 59 is compressed to stress the outer circumference of the handpiece 32. Thus, the handpiece 32 can be fixed to the sheath 22.

Owing to the foregoing structure, the handpiece 32 can be advanced or withdrawn relative to the sheath 22 by turning the ring 23 in a freeing direction. A quantity of jutting out the distal member 7 of the treatment unit 33 can be adjusted by advancing or withdrawing the handpiece 32. For example, therefore, a treatment can be conducted by setting a quantity of jutting-out suitable for the treatment of an object tissue. When the distal member 7 is replaced with another one to be used actually, a quantity of jutting-out suitable for a treatment can be set properly.

The handpiece 32 is provided with a guide sheath 21 extending distally. An O ring 48 is placed on the outer circumference of the distal end of the guide sheath 21. The guide sheath 21 and joining member 20 are thus sealed up.

A pipe 18 is used to link the joining member 13 and joining member 20 in order to shut off a channel, through which the portion of the probe 8 interposed between the joining member 13 and joining member 20 lies, from the outside. Thus, a sealed channel is constructed.

When a treatment is, as described later, conducted by feeding a high-frequency current to the probe 8, if the sheath 9, joining member 13, joining member 20, pipe 18, and guide sheath 21 are molded using an insulating material such as PTFE or polysulfone, safety can be ensured without the necessity of concerning about a leakage of a high-frequency current.

Owing to the foregoing structure, the forceps unit 58 and probe 8 are perfectly isolated from each other. When the forceps unit 58 is provided with a connector for connection, or a high-frequency current is fed directly, a living tissue can be treated by, for example, feeding a high-frequency current to the movable section 3 and distal member 7 selectively or by feeding the high-frequency current to both of them. Besides, a treatment can be conducted in a bipolar state in which a high-frequency current flows through a living tissue between both the movable section 3 and distal member 7.

In this case, it is recommended that the bare side of each of the driving member 16 driving member 17, stationary manipulation handle 29, movable manipulation handle 30, engaging member 42, bearing 15, bearing 19, sheath 22, and ring 23 be painted with an electrically insulating material, for example, PTFE in order to prevent a high-frequency current from flowing into an operator.

The channel through which the probe 8 lies and the channel proximal to the probe 8 are formed as sealed channels. Using the gap between the channels and the circumference of the probe 8, a channel through which a fluid can be passed for perfusion, aspiration, or the like by means of a perfusion/aspiration unit, which is not shown, connected to a perfusion/aspiration base 51 formed at the proximal end of the handpiece 32 can be realized. Bleeding blood can therefore be aspirated and discharged outside during, for example, incision.

A junction for a cord 52 is formed at the proximal end of the handpiece 32. Through the junction, a driving signal for triggering ultrasonic vibrations is applied from the drive unit 90 to the ultrasonic transducers 50 over the cord 52.

As described previously, the engaging member 42 is screwed tightly to the proximal end of the conveying member 10 penetrating the upper channel of the sheath 9. The spherical section 53 is formed at the proximal end of the engaging member 42. As shown in FIG. 10B, the spherical section 43 meshes with the engagement ditch of the driving member 16.

An engagement ditch 56 is formed circumferentially along the outer circumferences of the driving members 16 and 17. Driving pins 25 are fitted into the engagement ditch 56 at right-hand and left-hand positions. When the driving pins 25 move back and forth, the driving members 16 and 17 also move back and forth. The driving pins 25 are supported by both edges of a semicircular driving member 26. The bottom of the driving member 26 is joined with the top of the movable manipulation handle 30 by a screw 54.

The movable manipulation handle 30 and stationary manipulation handle 29 are joined by screws 27 and 28 so that the movable manipulation handle 30 can pivot freely.

When a manipulation is made to move the movable manipulation handle 30 back and forth relative to the stationary manipulation handle 29, the spherical section 43 moves back and forth via the driving pins 25 and driving members 16 and 17. Eventually, the holding member 1 of the forceps unit 58 can be opened or closed.

Specifically, when a finger rest formed as a lower part of the movable manipulation handle 30 is opened or closed, the driving member 26 advances or withdraws with the screw 27 as a supporting point. This causes the driving pins 25 to advance or withdraw. With the advancement or withdrawal of the driving pins 25, the driving members 16 and 17 advance or withdraw. The conveying member 10, coupling member 41, and conveying member 5 then advance or withdraw. This causes the movable section 3 to open or close as mentioned above. Eventually, the holding member 1 opens or closes.

When the knob 12 is turned relative to the manipulating means 34, the handpiece 32 turns in an interlocked manner. As a result, the treatment unit 33 can be turned relative to the manipulating means 34. Owing to this structure, an orientation in which a living tissue is clamped can be varied. Thus, the maneuverability for treatments is improved.

That is to say, when the treatment unit 33 is turned as mentioned above, the driving member 16 and driving member 17 are turned simultaneously. Since the outer circumferences of the driving members are circular and engaged with the driving pins 25 in the circular engagement ditch 56, the treatment unit 33 can be turned 360° relative to the manipulating means 34 without any problem.

Next, the actual procedure of using this embodiment will be described.

First, the ultrasound treatment appliance 31 is opposed to a living tissue to be treated. The orientation of the treatment unit 33 is matched with an orientation permitting smooth treatment by turning the knob 12. At this time, as mentioned above, the torque can be adjusted to an appropriate level by means of the O ring 45 and O ring 47. The torque is set to the level that allows the knob 12 to turn when a turn is needed but that does not permit a careless turn.

The movable manipulation handle 30 is then manipulated in an open direction in order to open the holding member 1. The object living tissue is interposed between the holding member 1 and distal member 7. The movable manipulation handle 30 is then closed so that the living tissue can be clamped by the holding member 1 and distal member 7.

By manipulating a foot switch or the like that is not shown, a driving signal is applied from the driving power supply for the ultrasonic transducers 50 to the ultrasonic transducers 50. The ultrasonic transducers 50 are then excited. The resultant ultrasonic vibrations are conveyed from the probe 8 to the distal member 7, and given to the clamped living tissue through the distal member 7. The clamped living tissue is heated with frictional heat until the living tissue has a high temperature, whereby coagulation or incision can be achieved. At this time, a living tissue can be incised or coagulated readily by optimizing a time and amplitude during and with which ultrasonic vibrations are given to a living tissue as well as a quantity of force with which the living tissue is clamped.

For example, the time is extended, the amplitude is increased, and the clamping force is intensified. The thus-set factors are convenient for incision. The opposite setting is convenient for coagulation.

When a living tissue is merely clamped, as mentioned above, the living tissue can be clamped by the distal member 7 and holding member 1.

For ablating a living tissue, the holding member 1 is closed or opened. The substantially conical section of the distal end of the distal member 7 is used to perform ablation bluntly. Alternatively, ablation may be conducted by imposing ultrasonic vibrations as mentioned above.

Furthermore, even when ultrasonic vibrations are imposed with the distal member 7 alone pressed to a living tissue, the living tissue can be incised or coagulated.

When a treatment using a high-frequency current is required, a high-frequency current is supplied from a high-frequency power supply that is not shown to the handpiece 32, and then fed from the handpiece 32 to the distal member 7 via the ultrasonic transducers 50.

Thus, a high-frequency current is fed to a living tissue through the distal member 7. Similarly to the aforesaid procedure using ultrasonic vibrations, the living tissue can be ablated, incised, or coagulated by the high-frequency current. At this time, as mentioned above, the channels of the probe 8 and of the forceps unit 58 are isolated from each other perfectly. Furthermore, the holding member 1 is molded with an insulating member. A treatment by a high-frequency current can therefore be achieved safely and efficiently without a high-frequency current leakage.

Moreover, a treatment by ultrasonic vibrations and a treatment by a high-frequency current may be conducted in combination if necessary.

Next, the procedure of disassembling or assembling the components of the ultrasound treatment appliance of this embodiment will be described.

First, the two screws 53 for joining the driving members 16 and 17 located on the movable manipulation handle 30 are removed from the ultrasound treatment appliance 31 shown in FIG. 3 in an assembled state. The driving members 16 and 17 are detached up and down from the pipe 14. The spherical section 43 is disengaged from the engagement ditch of the driving member 16. This makes it possible to free the proximal portion of the forceps unit 58.

Next, the holding member 1 is closed perfectly relative to the distal member 7, and pulled distally away from the sheath 9. This pulling causes the snap-fit 38 to sway in an inner circumferential direction and get over the jut 39. The forceps unit 58 can now be disassembled from the sheath 9.

The ring 23 located at the proximal end of the sheath 22 is then turned in a freeing direction in order to loose the joined state between the handpiece 32 and sheath 22. The handpiece 32 is then pulled out behind the manipulating means 34. This pulling makes it possible to dismount the handpiece 32 backward from the insertion unit 57 and manipulating means 34 together with the probe 8.

Thereafter, the probe 8 is turned relative to the handpiece 32 and thus unscrewed from the handpiece 32. The probe 8 is then dismounted from the handpiece 32. By performing unscrewing in the same manner, the distal member 7 is dismounted from the probe 8.

For disassembling the insertion unit 57 and manipulating means 34, the screw 44 of the knob 12 is removed from the knob 12, and then the knob 12 is dismounted from the distal portion of the sheath 9. A unit composed of the sheath 9, pipe 14, and sheath 22 is pulled out backward from the manipulating means 34, and thus dismounted from the driving member 26, movable manipulation handle 30, and stationary manipulation handle 29.

The foregoing series of operations brings the ultrasound treatment appliance 31 to a state in which the respective parts can be fully cleaned and sterilized. By removing the screw 54 for joining the driving member 26 with the movable manipulation handle 30, the driving member 26 and movable manipulation handle 30 can be disassembled.

By disassembling the screws 27 and 28, the stationary manipulation handle 29 and movable manipulation handle 30 can be disassembled. The guide sheath 21 and handpiece 32 can be disassembled by unscrewing.

The thus-disassembled members are cleaned and sterilized. After the cleaning and sterilization are completed, the components are assembled again by reversing the foregoing sequence. The ultrasound treatment appliance 31 is then constructed.

Since the structure permits disassembling and assembling as mentioned above, the disassembled components can be fully or reliably cleaned and sterilized without labor. If any member should be broken, the member alone would have to be replaced with a new one. The use of the ultrasound treatment appliance can be continued uninterruptedly. This is economic.

Furthermore, the forceps unit 58 is coupled with the proximal conveying member 10 by tightening a screw. When the forceps unit 58 is replaced with another one, another forceps unit 58 having a different shape or size suitable for a treatment can be used to conduct a treatment. Moreover, since the distal member 7 of the probe 8 can be disassembled or assembled freely, another distal member 7 having a different shape or size can be used for a treatment.

Referring to FIGS. 12A and 12B, the second embodiment of the present invention will be described.

FIGS. 12A and 12B show a major portion of the second embodiment of the present invention. This embodiment has substantially the same structure as the first embodiment. However, this embodiment aims mainly at incision of a living tissue, and is therefore devoid of the holding member 1. Instead, the distal end of the movable section 3 and the distal member 7 constitute scissors. A living tissue can therefore be incised efficiently and safely.

The other components are identical to those in the first embodiment. In this embodiment, the distal end of the movable section 3 and the tip of the distal member 7 are pressed against a living tissue to be incised. The movable section 3 is then moved from an open state in a closing direction, whereby ultrasonic vibrations are imposed on the living tissue in contact with the scissors. Thus, the living tissue can be resected.

In short, this embodiment provides the ability to resect or incise a living tissue by pinching it using scissors instead of the ability of the first embodiment to at least incise or coagulate a living tissue by clamping it. Similarly to the first embodiment, the knob 12 that is not shown in FIGS. 12A and 12B can be manipulated to turn the treatment unit 33 about the center axis of the probe 8; that is, the center axis of the ultrasonic transducers 50.

Disassembling and assembling can be performed in the same manner as those in the first embodiment. Cleaning and sterilization can therefore be achieved after disassembling. The advantages of this embodiment are substantially the same as those of the first embodiment.

Referring to FIGS. 13A and 13B, the third embodiment of the present invention will be described.

FIGS. 13A and 13B show a major portion of the third embodiment. This embodiment has substantially the same structure as the first embodiment. However, an incision plane 62 is formed on a plane that is opposed to the distal member 7 and interposed between the holding member 1 of the movable section 3 and the distal cover 6.

After a living tissue is clamped by the holding member 1 and distal member 7, a coagulation plane 61 is used to coagulate the living tissue. The incision plane 62 is formed by narrowing the portion of the movable section 3 proximal to the coagulation plane 61. A thin living tissue clamped by the incision plane 62 and distal member 7 can therefore be incised by them. The other components are identical to those in the first embodiment.

Owing to the foregoing structure, for example, when incision is conducted concurrently with coagulation, a living tissue is clamped and imposed ultrasonic vibrations by inching the holding member 1 and distal member 7 from an edge of the living tissue. A portion to be incised is therefore coagulated in advance without fail. The possibility of bleeding can be minimized, and incision can be achieved quite safely.

The other operations and advantages of this embodiment are identical to those of the first embodiment.

Figure 14:
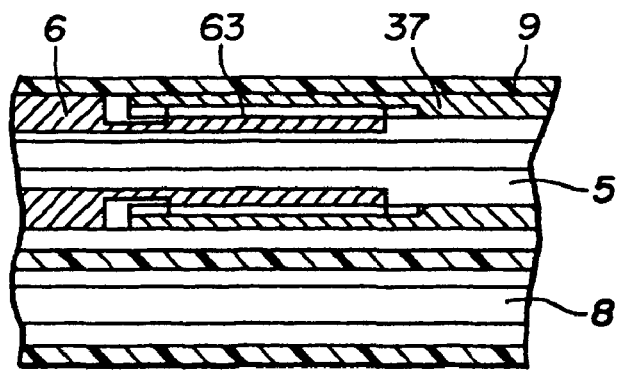
FIG. 14 is a sectional view showing part of an insertion unit in the fourth embodiment of the present invention.

Referring to FIG. 14, the fourth embodiment of the present invention will be described.

FIG. 14 shows a major portion of the fourth embodiment. This embodiment has substantially the same structure as the first embodiment. A means for fixing the forceps unit 58 to the sheath 9 is not the snap-fit 38. As shown in FIG. 14 illustrating a section equivalent to the 7E-7E section in FIG. 4, meshing threads 63 are formed on the distal cover 6 and meshing member 37 in order to realize a structure enabling disassembling and assembling.

The other components are identical to those in the first embodiment. The operations and advantages of this embodiment are substantially identical to those of the first embodiment except the operation for releasing a fixed state during disassembling and that for part of assembling.

Figure 15:
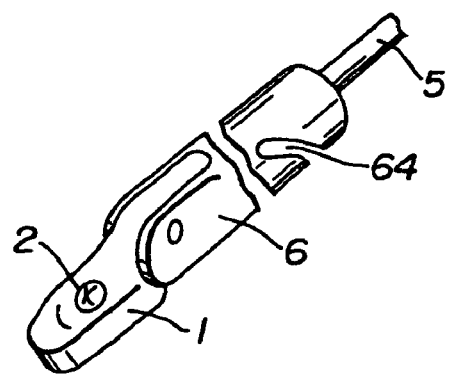
FIG. 15 is an oblique view showing the structure of an treatment unit in the fifth embodiment of the present invention.

Referring to FIG. 15, the fifth embodiment of the present invention will be described.

FIG. 15 shows a major portion of the fifth embodiment. This embodiment has substantially the same structure as the first embodiment. A means for fixing the forceps unit 58 to the sheath 9 is not the snap-fit 38. As shown in FIG. 15, a cam lock 64 formed on the distal cover 6 and the jut 39 (See FIGS. 4 and 7E) of the meshing member 37 are used to realize a structure enabling disassembling and assembling.

The other components are identical to those in the first embodiment. The operations and advantages of this embodiment are substantially identical to those of the first embodiment except the operation for releasing a fixed state during disassembling and that for part of assembling.

Figure 16:
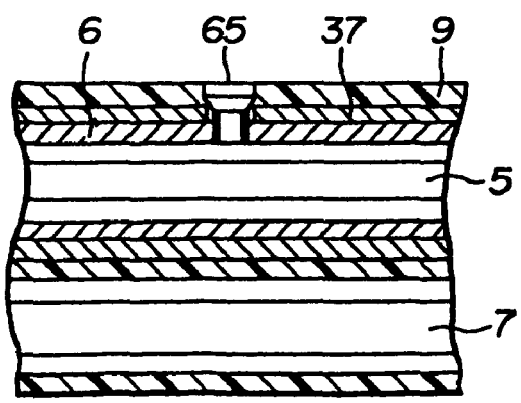
FIG. 16 is a sectional view showing the structure of part of an insertion unit in the sixth embodiment of the present invention.

Referring to FIG. 16, the sixth embodiment of the present invention will be described.

FIG. 16 shows a major section of the sixth embodiment of the present invention. This embodiment has substantially the same structure as the first embodiment. However, a means for fixing the forceps unit 58 to the sheath 9 is not the snap-fit 38. As shown in FIG. 16 showing a section equivalent to the 7D-7D section of FIG. 4 and its surroundings, an attachment screw 65 is used to realize a structure enabling disassembling and assembling. Specifically, a screw hole penetrating the sheath and meshing member 37 is formed in the distal cover 6. The attachment screw 65 is fitted into the screw hole. Thus, the structure enabling disassembling and assembling is realized using the attachment screw 65. If necessary, the attachment screw 65 may be tightened with an O ring for attaining watertightness placed intermediately.

The other components are identical to those in the first embodiment. The operations and advantages of this embodiment are substantially the same as those of the first embodiment except the operation for releasing a fixed state during disassembling and that for part of assembling.

Figure 17A:
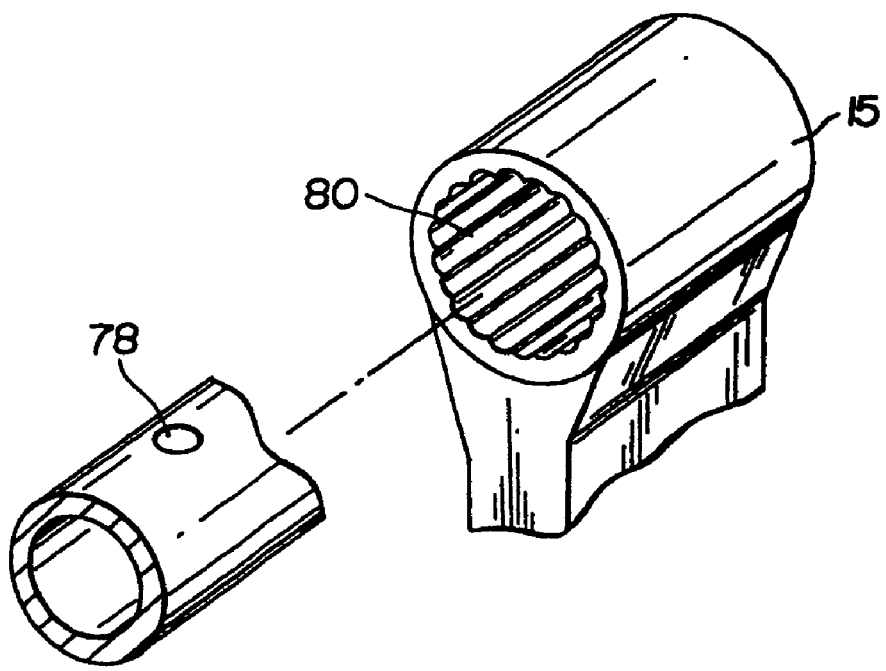
FIGS. 17A and 17B are views for explaining the seventh embodiment of the present invention.
Figure 17B:
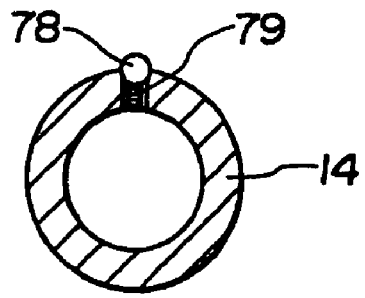

Referring to FIGS. 17A and 17B, the seventh embodiment of the present invention will be described.

This embodiment has substantially the same structure as the first embodiment. A fixing mechanism using a ball click to stop a turn is implemented in the bearing 15 or 19 and pipe 14.

An elastic member 79 such as a spring is stowed in a hole penetrating the pipe 14 between inside and outside. A ball 78 placed on the outer side of the elastic member 79 is constrained to go in an outer-circumferential direction by the elastic force of the elastic member 79. The inner diameter of the outer end of the hole which is formed in the pipe 14 and in which the ball 78 is stowed is smaller than the diameter of the ball 78. There is therefore not the hazard that the constrained ball 78 may pop up from the hall and come off.

Owing to the ball 78 and numerous click ditches 80 formed on the inner-circumferential surface of the bearing 15 or bearing 19 in a direction parallel to the center axis, the treatment unit 33 can be turned relative to the manipulating means 34 by any angle in units of a small angle and then locked at a position of any angle that is an integral multiple of the small angle.

In other words, in a normal use state, a fixed state in which turning is restricted can be set up by attaining an engaged state in which the ball 78 is fitted in any of the click ditches 80. When a turn is made with a torque permitting release of the engaged state, the fixed position can be varied.

The other components are identical to those of the first embodiment. The operations and advantages of this embodiment are substantially the same as those of the first embodiment except the operation for releasing the fixing mechanism during disassembling and that for part of assembling.

Figure 18:
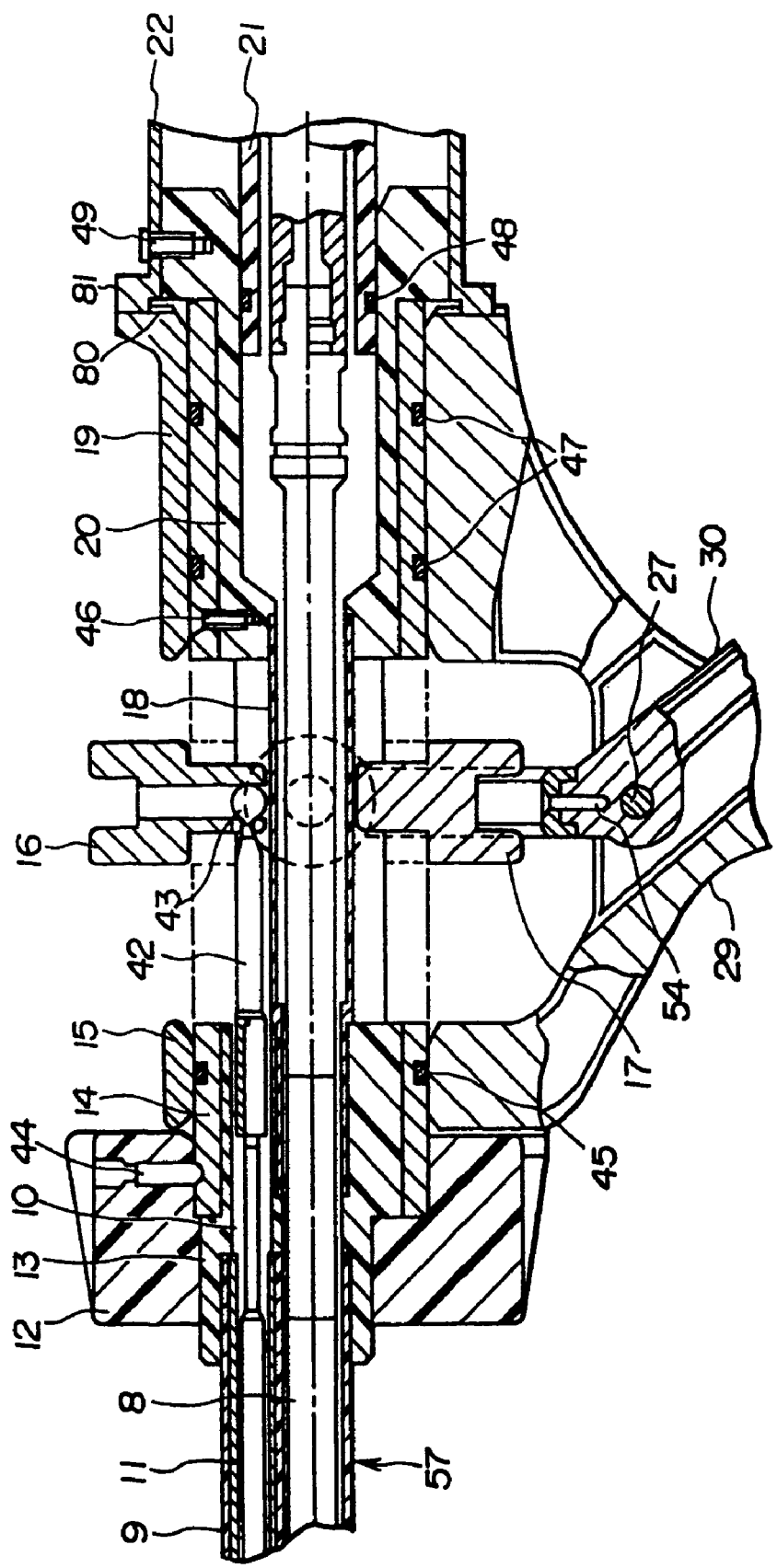

Referring to FIGS. 18 and 19, the eighth embodiment of the present invention will be described.

This embodiment has substantially the same structure as the first embodiment. However, numerous click ditches 80 are formed radially on a ring-shaped end surface of the second bearing 19 opposed to the sheath 22; that is, as seen from FIG. 18, a proximal end surface of the second bearing 19, and two click pawls 81 that are formed on an end surface of the sheath 22 opposed to the ring-shaped end surface. A fixing mechanism for stopping a turn is realized by engagement of any of the click ditches 80 and the click pawls 81. The knob 12 is molded using an elastic member. The other components are identical to those of the first embodiment.

Owing to the foregoing components, for turning the treatment unit 33, the knob 12 is pressed against the proximal end of the manipulating means 23. This causes the knob 12 to abut on the bearing 15 and deform elastically. Eventually, the click pawls 81 come off from the click ditches 80.

The knob 12 is then turned relative to the manipulating means 34, whereby the treatment unit 33 turns relative to the manipulating means 34. When the force used to press the knob 12 against the manipulating means 34 is released, the click pawls 81 mesh with the click ditches 80 again. Eventually, a stopped state in which a turn is restricted can be set up.

Assuming that the knob 12 is forcibly turned relative to the manipulating means 34 with the click pawls 81 meshed with the click ditches 80, when the click pawls 81 get over the ridges of the click ditches 80, the knob 12 deforms elastically as mentioned above. The treatment unit 33 can therefore be turned relative to the manipulating means 34. The other advantages are identical to those of the first embodiment.

Referring to FIGS. 20 to 25, the ninth embodiment of the present invention will be described.

The ultrasound treatment appliance 31 of the first embodiment has the structure that: two hollow channels are formed in the sheath 9 having the capability of a protective member; the forceps unit 58 having the treatment unit 33 is passed through one of the channels, and the probe 8 for conveying ultrasonic waves stemming from the ultrasonic transducers 50 is passed through the other channel; the proximal end of the forceps unit 58 is locked in the movable manipulation means of the manipulating means 34; and thus the holding member can be opened or closed relative to the distal member 7 of the probe 8 by manipulating the movable manipulation means. By contrast, this embodiment has such a structure as: a sheath 9 having the capability of a protective member has a single cylindrical hollow channel; a substantially cylindrical probe 8 is passed through the sheath 9; a conveying member coupled to a movable member of a treatment unit 33 is inserted in the probe 8; and the proximal end of the conveying member is extended backward in a hollow defined by annular ultrasonic transducers 50, and coupled with the movable manipulation means.

An ultrasound treatment appliance 31 has, as shown in FIG. 20, a treatment unit 33, and an insertion unit 57 for inserting the treatment unit 33 in a living body. A manipulating means 34 for manipulating the treatment unit 33 is located at the proximal end of the insertion unit 57. A handpiece 32 including ultrasonic transducers 50 for supplying ultrasonic vibrations used for a treatment to the treatment unit 33 is located at the upper proximal end of the manipulating means 34.

Figure 22A:
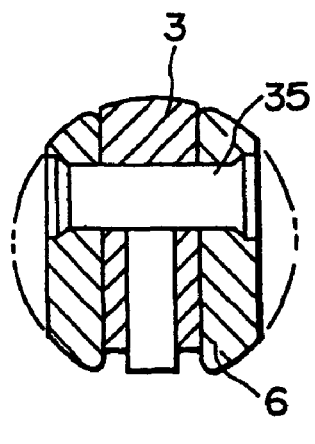
FIG. 22A is a 22A-22A sectional view of FIG. 21A.
Figure 22B:
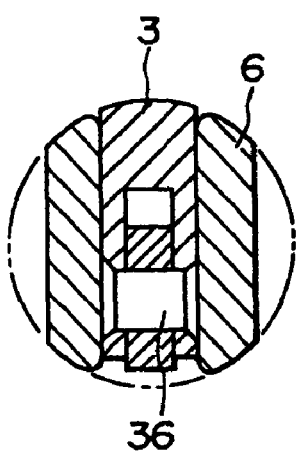
FIG. 22B is a 22B-22B sectional view of FIG. 21A.
Figure 22C:
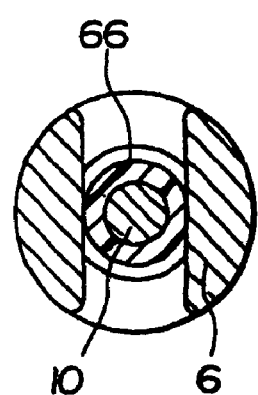
FIG. 22C is a 22C-22C sectional view of FIG. 21A.
Figure 22D:
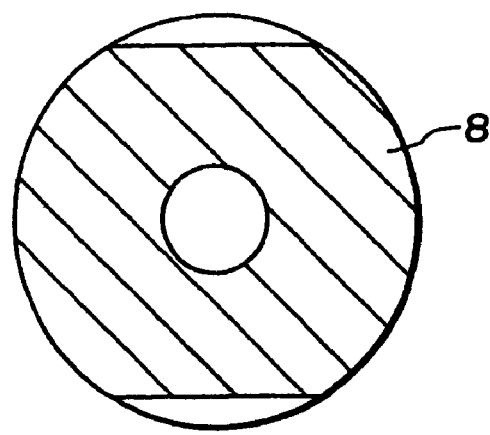
FIG. 22D is a 22D-22D sectional view of FIG. 21A.
Figure 23:
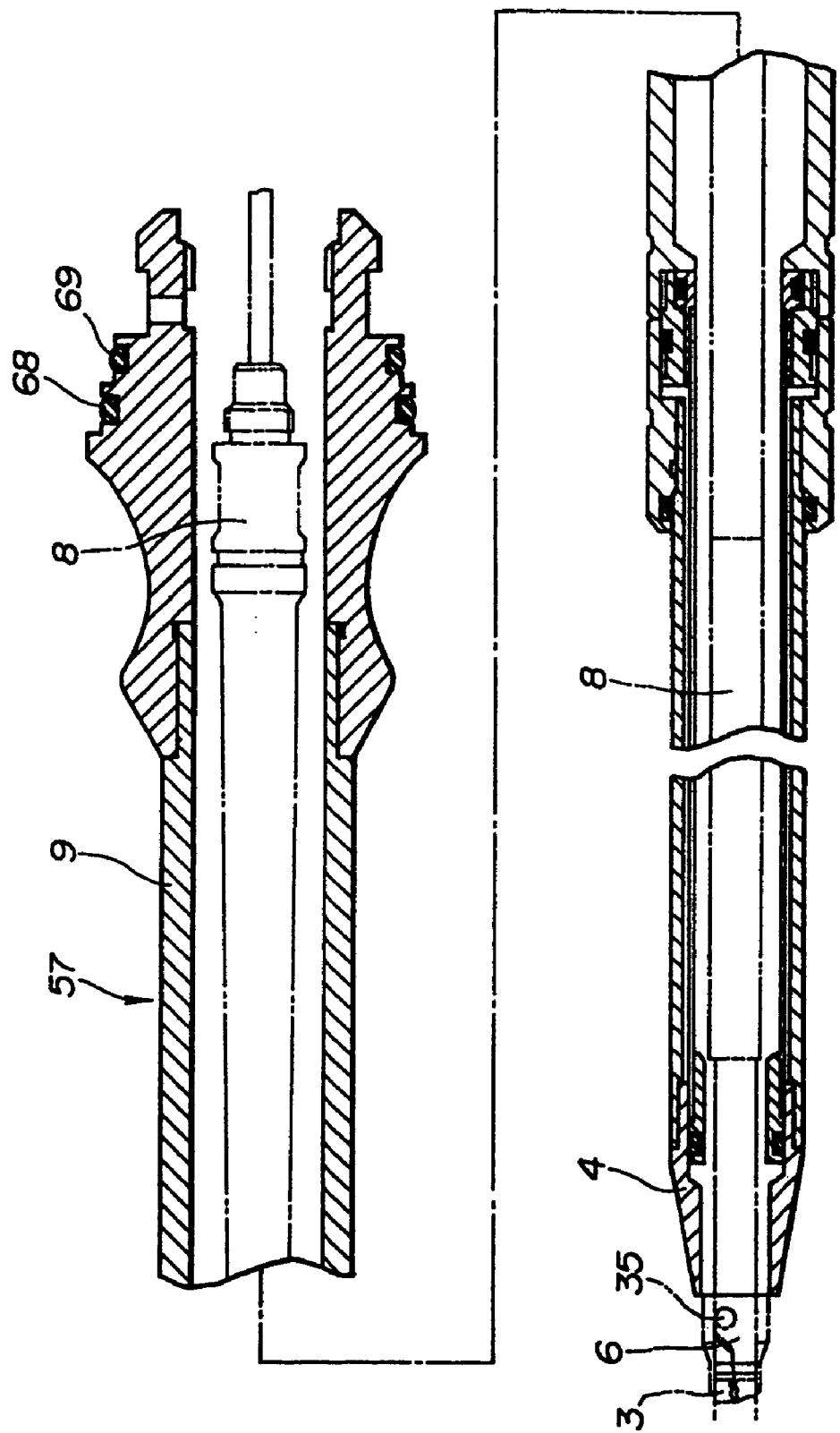

The structure including the treatment unit 33 and a probe 8 for conveying ultrasonic vibrations stemming from the ultrasonic transducers 50 to the treatment unit 33 is as shown in FIGS. 21 to 23. The treatment unit 33 is screwed to the distal end of the probe 8, and includes a distal member 7 used to treat a living tissue by means of ultrasonic vibrations.

The distal end of the distal member 7 is molded like a clamp. A distal cover 6 is formed to sandwich a movable section 3 in an area from the middle of the distal member 7 to the proximal end thereof. The movable section 3 and the distal end of the distal member 7 mesh with each other and function as forceps for clamping or freeing a living tissue.

In this embodiment, the distal end that is normally referred to as an ablation clamp is thin and shaped to be effective in ablation. As for the shape, the distal end may be shaped like scissors as that in the second embodiment or shaped like the movable section 3 in the third embodiment. The shape is not restricted to any particular one.

The movable section 3 is supported in the distal cover 6 by a pin 35 so that the movable section 3 can pivot freely. The movable section 3 is coupled with a conveying member 5 by a pin 36. A conveying member 10 is screwed to the proximal end of the conveying member 5.

The proximal portion of the distal cover 6 and the probe 8 are made hollow. A first operation member 5 and a second operation member 10 are lying through the hollows. The outer circumference of the second operation member 10 is covered with a tube 66 made of a material that is resistive to heat and absorbent of ultrasonic vibrations; such as; PTFE. Thus, when ultrasonic vibrations are imposed on the probe 8, occurrence of a metallic sound due to the contact of the probe 8 with the conveying member 10 or a hazard that a contact section is heated or broken is prevented.

Similarly to the first embodiment, an engaging member 42 is coupled with the proximal end of the conveying member 10 by tightening a screw. A spherical section 43 is formed at the proximal end of the engaging member 42. The engaging member 42 is driven to advance or withdraw with the opening or closing of a movable manipulation handle 30. When the conveying member 5 is driven to advance or withdraw, a force is conveyed to the movable section 3 via the pin 36. The movable section 3 is then driven to open or close relative to the distal member 7.

In an effort to prevent a hazard that a high-frequency current leaks out to an operator's hand or the like during a treatment using a high-frequency current which will be described later, the outer circumference of the engaging member 42 is covered with a tube 67 made of a material having an electrical insulation ability; such as, PTFE.

The probe 8 is composed of, for example, three parts. The three parts are coupled and assembled by performing TIG welding or the like at positions Q and R in FIG. 21A.

As shown in FIG. 22A, the pin 35 supporting the movable section 3 so that the movable section 3 can pivot freely is fixed to the distal cover 6 by caulking, laser welding, or the like. The pin 35 is thus united with the distal cover 6. When ultrasonic vibrations are conveyed to the distal cover 6 as mentioned above, the ultrasonic vibrations are also conveyed to the movable section 3 via the pin 35.

The treatment unit 33 and probe 8 having the foregoing structures are inserted in an insertion unit 57 that will be described later, and coupled with the ultrasonic transducers 50 in the handpiece 32 distal to the manipulating means 34.

The insertion unit 57 has the structure shown in FIG. 23. A protective member 4 made of a material that is resistive to heat and durable to ultrasonic vibrations; such as, PTFE or a ceramic is located at the distal end of the sheath 9 including a plurality of parts in order to prevent a metallic sound or heat dissipation from occurring due to the contact of the sheath 9 with the distal cover 6 or distal member 7 or to avoid that hazard that the sheath 9 and the distal cover 6 or distal member 7 are broken.

An O ring 68 and a C ring 69 are attached to the outer circumference of the proximal portion of the sheath 9. The proximal portion of the sheath 9 is connected to a screw ring 82, which will be described later, in a watertight manner. In this embodiment, the sheath 9 and screw ring 82 are connected to each other by means of the C ring 69. Alternatively, for example, the structure composed of the snap-fit 38 and jut 29 in the first embodiment, the connection mechanism using the attachment threads 63 in the fourth embodiment, the structure using the cam-lock 64 in the fifth embodiment, or the structure using the attachment screw 65 in the eighth embodiment will do. The connection means is not limited to any particular one.

Figure 24:
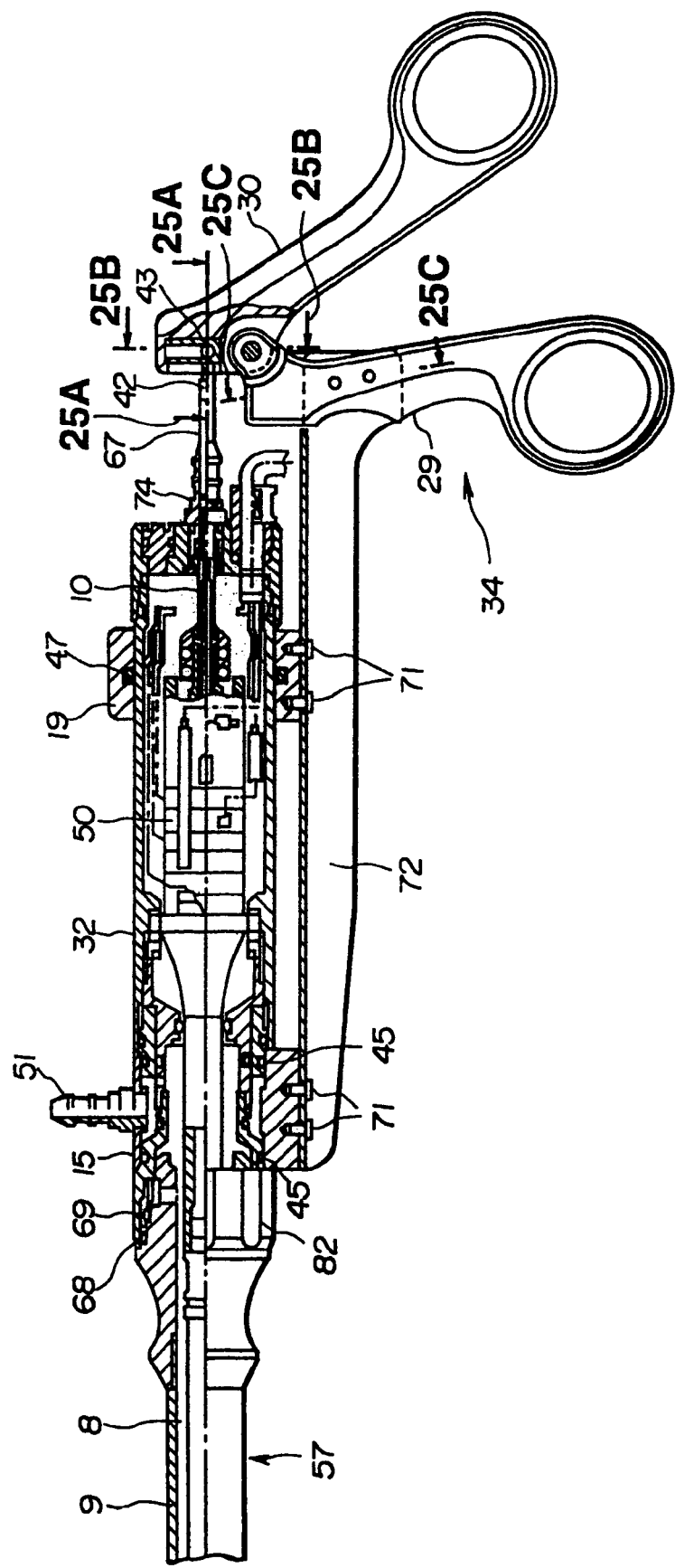

Next, the manipulating means 34 will be described. As shown in FIG. 24, a first bearing 15 is attached at the upper distal end of a supporting member 72 of the manipulating means 34 by means of screws 71. A second bearing 19 is attached at the upper middle of the supporting member 72 thereof by means of screws 73.

The screw ring 82 is inserted in the distal end of the first bearing 15 and screwed to the handpiece 32 with the bearing 15 between them. The screw ring 82 can be turned freely together with the handpiece 32 within the first bearing 15. An O ring 45 ensures watertightness.

The aforesaid sheath 9 is attached to the distal end of the screw ring 82 by the C ring 69. A watertight state is retained relative to the first bearing 15 by means of a watertightness means such as an O ring 68. In this embodiment, a perfusion/aspiration base 51 is formed on the top of the first bearing 15. When a perfusion/aspiration means that is not shown is connected to the perfusion/aspiration base 51, perfusion or aspiration can be performed using the channel lying through the sheath 9 from the first bearing 15.

The proximal end of the handpiece 32 is inserted in the second bearing 19 and is supported by an O ring 47. The handpiece 32 can be turned if necessary owing to the O ring 45 and O ring 47. The handpiece 32 is freely turnable relative to the manipulating means 34 with a proper turning resistance disabling unexpected turning.

The fixing mechanism for stopping a turn may be realized with, for example, a ball-click mechanism employed in the seventh embodiment or a click mechanism employed in the eighth embodiment.

The ultrasonic transducers 50 for supplying ultrasonic vibrations used to treat a living tissue are, as mentioned above, installed in the form of rings in the handpiece 32. The proximal end of the probe 8 is coupled with the distal end of a drive axis or an axis of ultrasonic vibrations generated by the ultrasonic transducers 50 by tightening a screw.

The second operation member 10 is inserted in the probe 8, and jutting out behind the proximal end of the handpiece 32 through the channel defined by the ultrasonic transducers 50.

For the purpose of preventing leakage of gas attributable to pneumoperitoneum or the like through the channel which is extending to the proximal end of the handpiece 32 and in which the conveying member 10 is inserted, an airtightness member 74 that is shaped substantially like a tube is located near the proximal end of the channel and second operation member 10. The airtightness member 74 is molded using, for example, an elastic member made of rubber or the like or a seal member made of PTFE or the like.

The engaging member 42 is coupled with the proximal end of the second operation member 10 by tightening a screw. The outer circumference of the engaging member 42 is covered with a tube 67 made of an electrically insulating material such as PTFE in order to prevent a high-frequency current from leaking out during a treatment using a high-frequency current which will be described later.

Figure 25A:
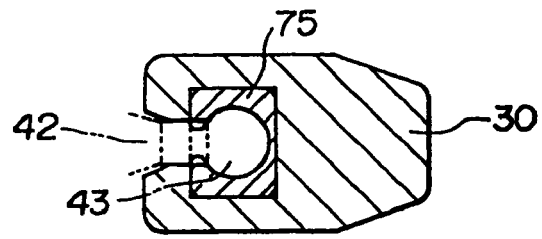
FIG. 25A is a 25A-25A sectional view of FIG. 24.
Figure 25B:
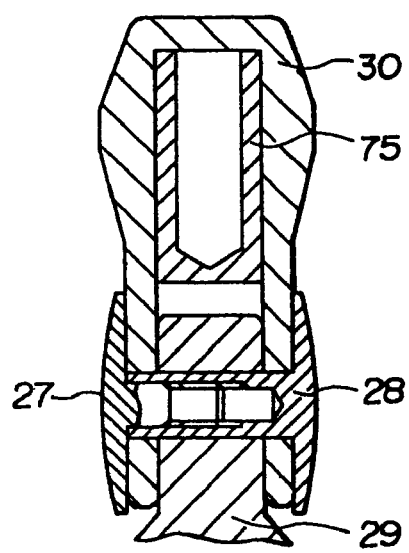
FIG. 25B is a 25B-25B sectional view of FIG. 24.
Figure 25C:
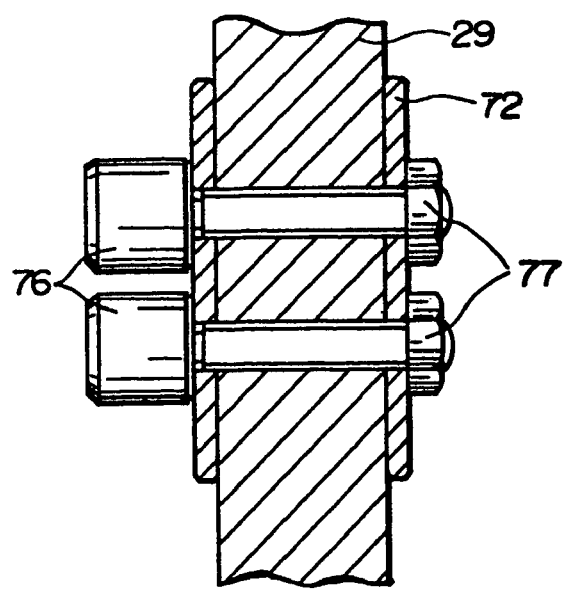
FIG. 25C is a 25C-25C sectional view of FIG. 24.

The spherical section 43 is formed at the proximal end of the engaging member 42. As shown in FIG. 25A, the spherical-section 43 meshes with an engagement receiving member 75 embedded in the upper part of the movable manipulation handle 30. The engagement receiving member 75 has, as shown in FIGS. 25A and 25B, a vertical ditch. The spherical section 43 can slide within the ditch.

The upper opening of the ditch in the engagement receiving member 75 has a width permitting the spherical section 53 to pass through it. The lower opening thereof has a width not permitting the spherical-section to pass through it. The root of the spherical section 53 is enclosed in the lower opening. Normally, the spherical section 53 is fitted in the lower part of the ditch.

Owing to the foregoing structure, when the movable manipulation handle 30 is opened or closed relative to a stationary manipulation handle 29, the engaging member 42 can be driven to advance or withdraw. With the advancement or withdrawal of the engaging member 42, the conveying member 10 and conveying member 5 screwed to the engaging member 42 are driven to advance or withdraw. This causes the movable section 3 to open or close relative to the distal member 7.

The stationary manipulation handle 29 is joined with the proximal end of the supporting member 72 by means of a screw 76 and a nut 77. The movable manipulation handle 30 is, as shown in FIG. 25B, supported by the stationary manipulation handle 29 so that the movable manipulation handle 30 can pivot freely. As mentioned above, the movable manipulation handle 30 can therefore be opened or closed relative to the stationary manipulation handle 29.

Next, an actual example of use of this embodiment will be described.

First, the treatment unit 33 is opposed to a living tissue to be treated. Next, the handpiece 32 is turned relative to the manipulating means 34 so that the orientation of the treatment unit 33 will be matched with a direction convenient for treating the living tissue.

The movable manipulation handle 30 is then moved in an open direction so that the movable section 3 will open. The living tissue to be treated is clamped with an appropriate force. Thereafter, the ultrasonic transducers 50 are driven using a driving power supply, which is not shown, dedicated to the ultrasonic transducers 50. Ultrasonic vibrations are then conveyed to the distal member 7 and movable section 3 and eventually imposed on the living tissue.

At this time, as mentioned above, when a treatment is conducted with the factors set as; a large amplitude of ultrasonic vibrations, a large clamping force, and a long time of imposition of ultrasonic vibrations, it is convenient for incising a living tissue. The reverse setting of the factors is convenient for coagulation. A proper treatment should be conducted in consideration of the situation of a living tissue.

Moreover, when a high-frequency current is applied from a power supply that is not shown into the ultrasonic transducers 50, the high-frequency current can be applied from the ultrasonic transducers 50 to a living tissue via the probe 8, distal cover 6, distal member 7, and movable section 3. A treatment using a high-frequency current can be conducted.

The outer circumference of the engaging member 42 that is exposed is covered with the tube 67 having an electrical insulation ability. Besides, when the movable manipulation handle 30, sheath 9, screw ring 82, bearing 15, handpiece 32, casing, and the like are molded using a material having the electrical insulation ability; such as, PEEK or polysulfone, leakage of a high-frequency current can be prevented. A treatment can therefore be conducted safely.

A treatment by ultrasonic vibrations and a treatment by a high-frequency current can be conducted independently. These treatments may be conducted separately or simultaneously.

Next, the procedure of disassembling or assembling the components of this embodiment will be described.

First, the sheath 9 is pulled out distally from the screw ring 82. Next, the stationary manipulation handle 29 is dismounted downward from the supporting member 72 by removing the screw 76. Accordingly, the movable manipulation handle 30 moves downward. The spherical section 43 fitted in the engagement receiving member 75 comes off from the ditch. This causes the engaging member 42 to fall off the movable manipulation handle 30.

Thus, a united body of the stationary manipulation handle 29 and movable manipulation handle 30 is disassembled from the manipulating means 34.

Next, the screw ring 82 is dismounted from the handpiece 32. Accordingly, the screw ring 82 is disassembled from the bearing 15. Thereafter, the handpiece 32 is pulled out proximally from the bearing 15 and bearing 19. A united body of the handpiece 32, probe 8, and the like is disassembled from the manipulating means 34.

The probe 8 is dismounted from the handpiece 32, and the engaging member 42 is dismounted from the conveying member 10. Thereafter, the distal member 7 is dismounted from the probe 8.

Due to the foregoing disassembling, the ultrasound treatment appliance 31 is brought into a state in which cleaning and sterilization can be achieved successfully. The respective parts can be cleaned and sterilized.

For assembling the components of the ultrasound treatment appliance 31 again, the components are assembled by reversing the aforesaid disassembling procedure.

Moreover, since disassembling and assembling can be achieved as mentioned above, if any part should be broken, the part alone would have to be replaced with a new one. The ultrasound treatment appliance can be reused.

Figure 26:
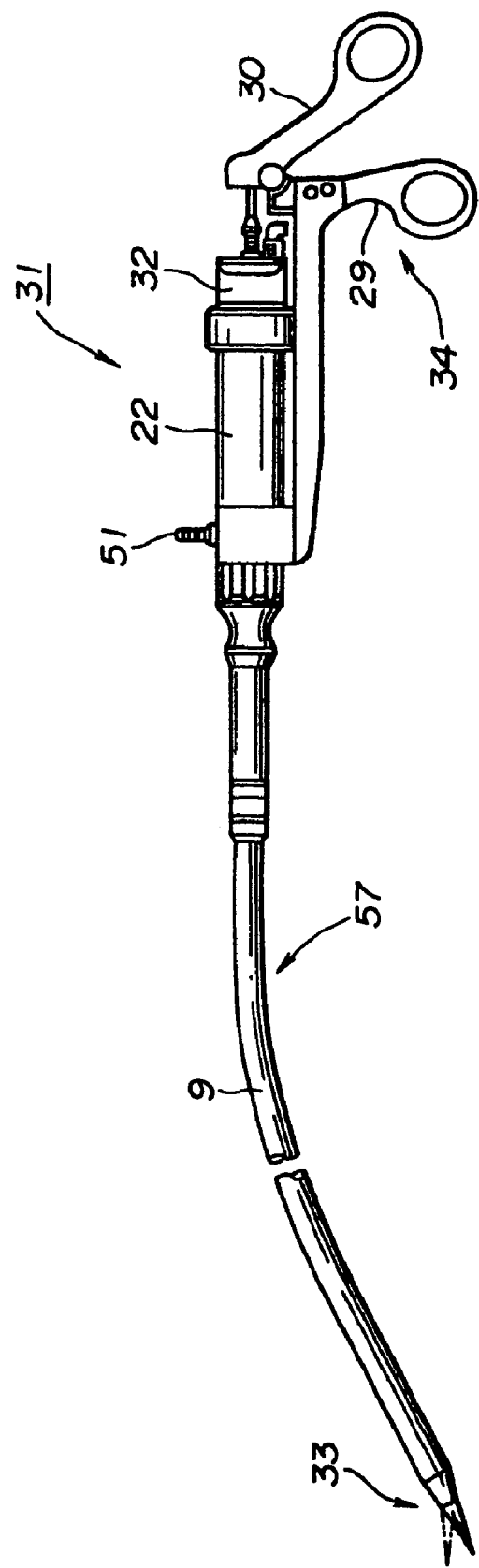
FIG. 26 is a plan view showing an ultrasound treatment appliance of the tenth embodiment of the present invention.

Referring to FIG. 26, the tenth embodiment of the present invention will be described.

FIG. 26 shows the tenth embodiment of the present invention. This embodiment has substantially the same structure as the ninth embodiment. However, the probe 8 is curved, and the sheath 9 and conveying member 10 lying through the sheath 9 are formed with an elastic member. The conveying member 10 is formed, for example, with a super-elastic wire or the like made of an alloy of nickel and titanium. The sheath 9 is molded using a member with plasticity, for example, a member made of PTFE.

The curved probe 8 can therefore be inserted in the sheath 9. Beside, the conveying member 10 can advance or withdraw within the probe 8 when driven.

Owing to the foregoing structure, the treatment unit 33 can be turned relative to the manipulating means 34. At the same time, better maneuverability is ensured.

The other components and operations are identical to those of the ninth embodiment.

Referring to FIGS. 27 to 39, the eleventh embodiment of the present invention will be described.

Figure 27:
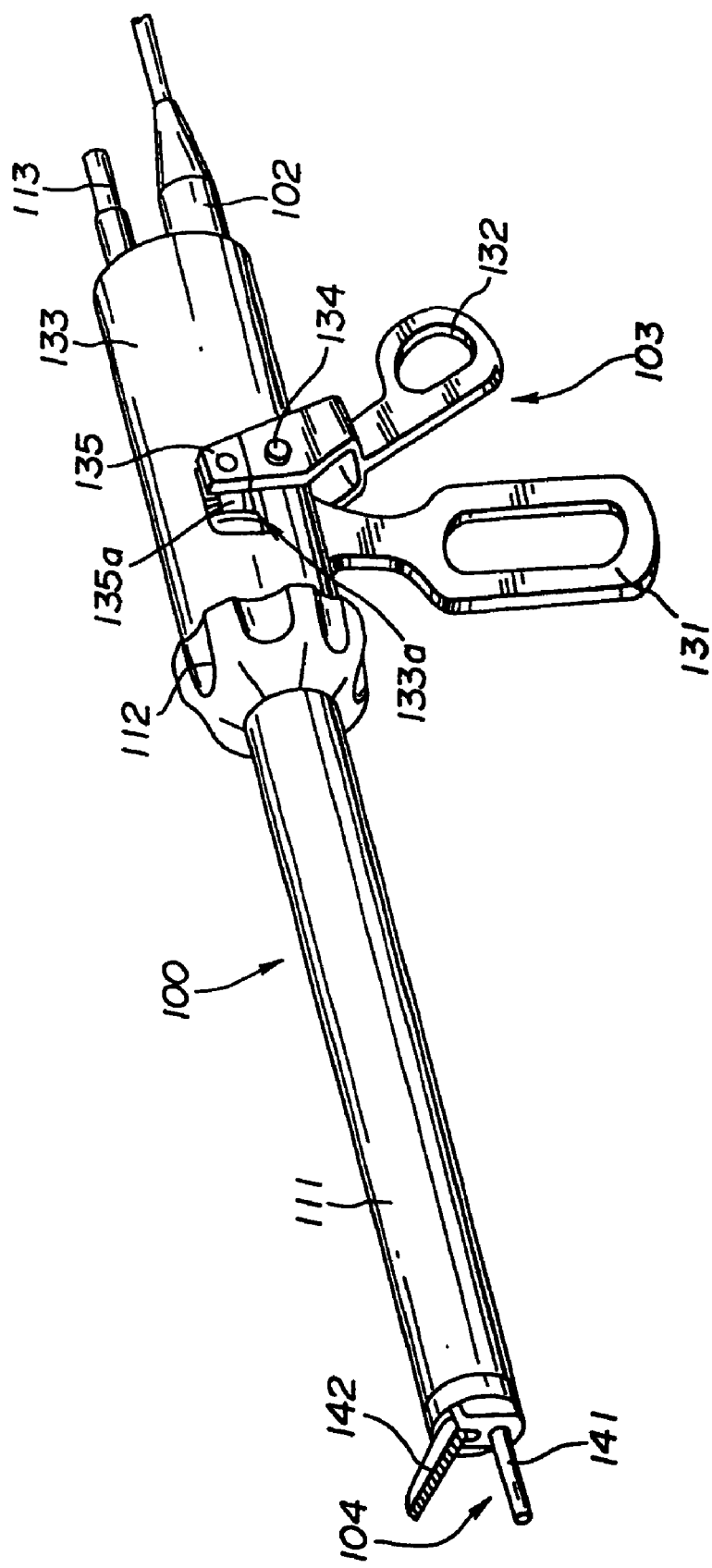

As shown in FIG. 27, an ultrasound treatment appliance 100 comprises: an operation unit 103 including a handpiece 102 in which ultrasonic transducers for generating ultrasonic vibrations is incorporated and having a stationary manipulation handle 131 and a movable manipulation handle 132 serving as an action instructing member; a treatment unit 104 including a distal member 141 that is a stationary section of the treatment unit to which ultrasonic vibrations generated in the handpiece 102 incorporated in the operation unit 103 and used to treat a living tissue are conveyed, and a holding member 142 that is opposed to the distal member 141 and that is a movable section of the treatment unit which clamps or frees a living tissue in cooperation with the distal member 141; and a sheath 111 that is a protective member for covering a vibration conveying member, which will be described later, for conveying vibrations of the handpiece 102 to the distal member 141 of the treatment unit 104 and an operation member, which will be described later, for conveying an action of clamping or freeing made by the movable manipulation handle 132 to the holding member 142.

The stationary manipulation handle 131 of the operation unit 103 is united with a transducer cover 133 that includes the handpiece 102, that is tubular, and that has windows 133a formed on the lateral side thereof. On the other hand, the movable manipulation handle 132 is screwed to the transducer cover 133 so that the movable manipulation handle 132 can pivot freely with respect to a handle supporting-point pin 134. On the movable manipulation handle 132, locks 135 each having a lock pawl 135a that locks a rotor, which will be described later and is inserted in the transducer cover, in the transducer cover so that the rotor will be freely detachable are formed and oriented to a center axis seen through the windows 133a of the transducer cover 133.

A turnable knob 112 is fixed unitedly to the end of the sheath 111 on the side of the operation unit. The turnable knob 112 is used to turn the holding member 142 constituting the treatment unit 104 with respect to the center axis of the distal member 141. Reference numeral 113 denotes an electrode plug to which a fulguration power supply is connected.

Figure 28:
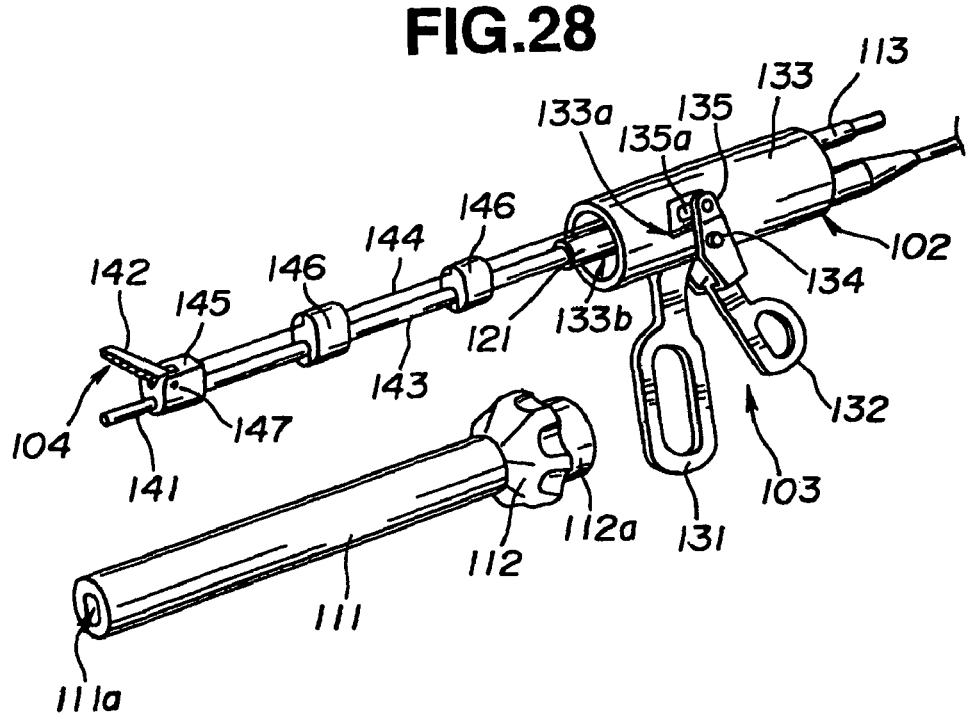

As shown in FIG. 28, the sheath 111 is constructed so that it will be freely detachable from the transducer cover 133 constituting the operation unit 103. By dismounting the sheath 111 from the transducer cover 133, a probe 143 that is a vibration conveying member for conveying vibrations of the handpiece 102 to the distal member 141 and an operation rod 144 that is an operation member for conveying an instruction of an action of clamping or freeing from the movable manipulation handle 132 to the holding member 142 emerge. The sheath 111 has a through bore 111a having a substantially elliptic section. In the through bore 111a, a distal coupler 145 that is a holding member for preventing the probe 143 and operation rod 144 from touching the sheath 111 as well as a plurality of couplers 146 are arranged.

The probe 143 and operation rod 144 are inserted in through bores, which will be described later, formed in the distal coupler 145 and plurality of couplers 146. The distal coupler 145 and plurality of couplers 146 have substantially the same shape as the section of the through bore 111a formed in the sheath 111. The distal coupler 145 and plurality of couplers 146 are arranged unitedly in the through bore 111a because the straight sides of the elliptic section serve as detents. The distal coupler 145 and plurality of couplers 146 turn unitedly in the same direction responsively to the turn of the sheath 111.

The holding member 142 is fixed to the distal coupler 145 so that the holding member 142 can pivot with respect to a pin 147. The distal portion of the operation rod 144 is coupled with the holding member 142. The back end of the operation rod 144 is inserted in an inner hole 133b of the transducer cover 133 and connected to the rotor, which will be described later, locked by the movable manipulation handle 132. When the movable manipulation handle 132 is manipulated toward the stationary manipulation handle, the operation rod 144 withdraws to cause the holding member 142 to move toward the distal member.

The distal member 141 jutting out from the distal coupler 145 is screwed to and detachable from the distal end of the probe 143. The back end of the probe 143 is screwed to and detachable from a horn 121 located at the distal end of the handpiece 102.

Figure 29:
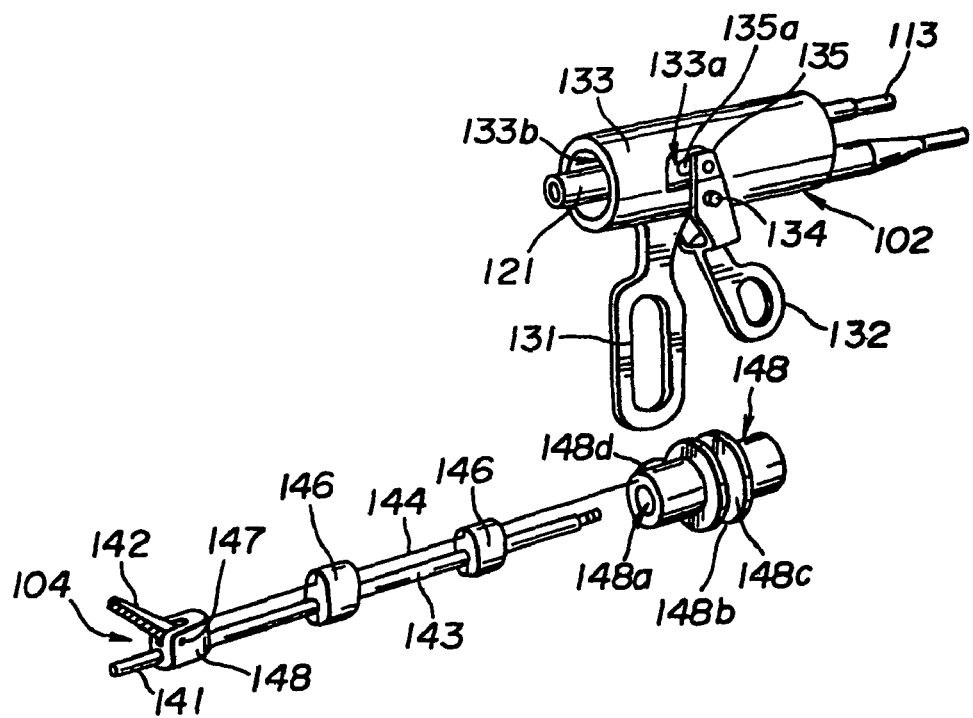

As shown in FIG. 29, the probe 143 coupled with the distal member 141 and the operation rod 144 coupled with the holding member 142 are detachable from the operation unit 103.

Since the back end of the probe 143 is screwed to the distal end of the horn 121 located at the distal end of the handpiece 102, the probe 143 can be readily dismounted from the operation unit 103 by unscrewing it from the horn. When the probe 143 is connected to the horn 121 placed in the operation unit 103, the connection can be achieved readily by screwing.

On the other hand, the back end of the operation rod 144 is connected to a rotor 148 serving as a connecting means. The rotor 148 is freely detachable from the operation unit 103. The rotor 148 is a tubular member having a through hole 148a in which the horn 121 is inserted. A convex part 148b that slides in the inner hole 133b of the transducer cover 133 is formed in the center of the rotor 148. A ditch 148c serving as a connecting means in which the lock pawls 135b of the locks 135 formed on the movable manipulation handle 132 are fitted is formed in the convex part 148b.

Figure 30:
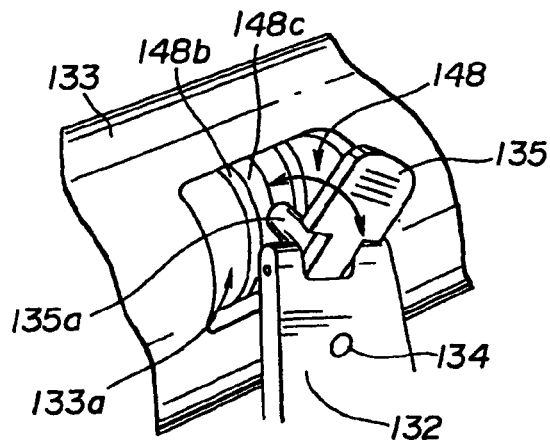

The rotor 148 inserted in the inner hole 133b of the transducer cover 133 can therefore be readily dismounted by, as shown in FIG. 30, removing the lock pawls 135a formed on the locks 135 of the movable manipulation handle 132 and fitted in the ditch 138c of the rotor 148 inserted in the inner hole 133b of the transducer cover 133.

For connecting the rotor 148 to the transducer cover 133 constituting the operation unit 103, first, the rotor 148 to which the back end of the operation rod 144 is connected is inserted in the through hole 133b of the transducer cover 133 with the convex part 148b of the rotor 148 facing the wall of the through hole 133b. Next, as shown in FIG. 30, the ditch 148c dug in the convex part 148b is opposed to the windows 133a of the transducer cover 133. The locks 135 that can freely be nodded and are attached to the movable manipulation handle 132 are then nodded, whereby the lock pawls 135a of the locks 135 are fitted in the ditch 148c. Consequently, the rotor 148 is locked in the inner hole 133b of the transducer cover 133 constituting the operation unit 103 so that the rotor 148 can freely slide in the longitudinal direction and circumferential direction of the inner hole 133b.

A convex part 148d is formed as a detent on the distal portion of the rotor 148. In an assembled state, the convex part 148d is fitted in an engagement ditch formed in the inner circumference, which is not shown, of an engagement part 112a serving as the proximal portion of the turnable knob 112. When the convex part 148d of the rotor 148 is unitedly engaged with the turnable knob 112, the rotor 148 is turned responsively to the turn of the turnable knob 112.

Figure 31:
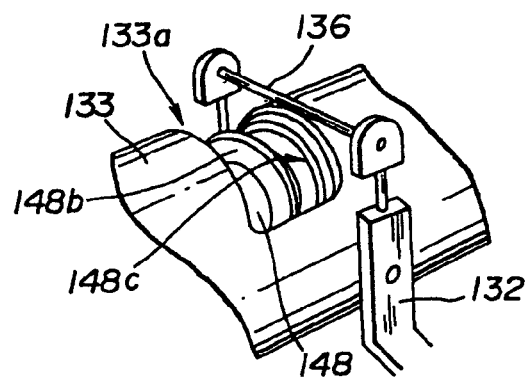
Figure 32A:
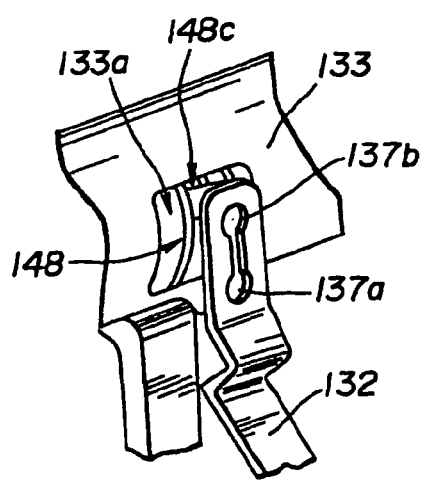
FIG. 32A is a view showing a stage before the rotor is locked in the operation unit.
Figure 32B:
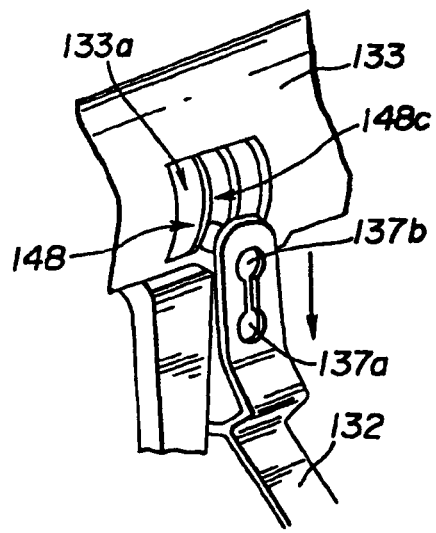
FIG. 32B is a view showing a state in which the rotor is locked in the operation unit.

As for a connecting method for locking the rotor 148 in the inner hole 133b of the transducer cover 133 so that the rotor 148 can freely slide in the longitudinal direction and circumferential direction of the inner hole 133b, as shown in FIG. 31, the ditch 148c of the rotor 148 may be opposed to the window 133a formed in the top of the transducer cover 133, and a lock bar 136 that is freely movable vertically may be moved downward and fitted in the ditch 148c. Alternatively, as shown in FIGS. 32A and 32B, the movable manipulation handle 132 may be provided with the lock pawls 135a, lock holes 137a, and detachment holes 137b. A transition is made from a state in which the handle supporting-point pin 134 is inserted in the detachment holes 137b of the movable manipulation handle 132 to a state in which the handle supporting-point pin 134 is inserted in the lock holes 137a of the movable manipulation handle 132, whereby the lock pawls 135a are fitted in the ditch 148c. Thus, various forms are conceivable.

Figure 33:
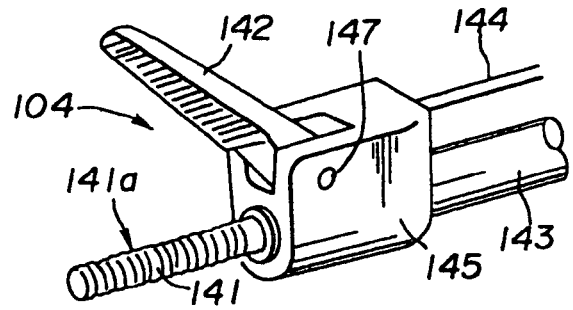

As shown in FIG. 33, the distal member 141 jutting out from the distal coupler 145 is a cylindrical member made of titanium or aluminum that exerts a high sound effect and that is well-adaptable to a living body, or an alloy of titanium and aluminum. A thread-like irregular section 141a is formed by finishing the surface of the distal member 141 in order to increase the contact area for a living tissue to be clamped in cooperation with the holding member 142. By making the pitch of the irregular section 141a finer for the amplitude of ultrasonic vibrations, a coefficient of friction occurring between the holding member 142 and a living tissue due to the vibrations of the holding member 142 can be increased. Moreover, coagulation efficiency can be further improved. The distal end of the irregular section 141a and the distal end of the holding member 141 are chamfered for fear the distal ends may injure a living tissue.

Figure 34A:
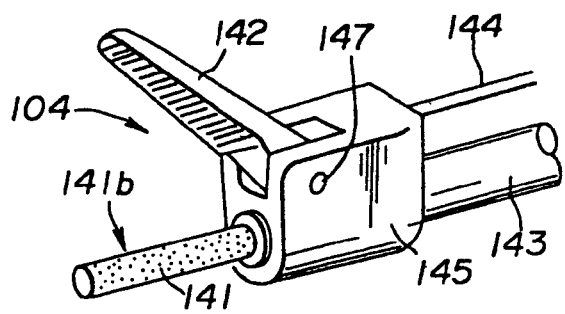
FIG. 34A is a view for explaining another example of finishing the surface of the distal member constituting the treatment unit.
Figure 34B:
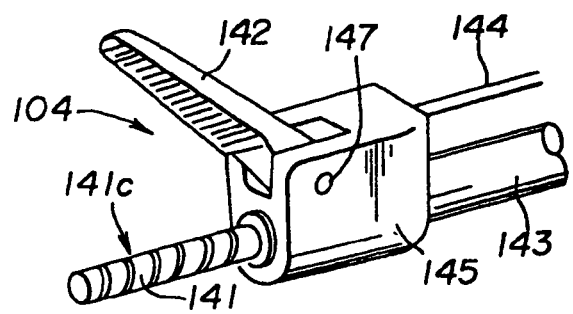
FIG. 34B is a view for explaining another example of finishing the surface of the distal member constituting the treatment unit.

The finishing performed to increase the contact area of the surface of the distal member 141 for a living tissue is not confined to the thread-like irregular section 141a. Alternatively, the finishing may be performed to create a satin surface 141b shown in FIG. 34A or to create a plurality of thin ditches 141c circumferentially as shown in FIG. 34B. Even when the thin ditches 141c are created on the distal member 141, the distal end of the distal member is chamfered. A living tissue will therefore not be injured.

Figure 35:
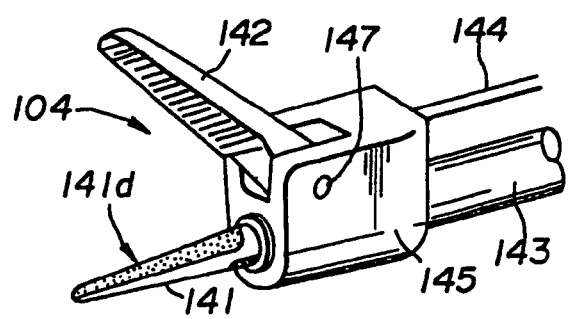

Moreover, a tapered side 141d shown in FIG. 35 may be created on the distal member 141 that used to be cylindrical in order to upgrade the effect of ultrasonic vibrations. At this time, the finishing to be performed on the distal member 141 is confined to the side of the distal member 141 facing the holding member 142.

Figure 36A:
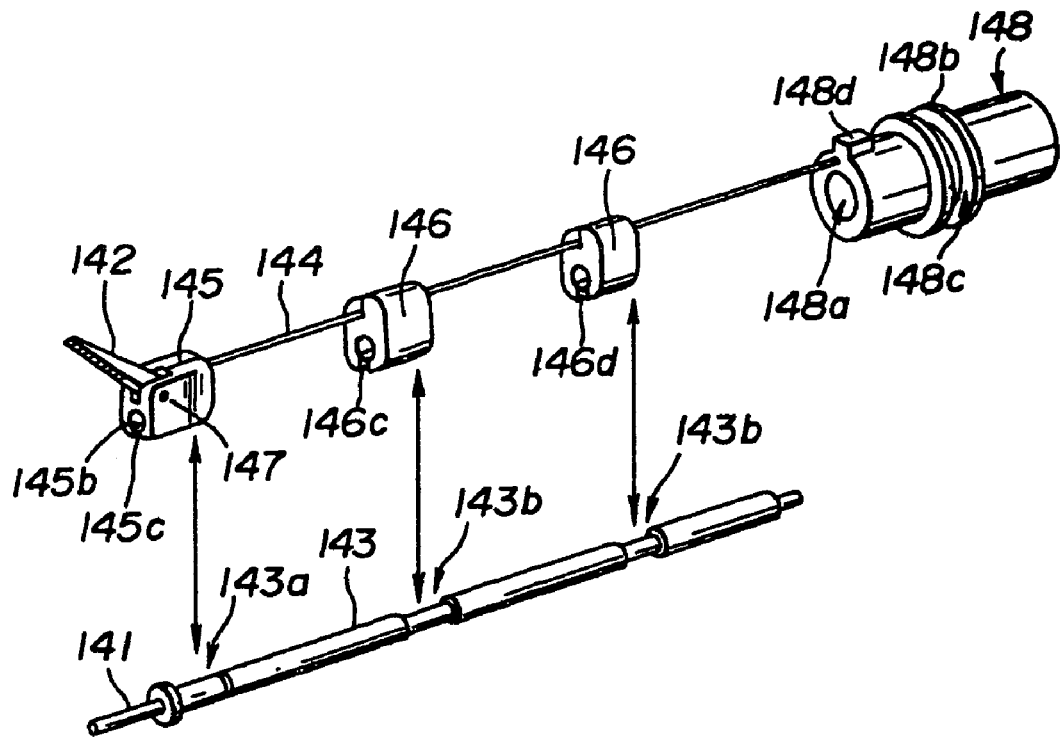
FIG. 36A is a view for explaining a structure of coupling coupling members with a vibration conveying rod.
Figure 36B:
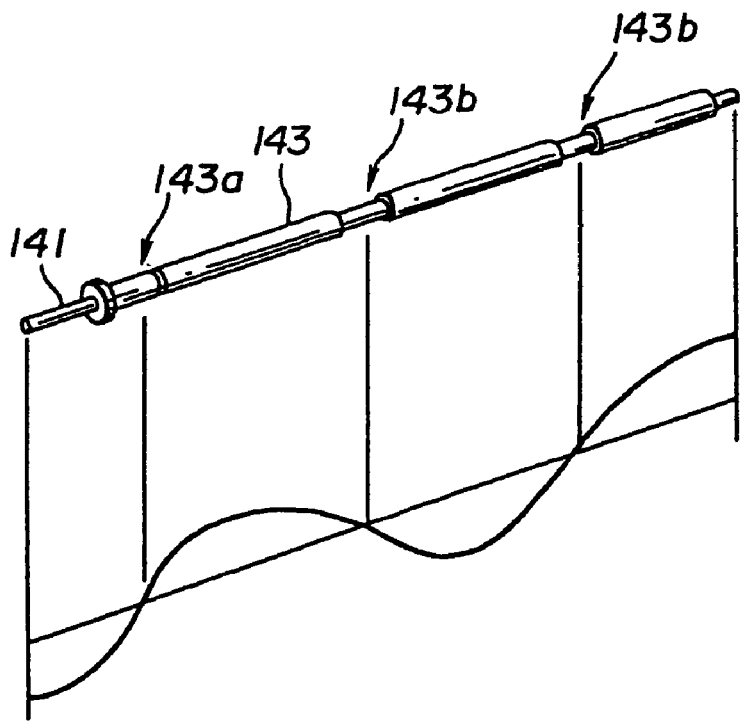
FIG. 36B is a view for explaining the positions of ditches on the vibration conveying rod.
Figure 37:
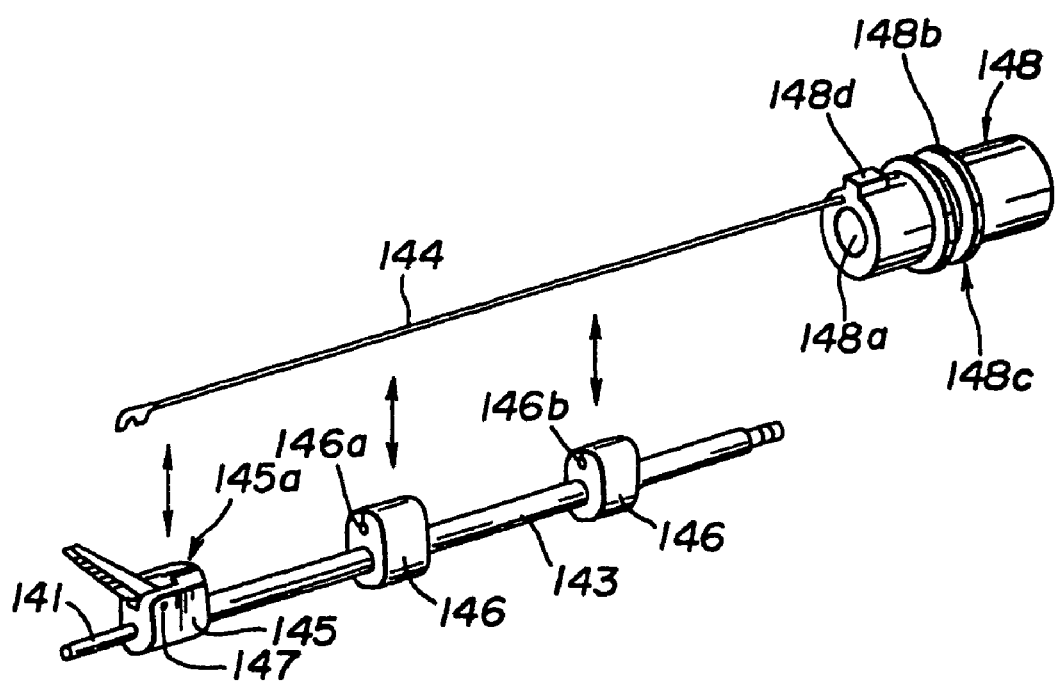

As shown in FIGS. 36A to 37, the probe 143 and operation rod 144 are constructed to be detachable from the distal coupler 145 and plurality of couplers 146. The distal coupler 145 has a ditch 145a, in which the holding member 142 and operation rod 144 are placed, a through hole 145b in which the distal member 141 and probe 143 are placed, and a detachment slit 145c. The couplers 146 have a thin hole 146a in which the operation rod 144 is inserted, a detachment slit 146b, a through hole 146c in which the probe 143 is inserted, and a detachment slit 146d. The distal coupler 145 and couplers 146 from which the probe 143 and operation rod 144 are freely detachable are made of a fluorocarbon resin material that improves sliding efficiency; such as Teflon (polytetrafluoroethylene).

As shown in FIG. 36A, the distal coupler 145 and couplers 146 are placed in ditches 143a and 143b formed at given positions on the probe 143. As shown in FIG. 36B, the ditches 143a and 143b on the probe 143 are formed at nodes of an oscillatory wave in order to avoid the influence of vibrations stemming from the ultrasonic transducers. On the other hand, junctions at which the probe 143 is screwed to the distal member 141 and horn 121 are located at antinodes of the oscillatory wave on which the stress attributable to vibrations does not concentrate.

As shown in FIGS. 38A and 38B, male screws 143c and 143d are formed at both ends of the probe 143. The male screws 143c and 143d are engaged with female screws (not shown) formed in the distal member 141 and horn 121 respectively. Thus, vibrations stemming from the ultrasonic transducers are conveyed to the distal member 141 by way of the horn 121 and probe 143.

The members for conveying vibrations generated by the ultrasonic transducers are made of titanium or aluminum that exerts a high sound effect and that is well-adaptable to a living body, or an alloy of titanium and aluminium. Titanium hardly distorts due to a break, is resistive to a break, and well-adaptable to a living body. For these reasons, titanium is regarded optimal. However, titanium is hard to machine and is expensive. By contrast, aluminium is relatively easy to machine and inexpensive. However, there is a problem concerning strength; that is, aluminum is susceptible to heat generated due to vibrations.

When the ultrasound treatment appliance is used as a disposable appliance, the horn 121, probe 143, and distal member 141 may be formed with aluminum members. When priority is given to a treatment such as incision or coagulation, at least the distal member 141 should preferably be made of titanium. When the ultrasound treatment appliance 100 is constructed so that the components can be disassembled and assembled, it is preferred that titanium offering great strength and durability is used. In this case, the ultrasound treatment appliance 100 becomes expensive.

In this embodiment, the distal member 141 constituting the treatment unit and the horn 121 for supplying ultrasonic vibrations stemming from the ultrasonic transducers to the probe 143 are made of titanium offering high durability. The probe 143 serving as a relay member linking the horn 121 and distal member 141 is made of inexpensive aluminum.

As shown in FIG. 38C, female screws 143e and 143f may be formed in both end portions of the probe 143. In this case, a male screw 141a associated with the female screw 143e of the probe 143 is formed on the distal member 141, and a male screw 121a associated with the female screw 143f of the probe 143 is formed on the horn 121.

Figure 39A:
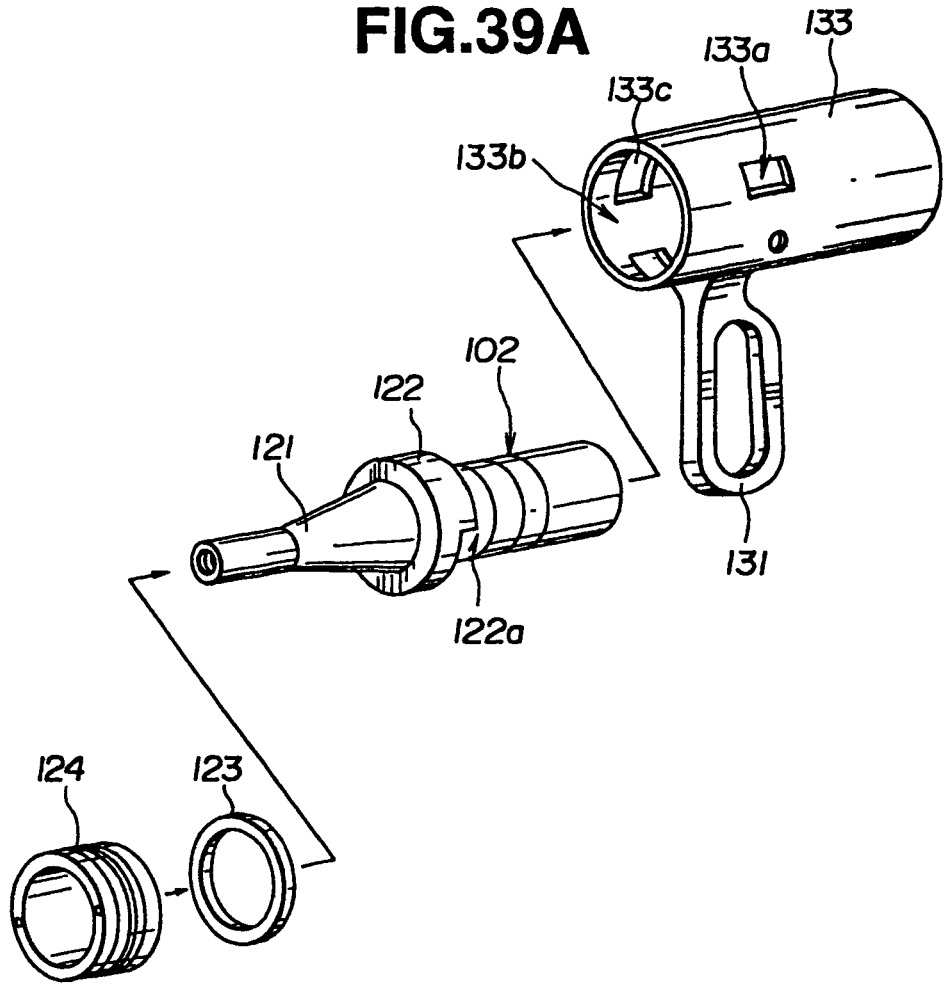
FIG. 39A is a view showing a structure in which a transducer unit and a transducer cover constituting an operation unit are separate bodies.

Moreover, as shown in FIG. 39A, the handpiece 102 is placed in the through hole 133b of the transducer cover 133. At this time, the handpiece 102 must be placed stably at a given position in the through hole 133b. A positioning section 133c is therefore formed in the through hole. A positioning notch 122a is formed on a flange 122 of the handpiece 102. When inserted in the through hole 133b of the transducer cover 133, the handpiece 102 is fixed stably at the given position by a fixture 124 via a packing 128 such as an O ring.

Figure 39B:
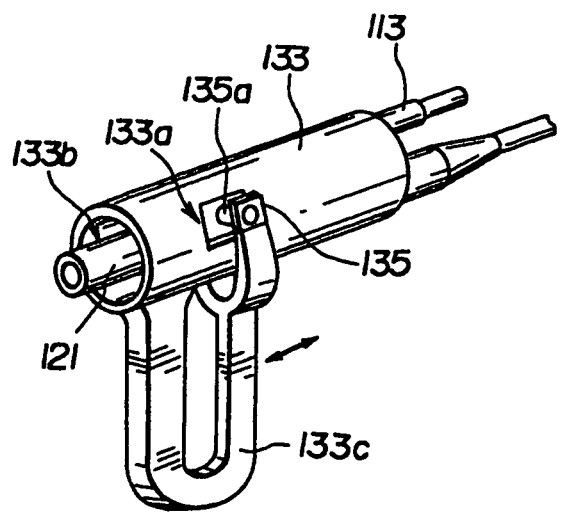
FIG. 39B is a view showing a structure in which the transducer unit and transducer cover constituting the operation unit are united.

Moreover, as shown in FIG. 39B, a manipulation handle 133c into which a stationary manipulation handle and a movable manipulation handle are integrated may be attached to the transducer cover 133.

A treatment to be conducted by inserting the ultrasound treatment appliance 100 having the foregoing structure into the abdominal cavity will be described.

First, the movable manipulation handle 132 constituting the operation unit 103 of the ultrasound treatment appliance 100 is manipulated toward the stationary manipulation handle in order to clamp a living tissue to be treated by the distal member 141 and holding member 142. The rotor 148 locked in the through hole of the transducer cover 133 by the lock pawls 135a formed on the movable manipulation handle 132 then withdraws in the through hole. This causes the operation rod 144 connected to the rotor 148 to withdraw in the same manner. The holding member 142 then moves toward the distal member. Thus, the living, tissue is clamped by the distal member 141 and holding member 142.

Next, in the above state, the ultrasonic transducers, which are not shown, incorporated in the handpiece 102 are driven using a ultrasonic transducer driving power supply in order to generate ultrasonic waves. Ultrasonic vibrations generated in the handpiece 102 are conveyed to the distal member 141 by way of the horn 121 and probe 143. When the ultrasonic vibrations are conveyed to the distal member 141, the distal member 141 vibrates. The vibrations are conveyed to the clamped living tissue through the thread-like irregular section 141a formed by finishing the surface of the distal member 141. Frictional heat then develops to coagulate the living tissue. While ultrasonic vibrations are being imposed on a living tissue, if a clamping force used to clamp the living tissue is increased by manipulating the movable manipulation handle 132 further toward the stationary manipulation handle, the holding member 142 approaches the distal member 141. Consequently, incision is completed without bleeding from the living tissue.

Thereafter, the treatment unit 104 is moved to a region in which another living tissue to be treated is present. At this time, the positional relationship between the operation unit 103 and treatment unit 104 is changed from the one set during the previous treatment. The turnable knob 112 is therefore turned in order to improve workability. The sheath 111 to which the turnable knob 112 is secured is turned together with the rotor 148 locked in the through hole of the transducer cover 133.

When the sheath 111 turns, the distal coupler 145 and couplers 146 placed in the through hole 111a of the sheath 111 are turned with respect to the center axes of the distal member 141 and probe 143. When the holding member 142 reaches a desired position, the turnable knob 112 is stopped turning. In order to clamp a living tissue to be treated by the distal member 141 and holding member 142, the movable manipulation handle 132 constituting the operation unit 103 of the ultrasound treatment appliance 100 is manipulated toward the stationary manipulation handle. Thus, the living tissue is clamped and treated.

As mentioned above, the distal member constituting the treatment unit is shaped like a round bar. The surface of the round bar is finished in order to increase the contact area for a living tissue. Consequently, frictional heat develops efficiently in the living tissue owing to ultrasonic vibrations conveyed from the ultrasonic transducers to the distal member. A treatment such as coagulation or incision can therefore be conducted smoothly.

A detent is formed on each of the outlines of the distal coupler and plurality of couplers in which the probe and operation rod are placed. The distal coupler and couplers are therefore unitedly placed in the inner hole of the sheath. Besides, the rotor is united with the turnable knob. The distal coupler, plurality of couplers, and rotor are therefore turned in the same direction responsively to the turn of the sheath made by manipulating the turnable knob. The holding member can therefore be turned to a desired position with respect to the center axis of the distal member. Consequently, the positional relationship between the operation unit and treatment unit can be modified without the necessity of turning the operation unit in which the ultrasonic transducers are incorporated. Eventually, not only the operator workability improves greatly but also a cord extending from the operation unit will not tangle.

Next, the procedure of disassembling or assembling the components of this embodiment will be described.

First, the sheath 111 is dismounted, as shown in FIG. 28, from the ultrasound treatment appliance 100 shown in FIG. 27 in an assembled state. The sheath 111 thus becomes a separate body. The probe 143, operation rod 144, and treatment unit 104 mounted in the distal coupler 145 and plurality of couplers 146 placed in the inner hole 111a of the sheath 111 emerge.

Next, the probe 143 and horn 121 are unscrewed and freed from each other. The rotor 148 locked in the operation unit 103 is dismounted. At this time, the locks 135 formed on the movable manipulation handle 132 fixed to the transducer cover 133 of the operation unit 103 at a supporting point are swayed backward. This causes the lock pawls 135a to become free from the ditch 148c of the rotor 148 inserted in the transducer cover. The rotor 148 is then, as shown in FIG. 28, pulled out. The operation unit 103 is now a separate body.

Thereafter, as shown in FIGS. 36A and 37, the probe 143 and operation rod 144 are dismounted from the distal coupler 145 and plurality of couplers 146.

Thereafter, the probe 143 and distal member 141 are unscrewed from each other. The distal member 141 is then detached from the probe 143. When the pin 147 is pulled out of the distal coupler 145, the holding member 142 is dismounted from the distal coupler 145.

The series of operations brings the ultrasound treatment appliance 100 into a state in which the respective components can be fully cleaned and sterilized. If necessary, the movable manipulation handle 132 constituting the operation unit 103 may be dismounted and then the handpiece 102 may be dismounted.

After the disassembled components are cleaned and sterilized, when the components are assembled again, the foregoing procedure of disassembling is reversed. Thus, the ultrasound treatment appliance 100 can be reconstructed.

As mentioned above, the structure enables disassembling and assembling. The disassembled components can be fully or reliably cleaned and sterilized without labor. If any member should be broken, the broken member alone would have to be replaced with a new one. Thus, the ultrasound treatment appliance can be used continually and economically.

Moreover, the distal member constituting the treatment unit, and the horn for supplying ultrasonic vibrations stemming from the ultrasonic transducers to the probe are made of highly-durable titanium. The probe serving as a relay member linking the horn and distal member is made of inexpensive aluminum. Thus, the ultrasound treatment appliance capable of conveying ultrasonic vibrations stemming from the ultrasonic transducers to the distal member without deteriorating the performance of a treatment such as incision or coagulation can be provided inexpensively.

Furthermore, when the distal member to be screwed to the distal end of the probe is replaced with another one having a shape, size, and finished surface optimal to a treatment, the treatment can be conducted efficiently.

Furthermore, the rotor to be locked in the operation unit may be provided with a convex part and each of the locks may be provided with a concave part. Even in this case, the same operations and advantages as those mentioned above are available.

Referring to FIGS. 40 to 43, the twelfth embodiment of the present invention will be described.

Figure 40:
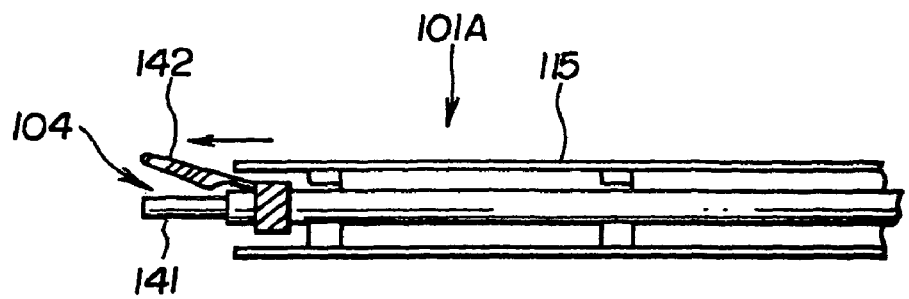
FIGS. 40 to 43 are views for explaining the twelfth embodiment of the present invention.
Figure 41:
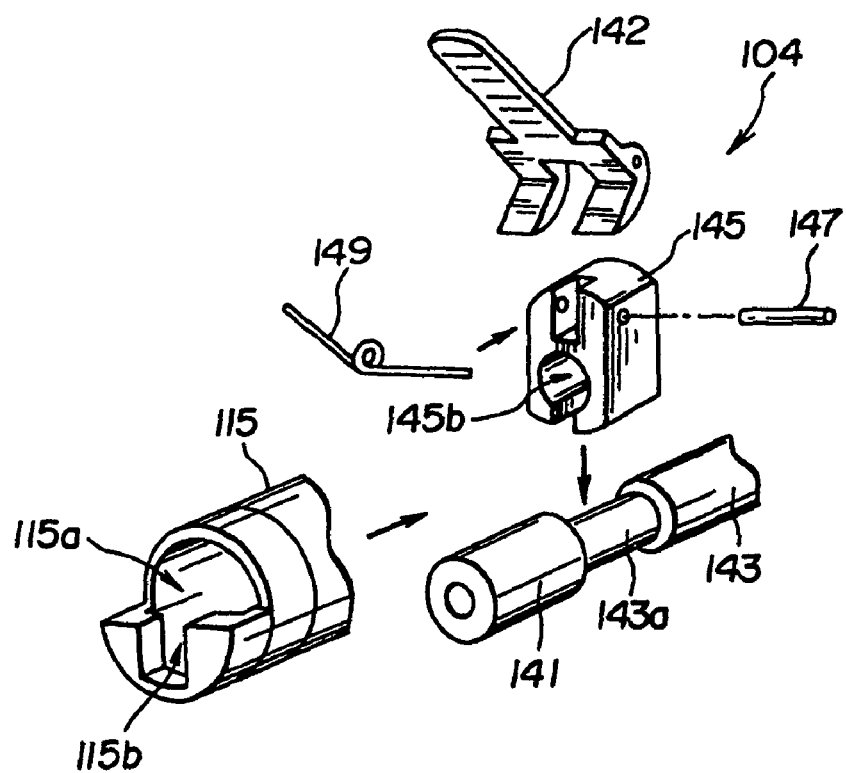

In FIG. 40, unlike the aforesaid embodiment, a clamp unit 104 composed of a holding member 142a and a distal member 141 is manipulated for clamping or freeing by advancing or withdrawing a sheath 115 without using an operation rod 144. In this case, an ultrasound treatment appliance 101A is constructed by forming the clamp unit 104 as shown in FIG. 41. The same operations and advantages as those provided by the aforesaid embodiment can be provided.

Specifically, as shown in FIG. 41, for structuring the clamp unit 104 as shown in FIG. 41, first, the holding member 142a is attached to a distal coupler 145 so that the holding member 142a can pivot with respect to a pin 147. At this time, a torsion coil spring 149 for constraining the holding member 142a to go in an open direction is mounted. Next, a through hole 145b formed in the distal coupler 145 to which the holding member 142a and torsion coil spring 149 are attached is matched with a ditch 143a of a probe 143. Thus, the clamp unit 104 is structured.

The clamp unit 104 is inserted in a through hole 115a of the sheath 115. At this time, the distal coupler 145 formed at the distal end of the sheath 115 is fitted in an engagement ditch 115b that serves as a detect and that is used to unite the distal coupler 145 with the sheath 115. The ultrasound treatment appliance 101A is thus constructed. The ultrasound treatment appliance 101A can therefore achieve clamping and freeing using the distal member 141 and holding member 142 by advancing or withdrawing the sheath 115.

Figure 42:
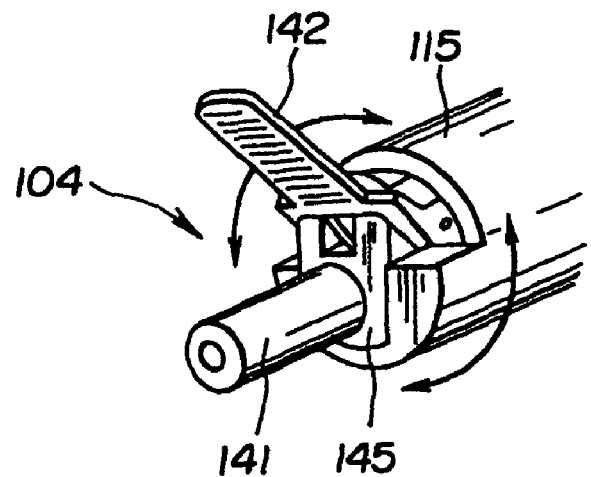

Furthermore, when the sheath 115 is turned as shown in FIG. 42, the distal coupler 145 turns in the same direction responsively to the turn of the sheath 115. Thus, the holding member 142a can be set to a desired position with respect to the center axis of the distal member 141.

Figure 43:
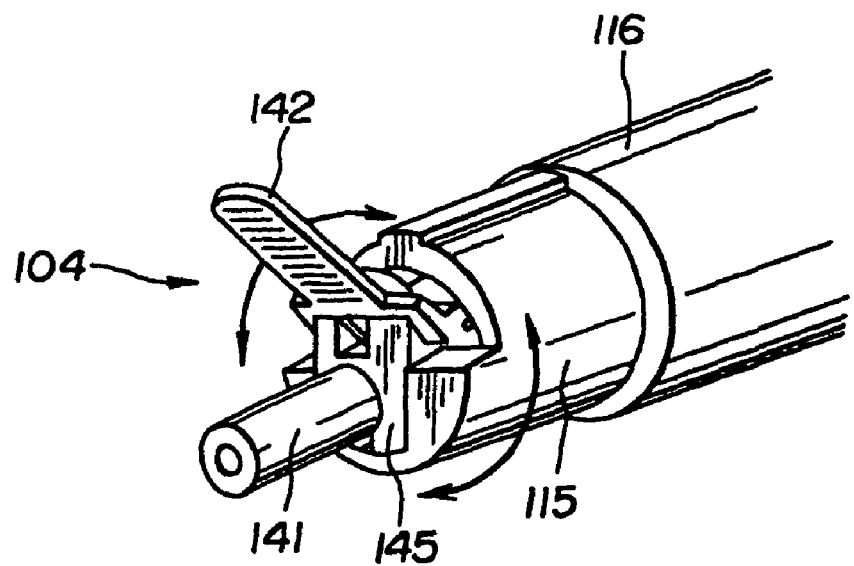

When the sheath 115 is, as shown in FIG. 43, covered with a protective tube 116 or the like, a detent 117 composed of a concave part and a convex part as illustrated may be formed so that the protective tube 116 and sheath 115 can turn unitedly. Thus, the sheath 115 and distal coupler 145 turn in the same direction responsively to the turn of the protective tube 116. Eventually, the holding member 142a can be set to a desired position with respect to the center axis of the distal member 141.

Figure 44:
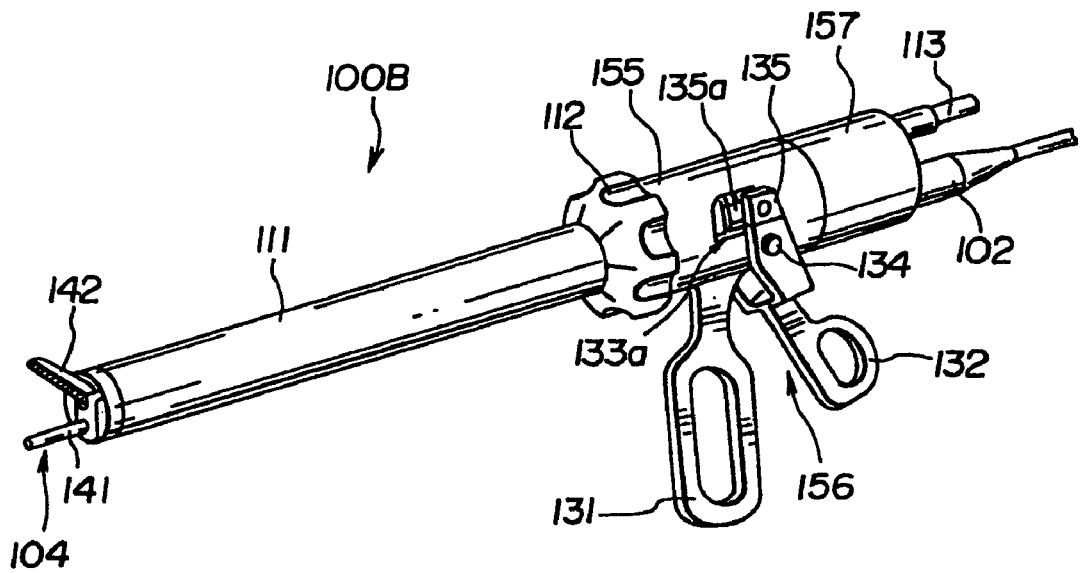
Figure 45:
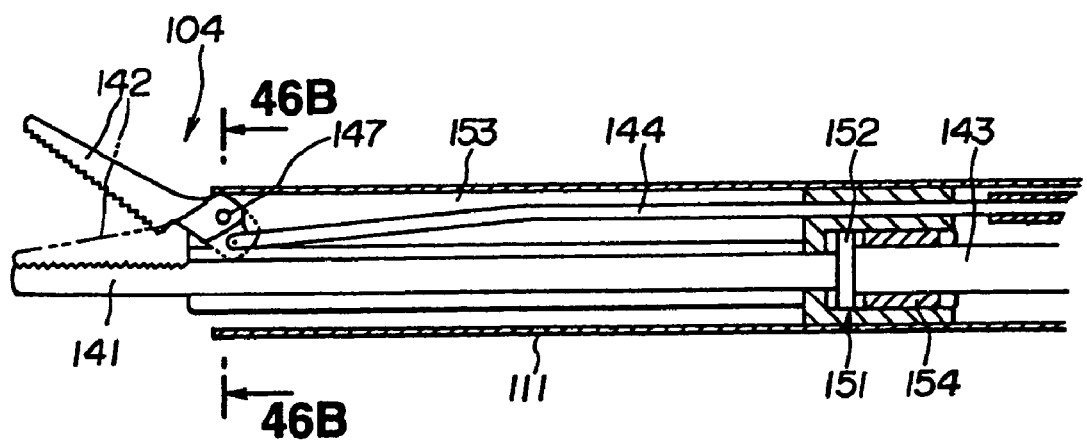

Referring to FIGS. 44 to 46, the thirteenth embodiment of the present invention will be described.

An ultrasound treatment appliance 100B of this embodiment has a structure basically resembling the structure of that of the eleventh embodiment. As shown in FIG. 44, in the ultrasound treatment appliance 101B, the transducer cover 133 of the ultrasound treatment appliance 100 of the eleventh embodiment is divided into two parts; an adaptor 155 serving as a frontal part and a transducer cover 157 serving as a rear part for covering internal transducers.

A turnable knob 112 located in the vicinity of the back end of a sheath 111 is screwed to the front end of the adaptor 155 so that the turnable knob 112 will be freely detachable. The front end of the transducer cover 157 is screwed to the back end of the adaptor 155 so that the transducer cover 157 will be freely detachable.

A stationary operation unit 131 is united with the adaptor 155. Locks 135 located near the top edges of a movable manipulation handle 132, which is attached so that the movable manipulation handle 132 can pivot with respect to a handle supporting-point pin 134, have lock pawls 135a. The lock pawls 135a are fitted in the ditch of a rotor placed inside through windows 133a formed at opposite positions on the lateral side of the adaptor 155. The adaptor 155 and stationary and movable manipulation handles 131 and 132 constitute an operation unit 156.

Similarly to the eleventh embodiment, the rotor is mounted outside a horn whose back end is connected to transducers so that the rotor can move back and forth freely. By manipulating the movable manipulation handle 133, the rotor is moved back and forth. Thus, a holding member 142 is opened or closed via an operation rod whose back end is fixed to the distal end of the rotor. The horn lies through the adaptor 155 and is connected to the transducers within the transducer cover 133 connected to the back end of the horn. The back end of a probe 143 is connected to the distal end of the horn using a screw so that the probe 143 will be freely detachable.

Moreover, as shown in FIG. 45, the front and back of a flange 152 located at a position nearest to the distal end of the probe 143 and coincident with an antinode of vibrations are sandwiched and fixed by a distal coupler 153, with which the holding member 142 is coupled so that the holding member 142 can pivot, and a tightening ring 154. At the time of sandwiching the flange 152, an elastic member such as a packing for preventing the vibrations of the flange 152 from traveling to the distal coupler 153 and tightening ring 154 may be placed intermediately.

Figure 46A:
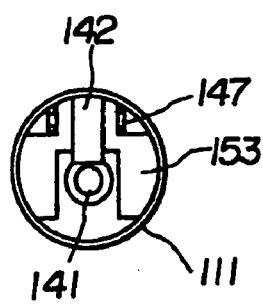
FIG. 46A is a view showing the structure of FIG. 45 from the front thereof.
Figure 46B:
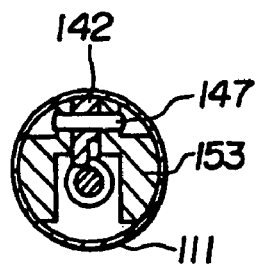
FIG. 46B is a 46B-46B sectional view of FIG. 45.

As shown in FIGS. 46A and 46B, the holding member 142 constituting a treatment unit 104 is supported by a pin 147 at an upper position of a distal member 141 in the vicinity of the distal end of the distal coupler 153 so that the holding member 142 can pivot freely. The distal end of an operation rod 144 is coupled with the distal coupler 153 at a position near the distal end of the distal coupler 153.

As mentioned above, an effort is made so that the prove 143 will not make a relative turn in relation to the sheath 111. The transducers with which the probe 143 is coupled via the horn are unitedly connected to the transducer cover 157 and thus structured so that the transducers will not turn relative to the transducer cover. In short, the probe 143 itself has the same structure as that in the first embodiment, thought it has a different outline.

The operation unit 156 including the adaptor 155 is connected directly to a unit composed of the probe, sheath 111, and transducer cover via the lock pawls 135a, and coupled with the transducer cover 157 and turnable knob 112 by way of coupling means located at both ends of the adaptor 155.

This embodiment exerts such an operation that: when the turnable knob 112 is turned, the transducer cover 157, sheath 111, holding member 142, and distal member 141 are turned relative to the operation unit 156. This embodiment has substantially the same advantages as the other embodiments.

In the aforesaid embodiments, it is apparent that in a structure in which disassembling and assembling are enabled by engaging or attaching, for example, a screw with or to a screw hole or a male screw with or to a female screw, a member having the screw or male screw may be exchanged for a member having the screw hole or female screw. The same applies to the engagement or fitting of a jut, pawl, pin, or the like with or in a concave part, ditch, or the like.

Embodiments formed by combining some of the constituent features of the aforesaid embodiments also belong to the present invention.

As mentioned above, as long as the gist of the present invention that the sheath of an insertion unit for inserting a treatment unit of an ultrasound treatment appliance, which is used to treat a living tissue, is made turnable relative to a manipulating means is conformed with, any other structure may have any purport. No restriction is placed on the contents of a purport.

Figure 47:
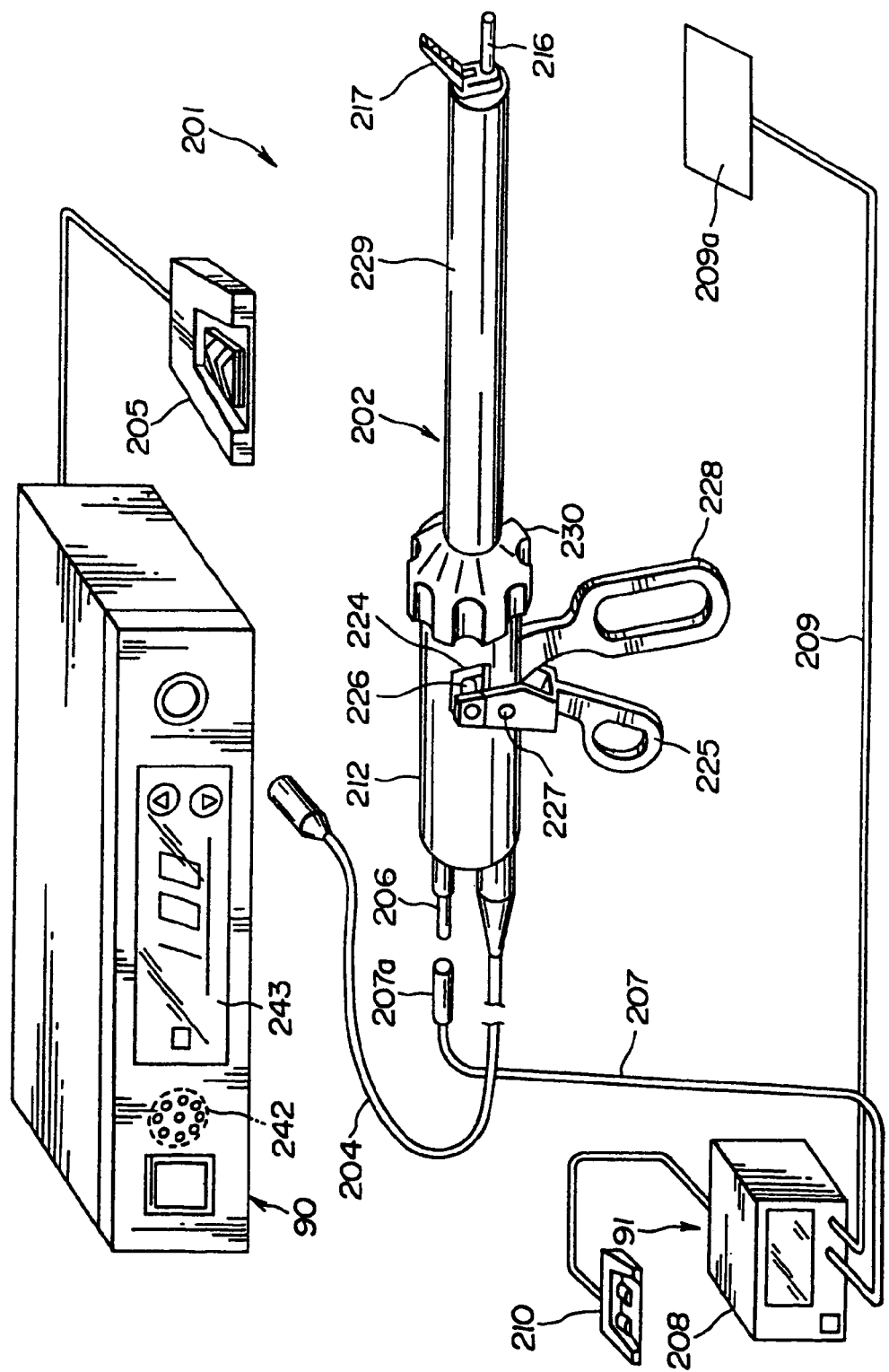
FIGS. 47 to 49 are explanatory diagrams showing the fourteenth embodiment of the present invention.
Figure 48:
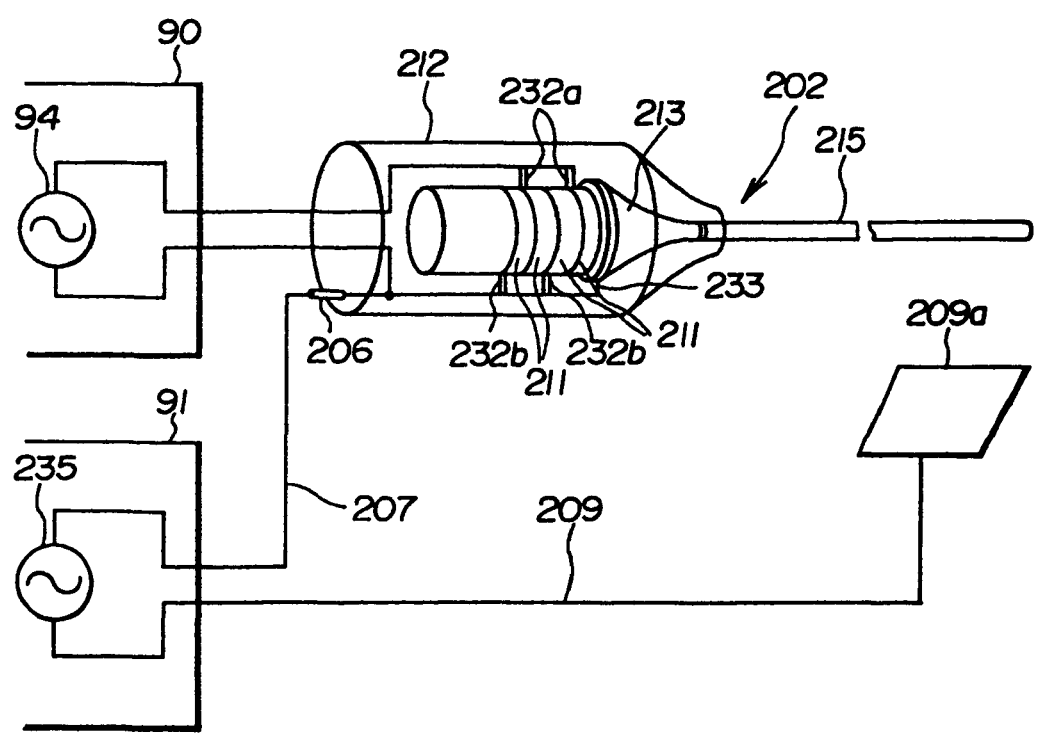
Figure 49:
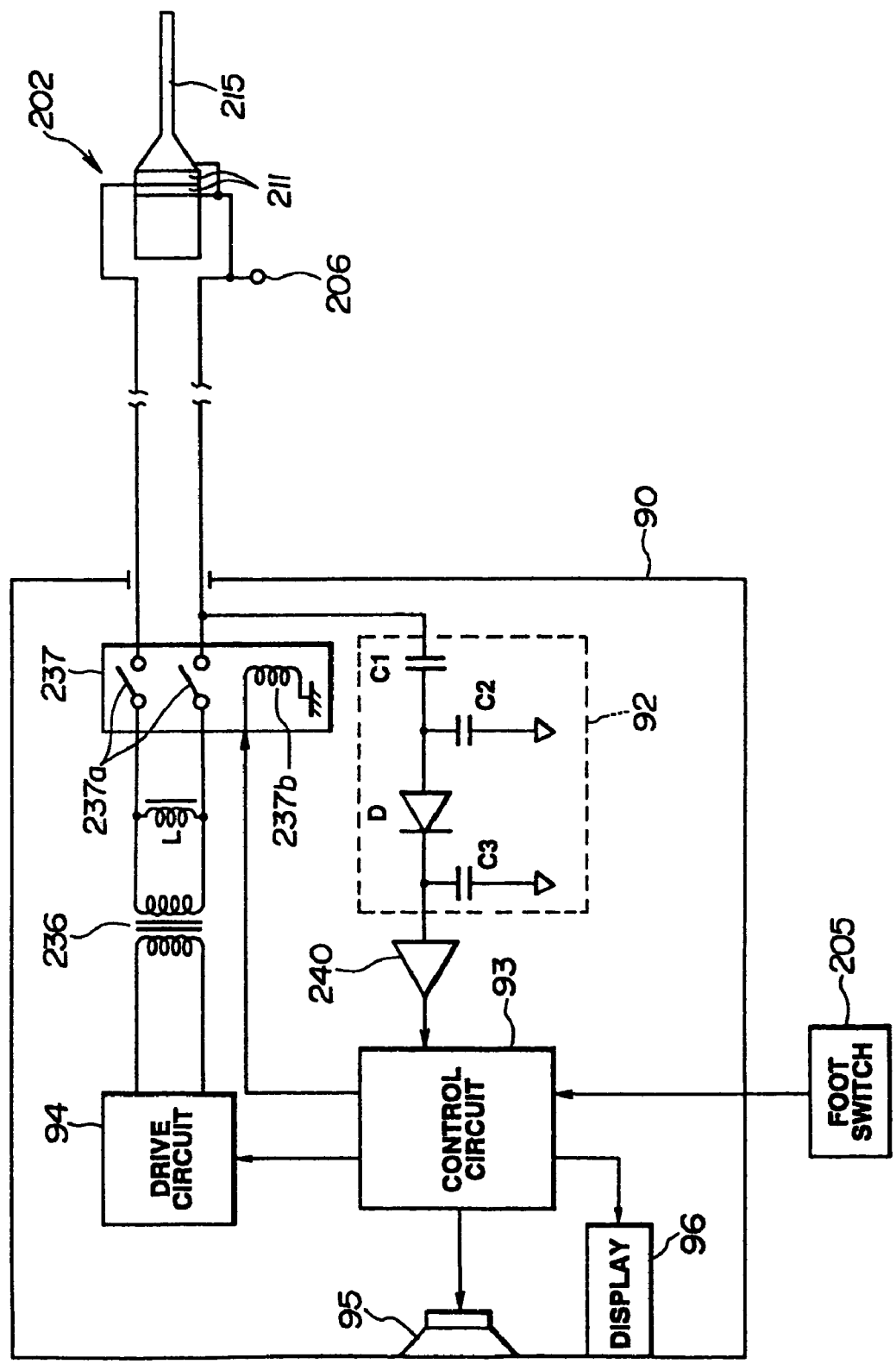

Referring to FIGS. 47 to 49, the fourteenth embodiment of the present invention will be described.

As shown in FIG. 47, an ultrasound treatment system 201 of the present invention comprises: an ultrasound treatment appliance 202 including transducers used for coagulation or incision by ultrasonic waves; a drive unit 90 for supplying a driving signal to the transducers in the ultrasound treatment appliance 202 over a driving signal conveying cord 204; a foot switch 205 connected to the drive unit 90 and used to turn on or off a driving signal; a cautery knife unit 91 that is connected to a treatment electrode receptor (active cord pin receptor) 206 attached to the ultrasound treatment appliance 202 over an active cord 207 having a detachable connector 207a and that generates a cautery knife signal supplied to a living body through the distal end of the ultrasound treatment appliance 202 for the purpose of resection or the like; an counter electrode board 209a connected to the cautery knife unit 91 and placed in contact with a wide area of a living body over a cautery knife signal return cord 209; and a foot switch 210 connected to the cautery, knife unit 91 and used to turn on or off a cautery knife signal.

Referring to FIG. 48, the electrical internal configuration of the ultrasound treatment system 201 will be described. As illustrated, disk-like ultrasonic transducers 211 are incorporated in laminated form within a transducer cover 212 of the ultrasound treatment appliance 202. The laminated ultrasonic transducers 211 are joined with a probe 215 via a horn 213. Two electrodes; voltage input electrodes 232a and 232b are formed on respective sides of each ultrasonic transducer 211. In this embodiment, one of the two electrodes or the voltage input electrode 232b is electrically connected to the metallic (broadly conducting) probe 215 over a line 233.

The treatment electrode receptor 206 serving as a cautery knife input device is electrically linked to the line 233 connected to the one voltage input electrodes 232b. Part of a cautery knife signal sent from a cautery knife signal generating circuit 235 in the cautery knife unit 91 is therefore fed to a drive circuit 94 for driving the ultrasonic transducers 211 over the line 233. This fact is utilized for sensing. A more specific configuration of the drive unit 90 is shown in FIG. 49.

As shown in FIG. 49, the drive circuit 94 generates a high-frequency sine-wave signal with a given frequency which is used to drive and make resonant the ultrasonic transducers 211. The high-frequency signal output is recomposed into a driving signal by an output transformer 236, and applied to the ultrasonic transducers 211 in the ultrasound treatment appliance 202 through contacts 237a of a relay 237. This results in ultrasonic vibrations. The secondary coil L of the output transformer 236 is a resonant coil connected in parallel with the ultrasonic transducers 211, and becomes resonant with an oscillatory frequency of the drive circuit 94 so as to excite the ultrasonic transducers 211. When a cautery knife signal is applied to the treatment electrode receptor 206 serving as a cautery knife signal input device for the ultrasound treatment appliance 202, a sense circuit 92 of a peak detection type converts the signal into a corresponding direct current as described below. Thus, the cautery knife signal is detected.

The sense circuit 92 adopts a peak detection method in which capacitors C1 and C2 stores fractions of an input voltage, a detector D detects an AC cautery knife signal developing at the capacitor C2, corresponding charge is accumulated in a capacitor C3, and the peak value of the charge is detected.

An output of the sense circuit 92 is input to a control circuit 93 via a buffer 240. In this control circuit 93, for example, an incorporated comparator compares the level of an input signal with a reference value. When the level of an input signal exceeds the reference value, a CPU that is not shown judges on the basis of an output of the comparator that a cautery knife signal has been applied to the probe 216 or a cautery knife signal is present. When the level of the input signal does not exceed the reference value, it is judged that no cautery knife signal has been applied.

When judging on the basis of a comparator output that a cautery knife signal has been applied, the CPU allows an alarm sound generating circuit that is not shown to give the alarm through a speaker 95, thus indicates that a cautery knife signal has been applied, and then prompts an operator to stop driving of ultrasonic waves. At the same time, the CPU allows a display drive circuit that is not shown to indicate on a display 96 that an cautery knife signal has been applied and that driving of ultrasonic waves should be stopped.

Furthermore, when judging that a cautery knife signal has been applied, the CPU switches off the contacts 237a so as not to cause a current to flow through a solenoid 237b of the relay 237. Besides, the CPU controls the drive circuit 94 so as to stop generation of a signal used to drive the ultrasonic transducers 211. When the relay 237 is switched off, a driving signal is not applied to the ultrasonic transducers 211 in the ultrasound treatment appliance 202.

On the other hand, when judging on the basis of a comparator output that no cautery knife signal has been applied, the CPU turns on the drive circuit 94; that is, outputs a signal to the output transformer 236, and switches on the contacts 237a and 237b of the relay 237. In this case, a treatment such as coagulation or incision by ultrasonic waves can be conducted.

In this embodiment, when a cautery knife signal is detected, the relay 237 is switched off. The ultrasound treatment appliance 202 is then disconnected from the drive circuit 94 and becomes a mere treatment appliance. The hazard that a cautery knife signal flows into the drive unit 90 and a high-frequency leakage current increases can be resolved.

Moreover, the drive circuit 94 does, unlike the one of a known system, not require various means for driving and making resonant the ultrasonic transducers while eliminating noises in a state in which a cautery knife signal is applied. The system can therefore be simplified. In this case, ultrasonic vibrations and a cautery knife output are not supplied simultaneously.

According to this embodiment, a means for detecting or sensing a cautery knife signal is included. When a cautery knife signal is detected on the basis of an output of the detecting means, off control is given so that a driving signal triggering ultrasonic vibrations will not be output to the probe 215. By contrast, when a cautery knife signal is not detected on the basis of an output of the detecting means, a driving signal triggering ultrasonic vibrations is output to the probe 215. Thus, a treatment by ultrasonic waves is enabled. Despite the simple configuration, both a treatment by ultrasonic waves and a treatment by a cautery knife can be conducted. Moreover, a disabling means for disabling simultaneous execution of both the treatments is formed so that both the treatments will not be conducted simultaneously. Safety is ensured.

In this embodiment, when a cautery knife signal is detected, signal output of the drive circuit 94 is halted (this operation is included in the meaning of switching-off control in this specification). The output line for a driving signal is switched off by means of the relay 237 located on the output stage of the drive circuit 94. A form in which signal output alone is turned off or a form in which the contacts 237a and 237b in the relay 237 are switched off is also included in the present invention.

Figure 50:
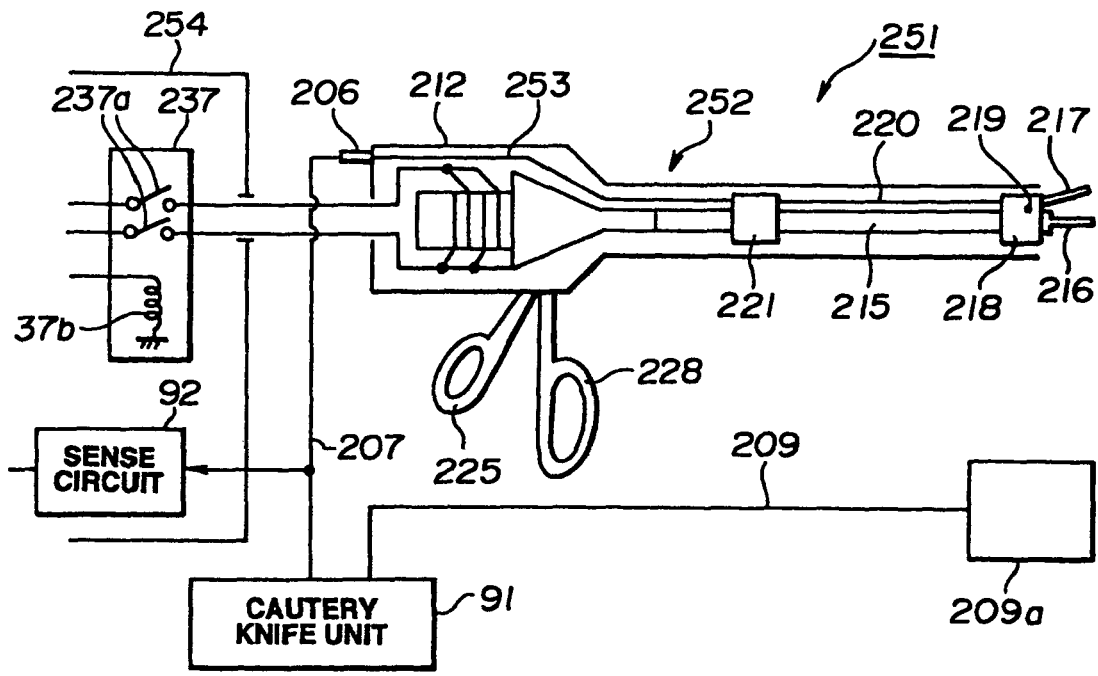
FIGS. 50 and 51 are a diagram and view for explaining the fifteenth embodiment of the present invention.
Figure 51:
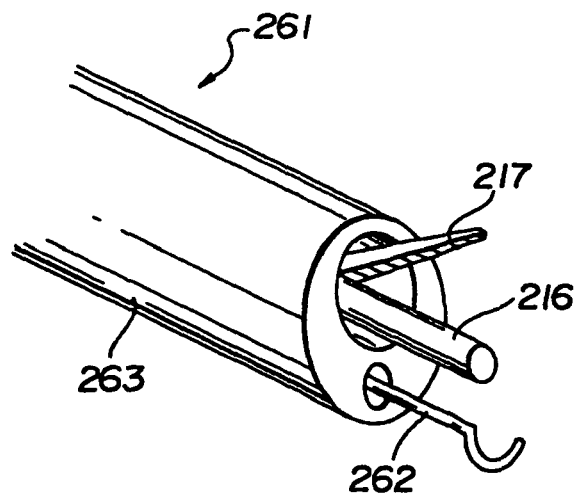

Referring to FIGS. 50 and 51, the fifteenth embodiment of the present invention will be described.

FIG. 50 shows the configuration of a major portion of an ultrasound treatment system 251 of this embodiment. A handpiece 252 in this system 251 corresponds to the ultrasound treatment appliance 202 of the embodiment shown in FIG. 49 and others. A treatment electrode receptor 206 located at the back end of a transducer cover 212 is not linked to a line 233 but connected to a conveying rod 220 secured to a rotor 222 via a connection lead 253. The conveying rod 220 is electrically connected to a holding member 217. Both a coupler 221 and distal coupler 218 are formed with insulating members.

The connection lead 253 is therefore isolated from the probe 215. In a drive unit 254 in this embodiment, an input terminal of a sense circuit 92 is not linked to the line 233 but linked to an active cord 204 connected to the treatment electrode receptor 206. The other components are identical to those of the ultrasound treatment system 201 of the fourteenth embodiment.

In this embodiment, the ability to conduct coagulation or incision by ultrasonic vibrations is identical to that in the first embodiment. The ability to conduct resection by a cautery knife is realized by the holding member 217. The mechanism of sensing a cautery knife signal is the same as that in the first embodiment except a point whether or not a detection line and a ultrasound driving signal conveying line share the same line. The advantages of this embodiment are identical to those of the first embodiment.

In the fourteenth and fifteenth embodiments, a cautery knife signal is applied to the probe 215 or holding member 217. In a handpiece 261 in FIG. 51, a cautery knife treatment electrode 262 in addition to the probe 215 and holding member 217 are inserted in a sheath 263.

A cautery knife signal is applied to the back end (not shown) of the treatment electrode 262. A detecting means for detecting whether or not a cautery knife signal has been output to the treatment electrode 262 can detect it owing to the configuration shown in FIG. 49 or 50.

Figure 52:
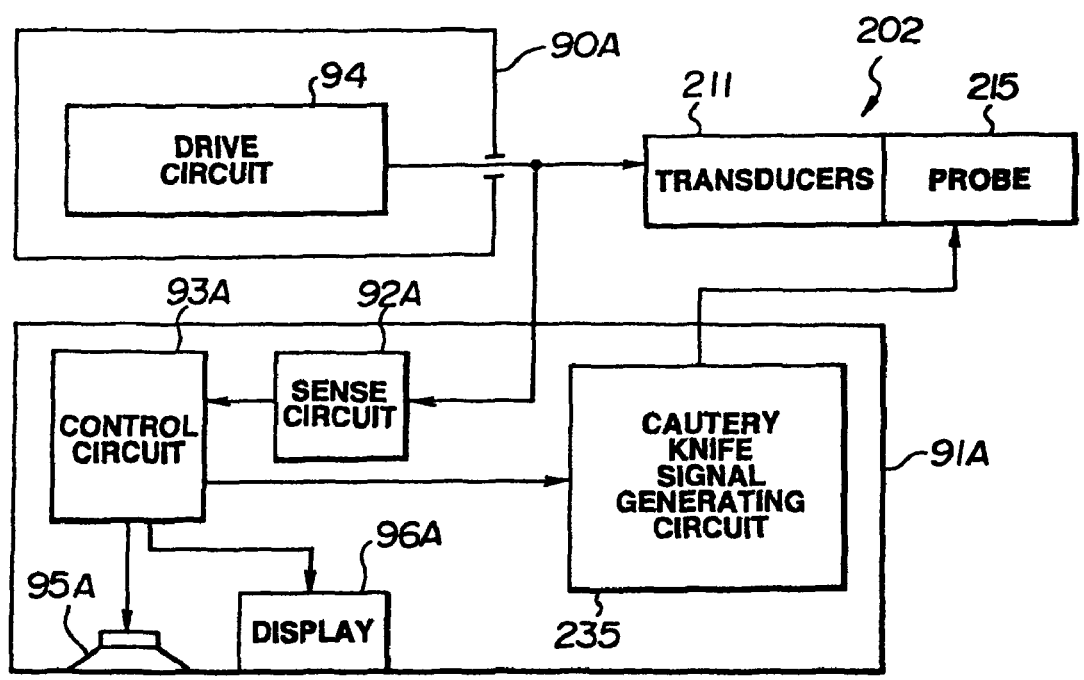
FIG. 52 is an explanatory diagram showing the overall configuration of an ultrasound treatment system of the sixteenth embodiment of the present invention.

In the foregoing embodiment, a detecting means for detecting a cautery knife signal is included in the drive unit 90. When a cautery signal is detected on the basis of an output of the detecting means, the drive unit 90 gives control so as to prevent occurrence of ultrasonic vibrations. The present invention is not limited to this mode. Alternatively, a detecting (sensing) means for detecting whether or not a driving signal sent from a drive circuit 94 is applied to ultrasonic transducers 211 may be included for example, in a cautery knife unit. In this case, a cautery knife signal sent from the cautery knife unit is turned on or off according to the output of the detecting means. This configuration is also acceptable. This configuration of the sixteenth embodiment is schematically shown in FIG. 52. As shown in FIG. 52, a drive unit 90A includes the drive circuit 94. A driving signal sent from the drive circuit 94 is applied to the ultrasonic transducers 211.

A cautery knife unit 91A includes a cautery knife signal generating circuit 235, a sense circuit 92A, a control circuit 93A, a speaker 95A, and a display 96A. The cautery knife signal generating circuit 235 generates a cautery knife signal. The cautery knife signal is applied to a probe 215 in an ultrasound treatment appliance 202 over an active cord.

The sense circuit 92A senses a driving signal applied to the ultrasonic transducers 211 according to the peak detection method, and sends an output to the control circuit 93A. The control circuit 93A judges using a comparator or the like, which receives the output of the sense circuit 92A, whether or not a driving signal is present. When it is judged that a driving signal is present, oscillation of a cautery knife signal sent from the cautery knife signal generating circuit 235 is halted or a line over which an output is fed to the probe 215 is cut off. Control is given in order, at least, to prevent a cautery knife signal from being output to the probe 215.

When judging that a driving signal has been detected, the control circuit 93A uses the speaker 95A to give the alarm or notify audibly that a cautery knife signal has been cut off. Moreover, the display 96A is used for visual notification.

On the other hand, when it is judged on the basis of the output of the sense circuit 92A that a driving signal is not present, a cautery knife signal sent from the cautery knife signal generating circuit 235 is retained in an on state in which the signal is output to the probe 215. Thus, a treatment by a cautery knife is enabled.

The operations and advantages of this embodiment are substantially the same as those of the fourteenth embodiment.

Even in the sixteenth embodiment, the structure of the handpiece in the fourteenth embodiment or fifteenth embodiment shown in FIG. 50 may be adopted.

Different embodiments formed by combining some of the constituent features of the aforesaid embodiments also belong to the present invention. For example, when a sensing means 239 senses a cautery knife signal, control is given in order to halt an ultrasonic function. Alternatively, the function of the cautery knife unit may be halted. Otherwise, it may be made selective whichever of the functions is halted. When the sensing means 239 senses a cautery knife signal, after an audible or visual alarm is given or both of them are given, the ultrasonic function or the function of the cautery knife unit may be halted for a certain period of time.

Referring to FIGS. 53 to 58, the seventeenth embodiment of the present invention will be described.

Figure 53:
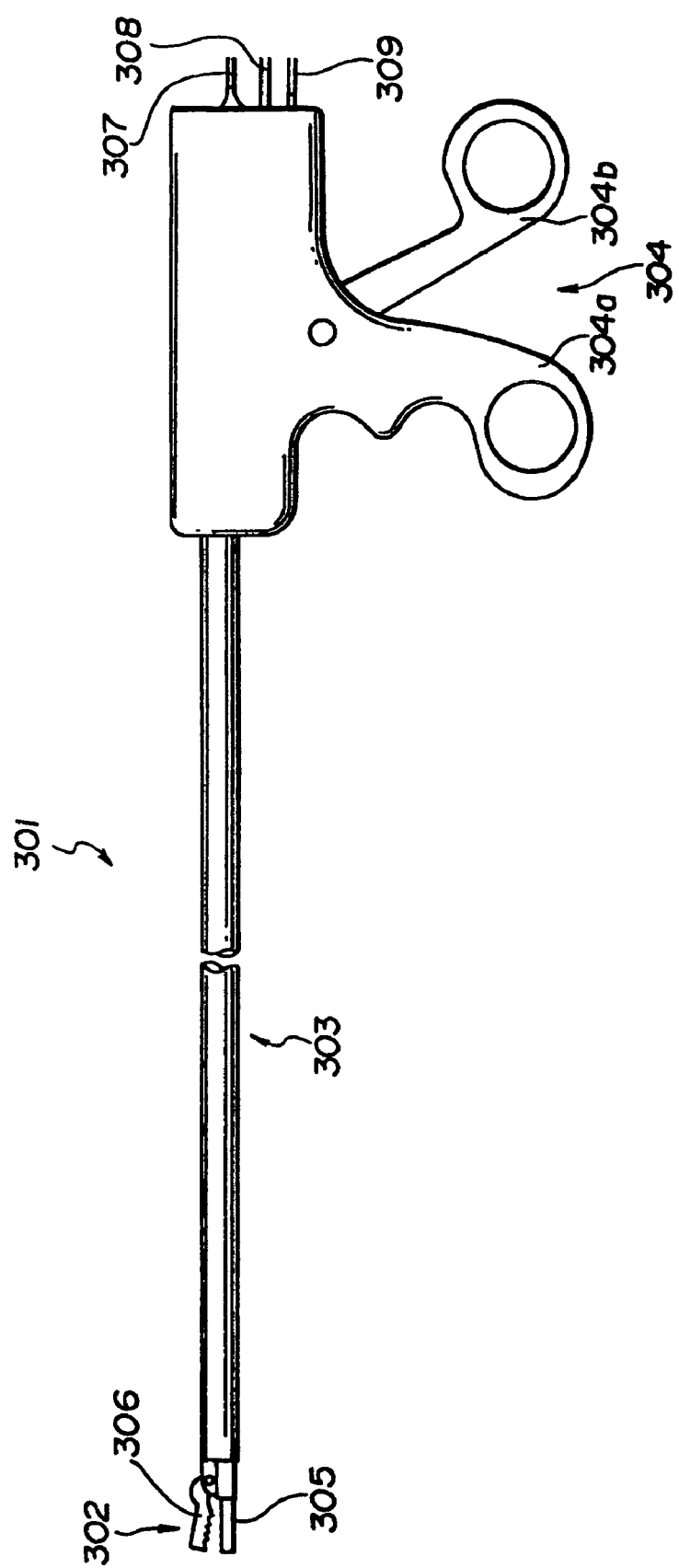
FIGS. 53 to 58 are views for explaining the seventeenth embodiment of the present invention.

As shown in FIG. 53, an ultrasound treatment appliance 301 comprises a treatment unit 302, an insertion unit 303 having a channel, which will be described later, for use in inserting the treatment unit 302 into a body cavity, and an operation unit 304 including a stationary manipulation handle 304a and a movable manipulation handle 304b which are used to manipulate the treatment unit 302. The treatment unit 302 is located at the distal end of the insertion unit 303 and composed of a probe 305 jutting out from the distal side of the insertion unit 303 and a holding member 306. Ultrasonic transducers, which will be described later, for supplying ultrasonic vibrations to the probe 305 constituting the treatment unit 302 are incorporated in the operation unit. Reference numeral 307 denotes a first high-frequency current cord.

308 denotes a second high-frequency current cord. 309 denotes an ultrasonic transducers driving cord.

Figure 54:
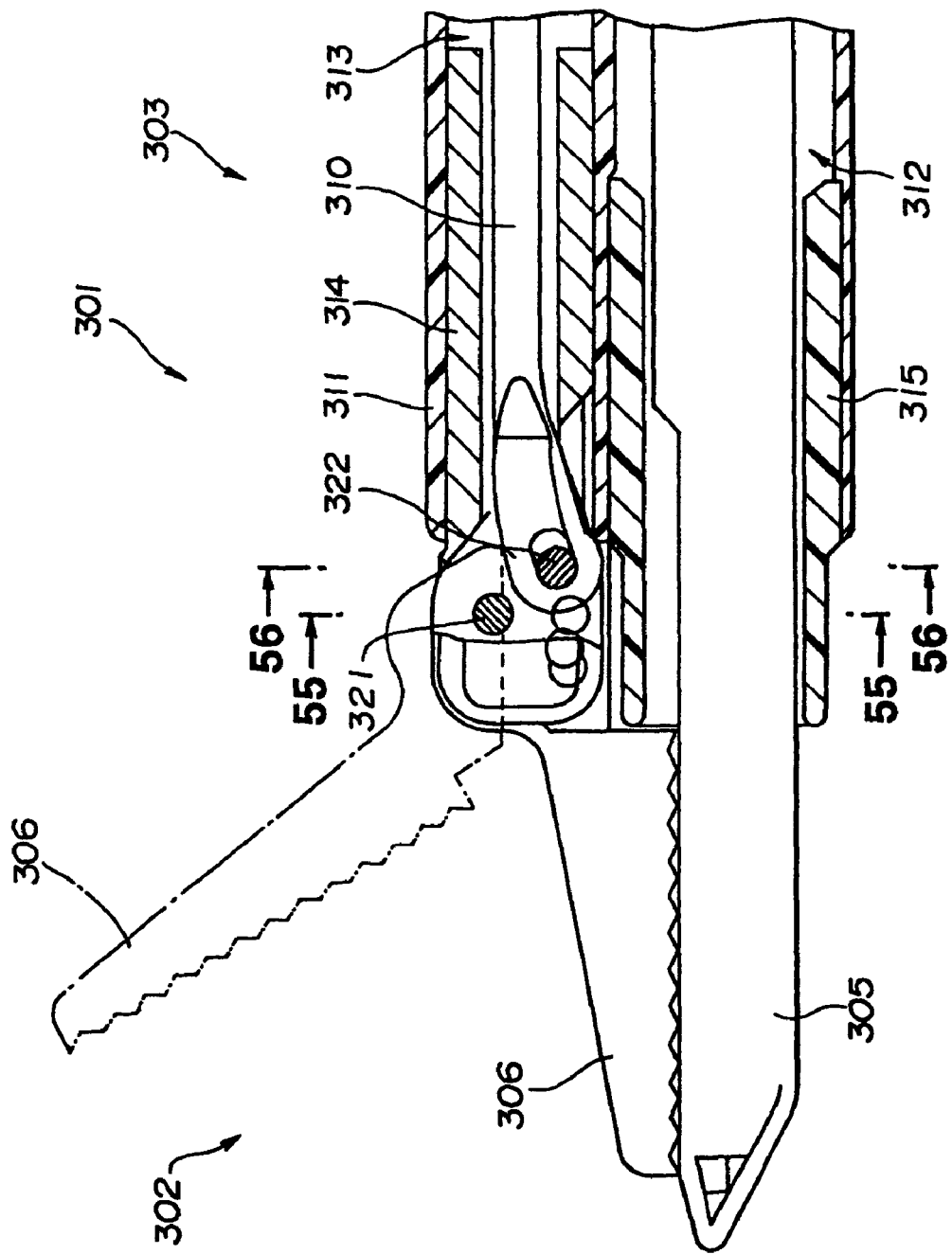

As shown in FIG. 54, the treatment unit 302 located at the distal end of the insertion unit 303 is composed of the probe 305 jutting out from the distal side of the insertion unit 303, and the holding member 306 opposed to the probe 305. When an operator manipulates the movable manipulation handle 304b of the operation unit 304, a conveying member 301 linking the movable manipulation handle 304b and holding member 306 advances or withdraws in the longitudinal direction. This causes the holding member 306 to open or close relative to the probe 305.

The insertion unit 303 is realized with a sheath 311 serving as an electrically insulating means formed with a resin member made of an electrically insulating material, for example, polysulfone or PEEK. In the sheath 311, a probe insertion channel 312 through which the probe 305 lies and a conveying member channel 313 through which the conveying member 310 linked to the holding member 306 lies are included in an electrically fully isolated manner.

Figure 55:
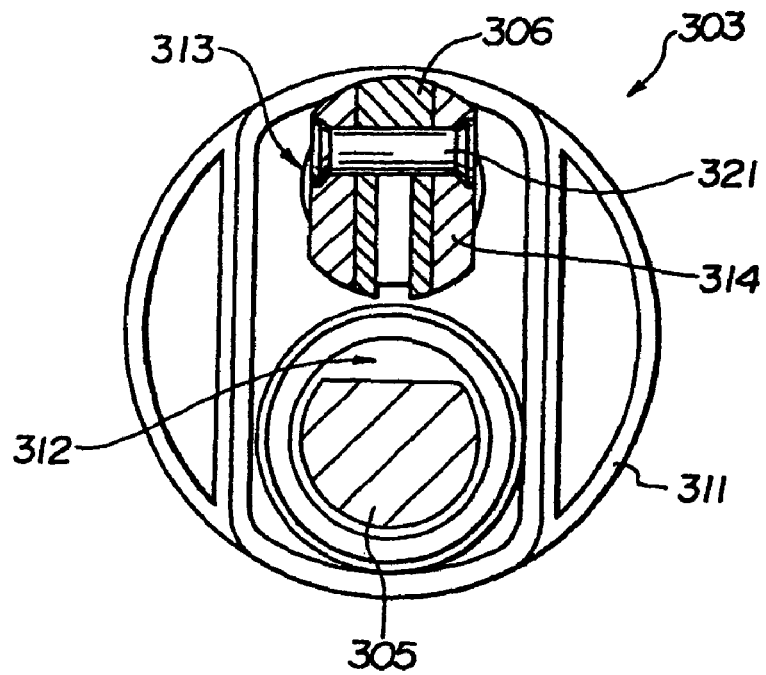
Figure 56:
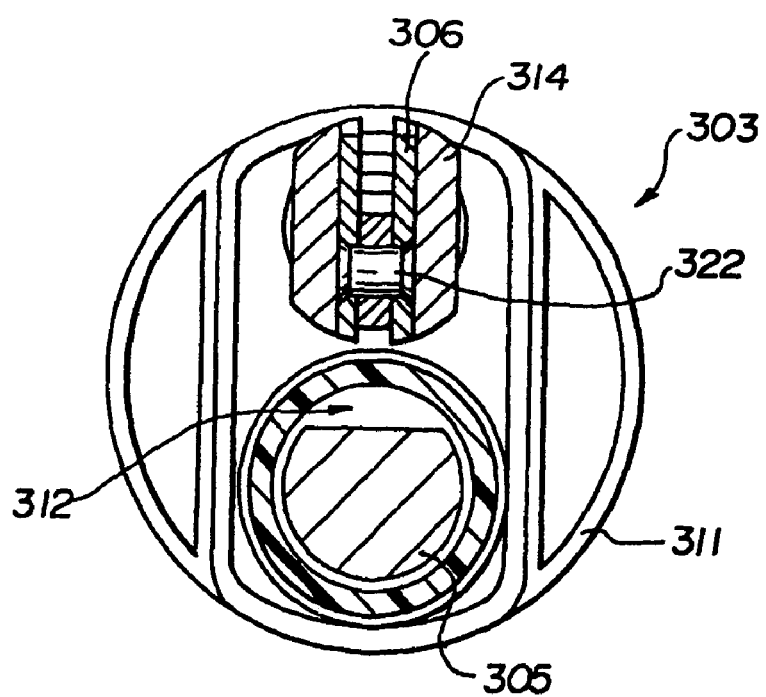

As shown in FIGS. 54 to 56, a distal cover 314 having an electrical insulation ability is fitted and locked in a distal bore of the conveying member channel 313, and is made of a resin material such as polysulfone or PEEK similarly to the sheath 311, or of a ceramic. The holding member 306 is attached to the distal cover 314 so that the holding member 306 can pivot freely with respect to a first pin 321.

Moreover, as shown in FIGS. 54 to 56, the holding member 306 is fixed to the conveying member 310 for conveying a manipulation force applied to the movable manipulation handle 304b by means of a second pin 322 so that the holding member 306 can pivot and slide freely. The holding member 306 pivots relative to the probe 305 with the first pin 321 as a center responsively to the advancement or withdrawal of the conveying member 310.

Furthermore, as shown in FIGS. 54 and 56, a protective member 315 for protecting the sheath 311 from being damaged due to the contact of the probe 305 is placed in the distal bore of the probe insertion channel 312. The protective member 315 is formed with a member having the durability to ultrasonic vibrations, excellent heat resistivity, and electrical insulation ability, for example, a ceramic or PTFE member.

The bare sides of the holding member 306 except the side thereof facing the probe 305, and the portion of the distal cover 314 exposed from the sheath 311 are CVD-coated with, for example, an insulating paint made from PTFE or the like, or a ceramic having the electrical insulation ability such as alumina ceramic. This is intended to prevent leakage of a high-frequency current.

Similarly to the holding member 306, the bare sides of the probe 305 other than those of the distal portion thereof except the side thereof facing the holding member 306 may be subjected to CVD-coating. Thus, the leakage of a high-frequency current to a living tissue can be prevented further reliably. This leads to improved safety.

Figure 57:
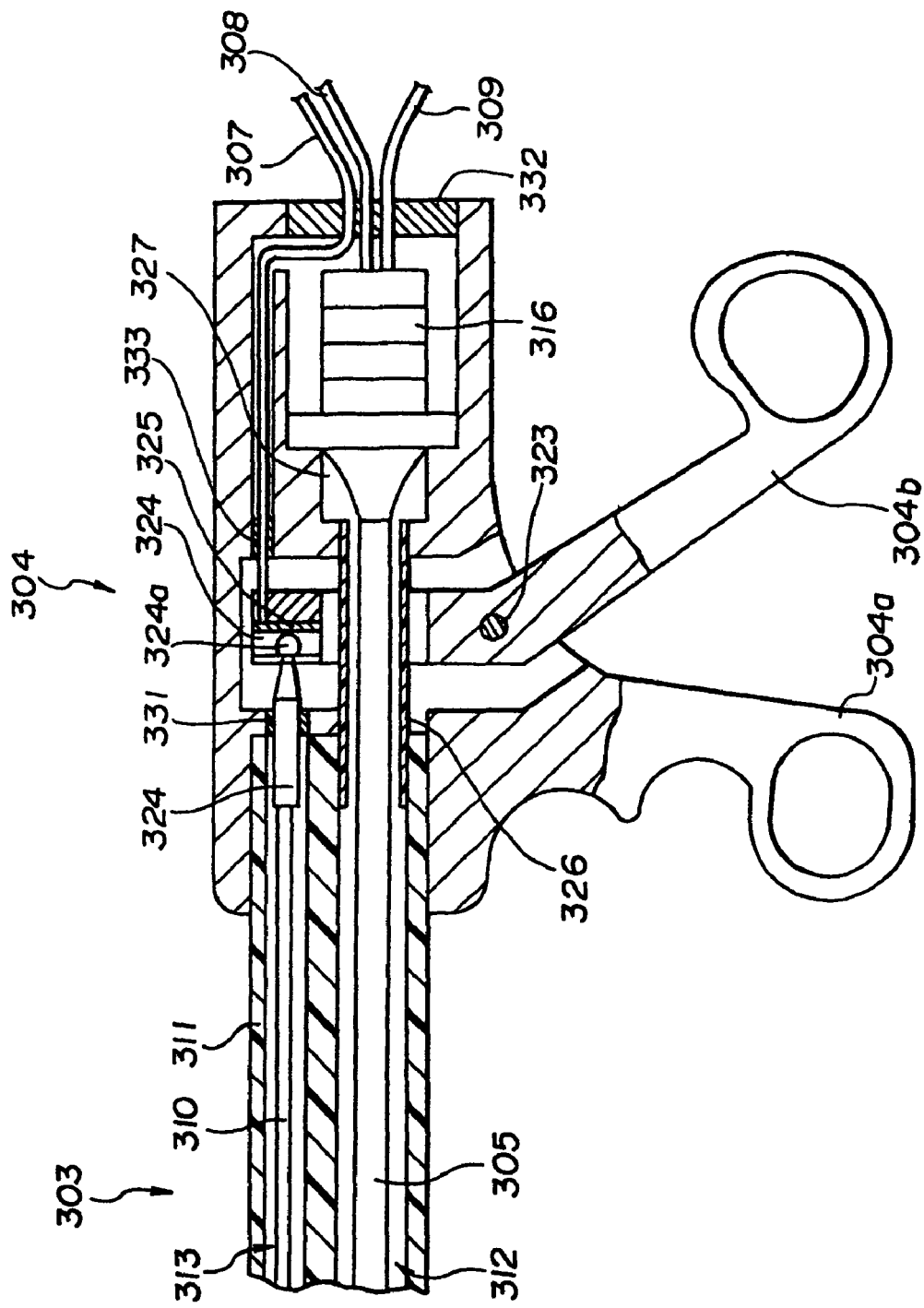
Figure 58:
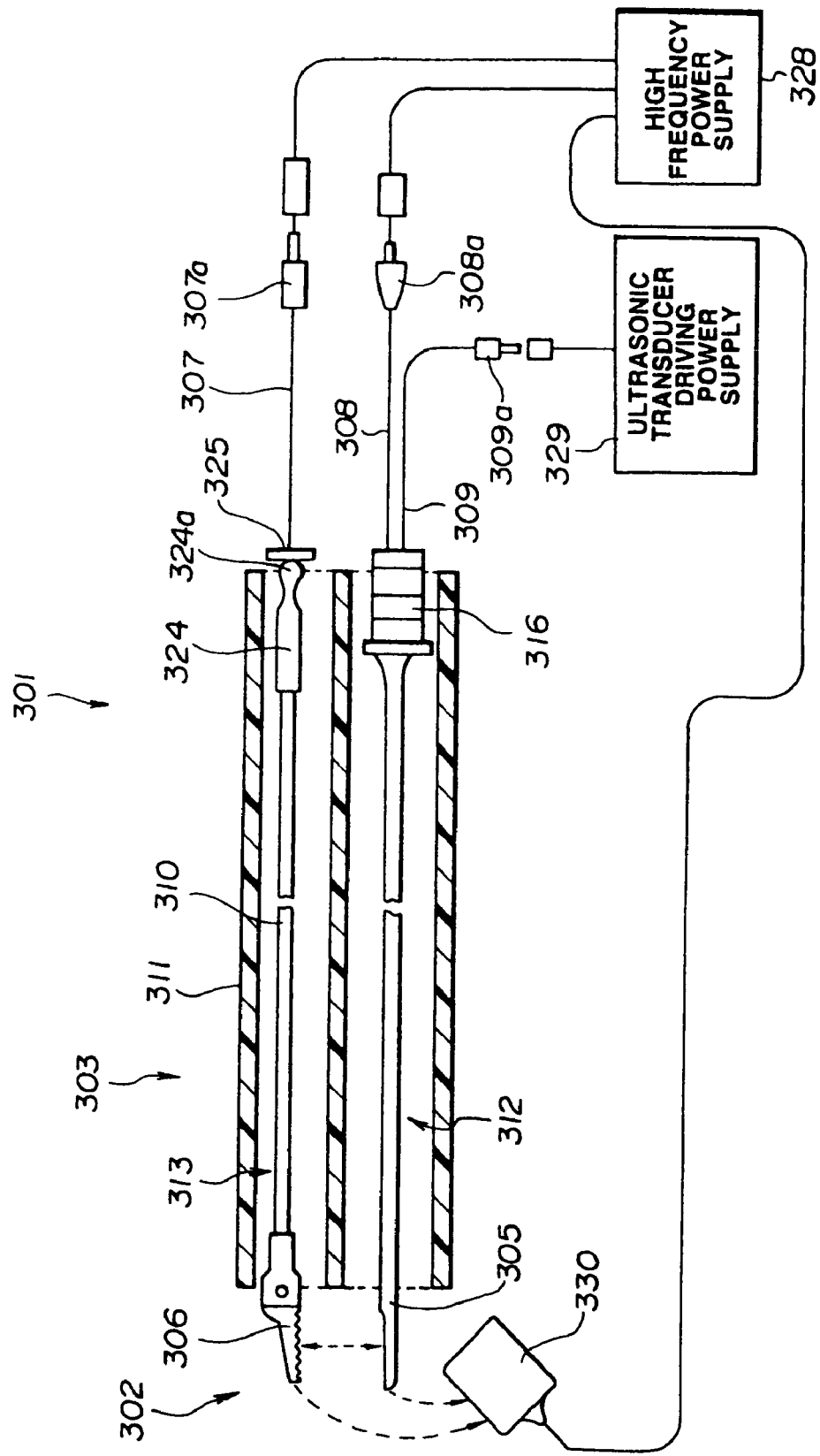

As shown in FIG. 57, the operation unit 304 is located at the proximal end of the insertion unit 303. Ultrasonic transducers 316 are included in the operation unit 304. The insertion unit 303 is connected and fixed to the upper part of the stationary handle 304a located on the distal side of the operation unit 304. The movable handle 304b is supported by a third pin 323 on the stationary handle 304a so that the movable handle 304b can pivot freely with respect to the third pin 323. The pivot of the movable handle 304b is conveyed to the conveying member 310. The stationary handle 304a and movable handle 304b are made of an electrically insulating material such as polysulfone or PEEK.

An engaging member 324 having a spherical section 324a is fixed to the proximal end of the conveying member 310. The spherical section 324a stays in an engagement ditch 324 formed in the upper part of the movable handle 304b so that the spherical section 324a can turn and slide freely. The engagement ditch 324 has a conducting member 325 in contact with the spherical section 324a. The first high-frequency current cord 307 used to supply a high-frequency current from a high-frequency power supply to the holding member 306 is connected to the conducting member 325. The second high-frequency current cord 308 used to supply a high-frequency current to the probe 305 and the ultrasonic transducer driving cord 309 used to supply a driving current to the ultrasonic transducers 316 are extending from the back of the ultrasonic transducers 316.

A first packing 331a is placed at an opening at which the end of the conveying member channel 313 in the sheath 311 constituting the insertion unit 303 is located. The first packing 331a prevents gas attributable to pneumoperitoneum from leaking out through the conveying member channel 313.

Moreover, a tube 326 formed with a resin member having the durability to ultrasonic vibrations, excellent heat resistivity, and electrical insulation ability; such as, a PTFE member is extending from the proximal end of the probe insertion channel 312 to an ultrasonic transducer housing 327 through the inside of the movable handle 304b. The probe 305 is thus isolated perfectly from the other members intervening between the probe insertion channel 312 and ultrasonic transducer housing 327.

Furthermore, the back of the ultrasonic transducer housing 327 is sealed by a second packing 332. The frontal exit for the first high-frequency current cord 307 is sealed by a third packing 333.

In other words, in the ultrasound treatment appliance 301, the probe 305 and ultrasonic transducers 316, and the engaging member 324, conveying member 310, distal cover 314, and holding member 306 are electrically perfectly isolated from each other. The probe 305 and ultrasonic transducers 316, and the engaging member 324, conveying member 310, distal cover 314, and holding member 306 are electrically isolated from the outside.

As shown in FIG. 55, in the ultrasound treatment appliance 301, the holding member 306 constituting the treatment unit 302 is connected to a high-frequency power supply 328 via the conveying member 310, engaging member 324, conducting member 325, first high-frequency current cord 307, and holding member high-frequency current connector 307a. On the other hand, the probe 305 constituting the treatment unit 302 is connected to the high-frequency power supply 328 via the ultrasonic transducers 316, second high-frequency current cord 308, and probe high-frequency current connector 308a. Furthermore, the ultrasonic transducers 316 are connected to an ultrasonic transducer driving power supply 329 via the ultrasonic transducer driving cord 309 and ultrasonic transducer driving connector 309a.

A counter electrode board 330 is connected to a feedback unit in the high-frequency power supply 328. Thus, the holding member 306 and probe 305 are electrically perfectly isolated from each other.

The operations of the ultrasound treatment appliance 301 having the foregoing structure will be described.

First, the ultrasound treatment appliance 301 is opposed to an intended living tissue in a living body. The movable handle 304b of the operation unit 304 is manipulated in order to attain an open state. The holding member 306 is thus opened relative to the probe 305.

Next, the movable handle 304b is manipulated in order to attain a closed state so that the intended living tissue can be clamped by the holding member 306 and probe 305. The holding member 306 is thus closed relative to the probe 305, whereby the living tissue is clamped.

Next, in this state, an ultrasonic transducer driving current is supplied from the ultrasonic transducer driving power supply 329 to the ultrasonic transducers 316 in order to drive the ultrasonic transducers 316. The ultrasonic transducers 316 then vibrate, whereby ultrasonic vibrations are conveyed to the probe 305. The ultrasonic vibrations are imposed on the living tissue in order to incise or coagulate the living tissue.

On the other hand, when a treatment using a high-frequency current is conducted, a living tissue is clamped by the holding member 306 and probe 305. A high-frequency current is supplied from the high-frequency power supply 328 to either the holding member 306 or the probe 305 or both of them. At this time, the high-frequency current is routed from the holding member 306 and probe 305 to the counter electrode board 330 by way of the living tissue as indicated with a dashed line in FIG. 55. The high-frequency current is then fed back to the high-frequency power supply 328, whereby the living tissue is incised or coagulated.

Incidentally, a living tissue may not be clamped by the holding member 306 and probe 305. Alternatively, the probe 305 may be pressed against a living tissue in order to impose ultrasonic vibrations. Moreover, the counter electrode board 330 may not be employed. In this case, a living tissue is clamped by the holding member 306 and probe 305, and a high-frequency current is fed to flow between the holding member 306 and probe 305 for a treatment. Furthermore, a living tissue may not be clamped but may be ablated using the holding member 306 and probe 305. Otherwise, either the holding member 306 or probe 305 may be pressed against a living tissue for a treatment.

As mentioned above, the holding member and probe are electrically perfectly isolated from each other. When a treatment using a high-frequency current is conducted, the treatment can be achieved safely without a leakage of a high-frequency current.

Moreover, since a treatment by ultrasonic vibrations and a treatment by a high-frequency current can be conducted simultaneously, it is possible that the treatment by ultrasonic vibrations is usually adopted and that the treatment by a high-frequency current is utilized only when needed. In this way, two effects of better hemostatic performance and prevention of excessive tissular alteration can be exerted.

Furthermore, when a high-frequency current is fed for a treatment, the counter electrode board may be used to pass the high-frequency current through a living tissue for a treatment. The counter electrode board may not be used, wherein a living tissue is clamped by the holding member and probe and a high-frequency current is fed to flow into the living tissue intervening between the holding member and probe. Thus, an operator can make his/her choice among a larger number of techniques.

Figure 59:
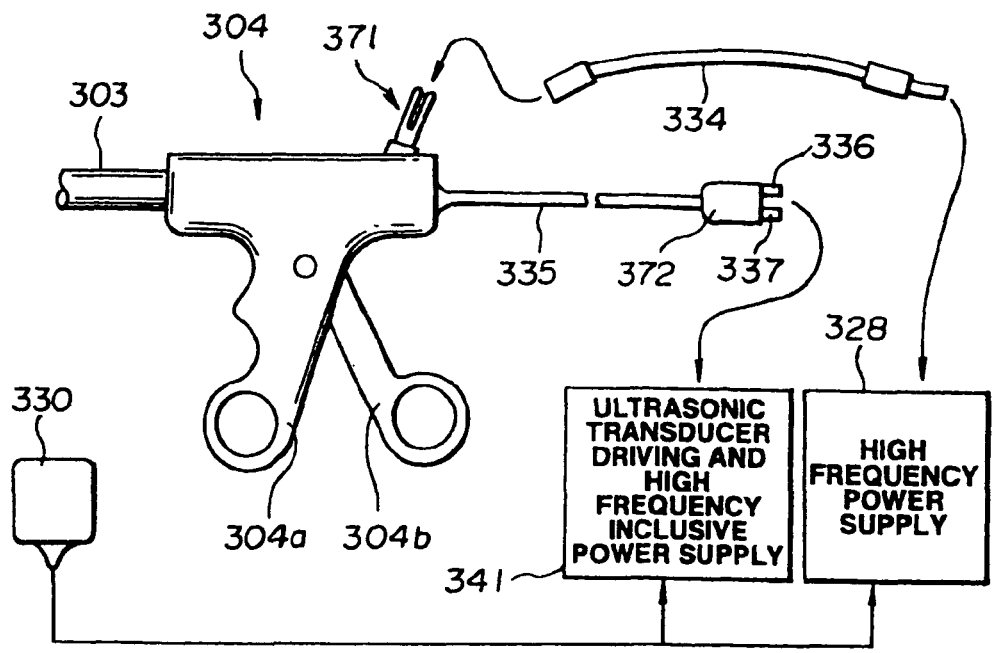
FIG. 59 is a diagram for explaining the connecting relationship between an ultrasound treatment appliance and power supplies.

Referring to FIG. 59, the relationships between an ultrasound treatment appliance and power supplies will be described.

As illustrated, in this embodiment, a holding member high-frequency current connector 371 used to supply a high-frequency current to the holding member 306 is located on the top of the operation unit 304. The holding member high-frequency current connector 371 is connected to the high-frequency power supply 328 over a high-frequency current supply cord 334.

On the other hand, a probe high-frequency current and ultrasonic transducer driving current connector 372 used to supply a high-frequency current to the probe 305 and an ultrasonic transducer driving current to the ultrasonic transducers 316 is attached to a probe high-frequency current and ultrasonic transducer driving current cord 335. A probe supply pin 336 and an ultrasonic transducer supply pin 337 are included mutually independently in the probe high-frequency current and ultrasonic transducer driving current connector 372, and connected to the probe 305 and ultrasonic transducers 316 respectively.

The probe high-frequency current and ultrasonic transducer driving current cord 335 having the probe high-frequency current and ultrasonic transducer driving current connector 372 is connected to an ultrasonic transducer driving and high-frequency inclusive power supply 341 in which a high-frequency power supply for the probe is incorporated.

In this state, the ultrasound treatment appliance is put to use. The connections of the probe to the power supply and of the ultrasonic transducers to the power supply can be made at a time. The holding member and the probe and ultrasonic transducers can be handled separately. This configuration is advantageous because of its convenience for a repair. Moreover, for supplying a high-frequency current to the holding member, the high-frequency power supply can be employed.

Figure 60:
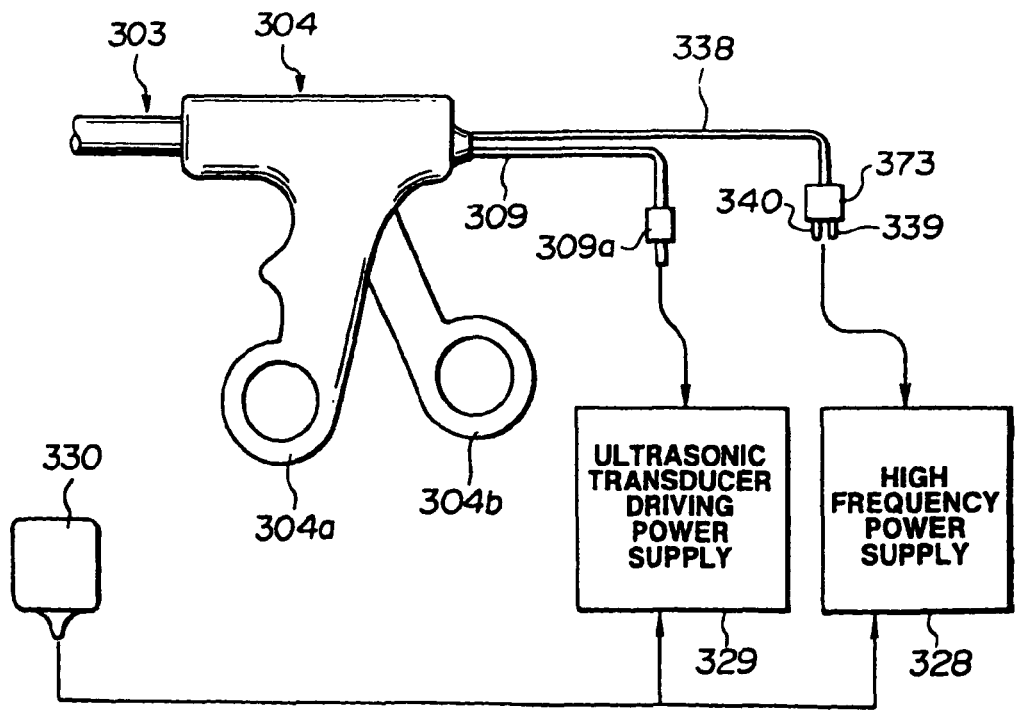
FIG. 60 is a diagram for explaining another example of the connecting relationship between an ultrasound treatment appliance and power supplies.

Referring to FIG. 60, another relationships between an ultrasound treatment appliance and power supplies will be described.

As illustrated, in this embodiment, a holding member and probe high-frequency current connector 373 used to supply a high-frequency current to the holding member 306 and probe 305 is attached to a holding member and probe high-frequency cord 338. A holding member supply pin 339 and a probe supply pin 340 are included independently in the holding member and probe high-frequency current connector 373, and connected to the holding member 306 and probe 305 respectively. The holding member and probe high-frequency cord 338 having the holding member and probe high-frequency current connector 373 is connected to the high-frequency power supply 328. In this state, the ultrasound treatment appliance is put to use.

Owing to the foregoing configuration, the connections of a high-frequency current can be achieved at a time. Moreover, the high-frequency power supply and ultrasonic transducer driving power supply can be handled separately.

Figure 61:
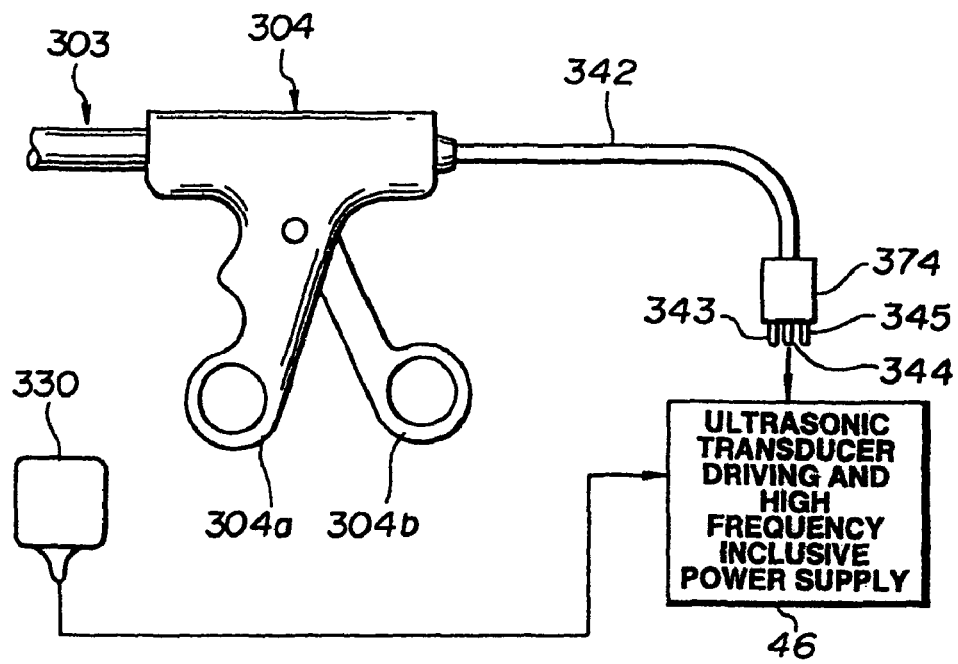
FIG. 61 is a diagram for explaining another example of the connecting relationship between an ultrasound treatment appliance and a power supply.

Referring to FIG. 61, another relationships between an ultrasound treatment appliance and power supplies will be described.

As illustrated, in this embodiment, a holding member/probe high-frequency current and ultrasonic transducer driving current connector 374 for supplying a high-frequency current to the holding member 306 and probe 305 and supplying an ultrasonic transducer driving current to the ultrasonic transducers 316 is attached to a holding member and probe and ultrasonic transducer cord 342. A holding member supply pin 343, a probe supply pin 344, and an ultrasonic transducer supply pin 345 are included independently in the holding member/probe high-frequency current and ultrasonic transducer driving current, connector 374, and connected to the holding member 306, probe 305, and ultrasonic transducers 316 respectively. The holding member and probe and ultrasonic transducer cord 342 having the holding member/probe high-frequency current and ultrasonic transducer driving current connector 374 is connected to an ultrasonic transducer driving and high-frequency inclusive power supply 346 having a holding member and probe high-frequency power supply. In this state, the ultrasound treatment appliance is put to use. Owing to this configuration, all connections can be made at a time and all power supplies can be integrated into one.

Figure 62:
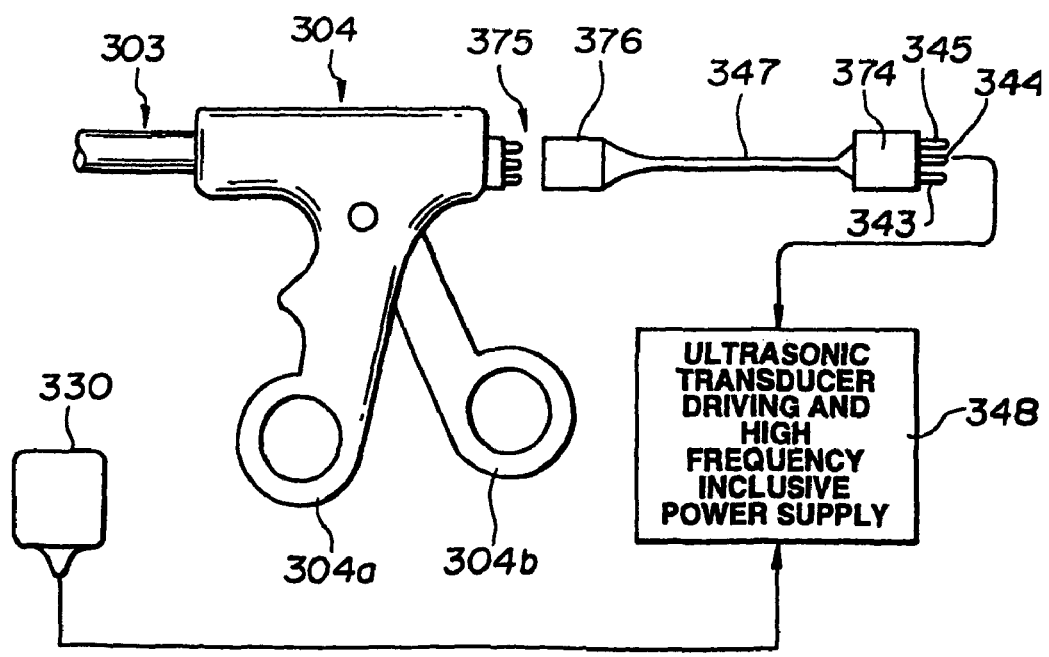
FIG. 62 is a diagram for explaining yet another example of the connecting relationship between an ultrasound treatment appliance and a power supply.

Referring to FIG. 62, yet another relationships between an ultrasound treatment appliance and power supplies will be described.

As illustrated, in this embodiment, a holding member and probe and ultrasonic transducer cord 347 having a holding member/probe high-frequency current and ultrasonic transducer driving current connector 374 is detachable, from the operation unit 304. The operation unit 304 is therefore provided with a holding member/probe high-frequency current and ultrasonic transducer driving current connector 375. The holding member and probe and ultrasonic transducer cord 347 is provided with a holding member/probe high-frequency current and ultrasonic transducer driving current connector 376 that is detachable from the holding member/probe high-frequency current and ultrasonic transducer driving current connector 375. The holding member and probe and ultrasonic transducer cord is connected to an ultrasonic transducer driving and high-frequency inclusive power supply 348. In this state, the ultrasound treatment appliance is put to use owing to this configuration, the ultrasound treatment appliance can be separated from the cord. Replacement of a cord which is prone to a trouble such as a disconnection can be completed readily. Moreover, since work can proceed with the cord separated during cleaning and sterilization, workability improves. Furthermore, cords having different lengths can be used. A cord that is prone to a trouble such as a disconnection can be replaced with a new one readily.

Figure 63A:
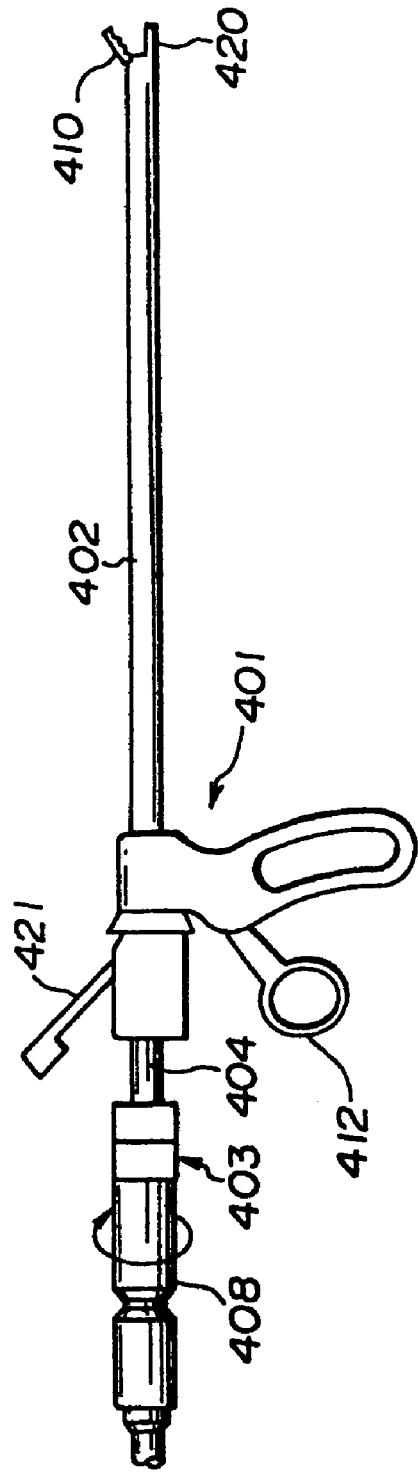
FIG. 63A is a view showing a state in which a probe is inserted in a sheath.
Figure 63B:
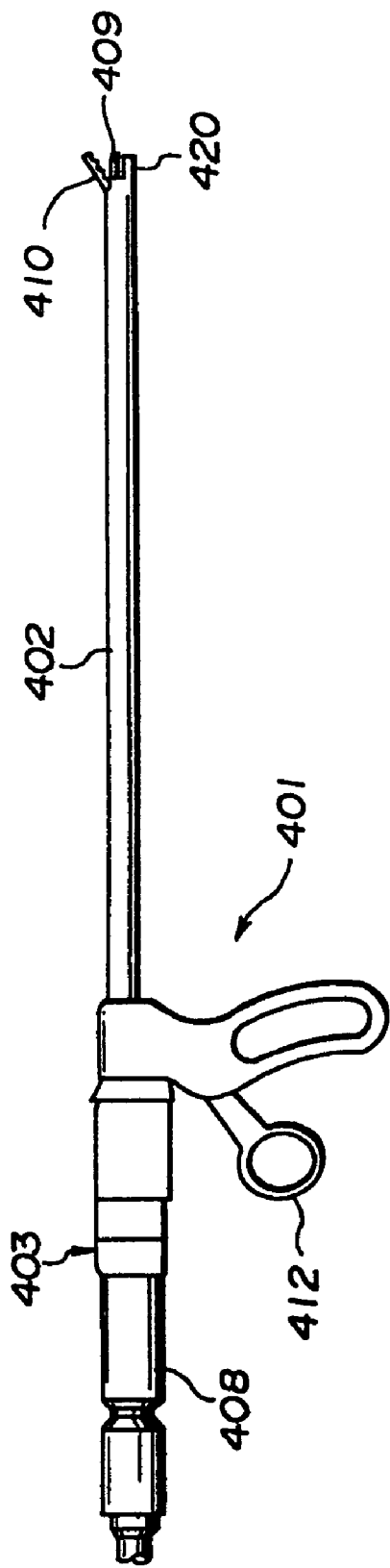
FIG. 63B is a view showing a state in which the probe is mounted at a given position in the sheath.
Figure 64:
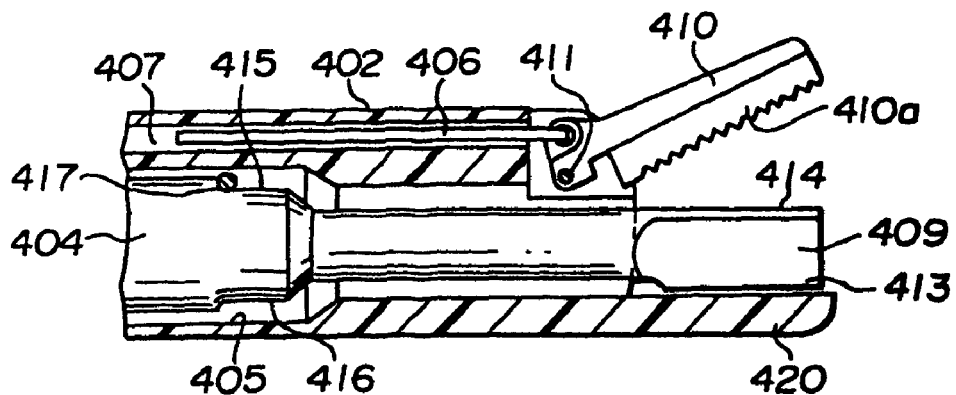
Figure 65:
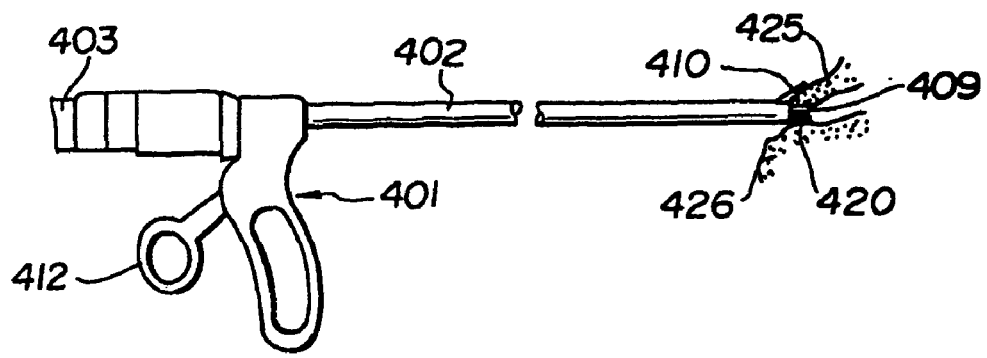

Referring to FIGS. 63 to 65, the eighteenth embodiment of the present invention will be described.

FIG. 63 shows the overall appearance of an ultrasound treatment appliance. In the drawing, reference numeral 401 denotes an operation unit. A sheath 402 that is an elongated protective member is connected to the operation unit 401. An insertion hole 405 through which a conveying rod 404 serving as a vibration conveying member for an ultrasound probe 403 is passed and an insertion hole 407 through which a holding operation rod 406 is passed are defined in the sheath 402.

The conveying rod 404 connected to the ultrasound probe 403 is inserted in the insertion hole 405 in the sheath 402 so that the conveying rod 404 will be freely detachable. The conveying rod 404 is incorporated in the insertion hole 405 so that it can also turn.

The ultrasound probe 403 includes an ultrasonic oscillator 408 having ultrasonic oscillatory devices coupled to the proximal end of the conveying rod 404. Ultrasonic vibrations oscillated by the ultrasonic oscillator 408 are conveyed to a treatment section 409 through the conveying rod 404.

A holding member 410 with a holding butt is attached to the distal end of the sheath 402 so that the holding member 410 can pivot with an axis pin 411 as a supporting point. The holding member 410 is positioned so that the holding member 410 will adjoin the distal portion of the conveying rod 404 and be opposed to the top of the distal portion thereof. The distal end of the holding operation rod 406 is attached to the holding member 410 at a position near the proximal end of the holding member 410 and off the supporting point of the axis pin 411.

Owing to the foregoing structure, when the holding operation rod 406 is advanced, the holding member 410 pivots toward the distal end of the conveying rod 404 and closes. By contrast, when the holding operation rod 406 is withdrawn, the holding member 410 opens. FIGS. 63A, 63B, and 64 show a state in which the holding member 410 is open. The operation unit 401 has an open/close manipulation lever 412 serving as a manipulator for advancing or withdrawing the holding operation rod 406.

The distal portion of the conveying rod 404 has a much smaller diameter than the other portion. The tip of the distal portion constitutes the treatment section 409 that is a section jutting out from the distal end of the sheath 402. The treatment section 409 jutting out from the distal end of the sheath 402 is opposed to a holding butt 410a of the holding member 410. The treatment section that juts out from the distal end of the sheath 402 has a coagulation surface 413 used to coagulate a living tissue formed on one side thereof. An incision area 414 used to incise a living tissue is formed on the opposite side of the treatment section. In other words, the coagulation surface 413 that is blunt and round in shape is formed on the upper side in FIG. 64, and the incision area 414 is formed as a knife-like sharp edge on the lower side therein.

In the conveying rod 404, engagement sections 415 and 416 that are flat steps are formed on the top and bottom of the distal part of the large-diameter portion that is continuous to a small-diameter distal portion via the steps. At least one alignment pin 417 traversing the conveying rod insertion hole 405 in the sheath 402 is located, in a relatively upper area of the insertion hole 405. The engagement section 415 or 416 is engaged with the alignment pin 417. Herein, the one alignment pin 417 is installed in the upper area. Only the engagement pin 415 or 146 that has been oriented upward by turning the conveying rod 404 engages with the alignment pin 417. The coagulation surface 413 or incision area 414 associated with the engagement section 415 or 146 engaged with the alignment pin 417 is oriented upward and opposed to the holding butt 410a of the holding member 410.

Furthermore, a fragment-like guard member 420 jutting out to the same extent as the treatment section 409 of the ultrasound probe 403 is formed as part of the sheath 402 by stretching the lower part of the distal end of the sheath 402. The guard member 420 is located just under the treatment section 409 jutting out from the sheath 402 in order to cover the sharp blade of the incision area 414 opposed to the guard member 420. In other words, the guard member 420 is located on the opposite side of the treatment section 409 relative to the holding member 410 and covers the side of the treatment section 409 not facing a living tissue to be treated.

On the other hand, the operation unit 401 has a stopper lever 421 that when the conveying rod 404 joined with the ultrasound probe 403 is inserted in the sheath 402, stops the ultrasound probe 403. When the stopper lever 421 is raised as shown in FIG. 63A, insertion or removal of the ultrasound probe 403 is enabled. When the stopper lever 421 is leveled off, removal of the ultrasound probe 403 is disabled.

Next, the operations of the ultrasound treatment appliance in use will be described.

First, the orientation of the treatment section 409 of the conveying rod 404 is defined according to the purpose of use. FIG. 64 shows a state in which a living tissue is coagulated. The coagulation surface 413 of the treatment section 409 formed as the distal portion of the conveying rod 404 faces upward and is opposed to the holding member 410. For incising a living tissue, the conveying rod 404 is turned 180° so that the incision area 414 of the treatment section 409 will face upward and be opposed to the holding member 410.

The change of the states can be achieved as described below. That is to say, the stopper lever 421 is raised as shown in FIG. 63A, and the conveying rod 404 is withdrawn. The engagement section 415 or 146 engaged with the alignment pin 417 is thus escaped from the alignment pin 417. This enables the conveying rod 404 to turn freely. When the whole ultrasound probe 403 is turned 180° as shown in FIG. 63A, the orientation of the treatment section 409 is inverted. Consequently, the orientations of the coagulation surface 413 and incision area 414 are switched. Thereafter, the conveying rod 404 is advanced so that the upper engagement section 415 will be engaged with the alignment pin 417. The orientation of the conveying rod 404 is thus aligned and fixed at that position. The stopper lever 421 is leveled off as shown in FIG. 63B. Consequently, the ultrasound probe 403 is fixed to the operation unit 401.

Next, the operation for coagulating a living tissue will be described.

For direct surgery or surgery under laparoscopic observation, a trocar, endoscope, or the like is used to introduce the ultrasound treatment appliance into a body cavity. A living tissue 425 is then, as shown in FIG. 65, clamped by the holding member 410 and coagulation surface 413. Thereafter, ultrasonic waves are oscillated, and vibrations are conveyed to the treatment section 409 through the conveying rod 404. The living tissue 425 clamped by the holding member 410 and the coagulation surface 413 of the treatment section 409 making ultrasonic vibrations is cauterized with frictional heat resulting from the vibrations, and thus coagulated.

During the coagulation, the incision area 414 opposite to the coagulation surface 413 is covered by the guard member 420 and prevented from touching a normal living tissue 426.

As mentioned above, it will not take place that the normal living tissue 426 is cauterized while being invisible to an operator. There is no possibility that when ultrasonic vibrations are not produced, the sharp incision area 414 touches and injures a living tissue. Thus, a user-friendly ultrasound treatment appliance can be provided.

Figure 66:
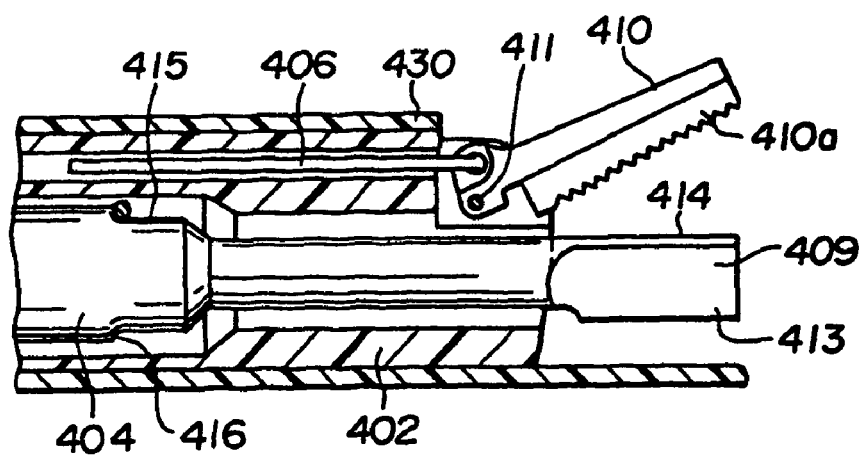
FIG. 66 is a sectional view for explaining the structure of a treatment section of an ultrasound treatment instrument of the nineteenth embodiment of the present invention.

Referring to FIG. 66, the nineteenth embodiment of the present invention will be described.

This embodiment is basically identical to the aforesaid eighteenth embodiment. The distal portion of the sheath 402 is devoid of the guard member 420. Part of the distal portion is cut out. The distal portion has a length permitting the distal portion to reach the root of the treatment section 409 of the ultrasound probe 403.

On the other hand, the circumference of the sheath 402 is covered with an outer sheath 430. A guard member 431 having the same ability as the guard member 420 and jutting out to the tip of the treatment section provided as the distal portion 409 of the ultrasound probe 403 is formed at the distal end of the outer sheath 430.

The outer sheath 430 and sheath 402 are engaged with each other and can therefore be separated from each other. In other words, the outer sheath 430 can be detached from the sheath 402. For a region in which the guard member 431 is needed and observation is hard to do, the ultrasound treatment appliance is used with the outer sheath 430 attached. For a region in which a better field of view is ensured and, especially, the guard member 431 is unnecessary, the ultrasound treatment appliance is used to conduct a treatment with the outer sheath 430 detached. An operator can determine whether or not to use the guard member 431 and proceed with work in a minimum necessary optimal state.

Figure 67:
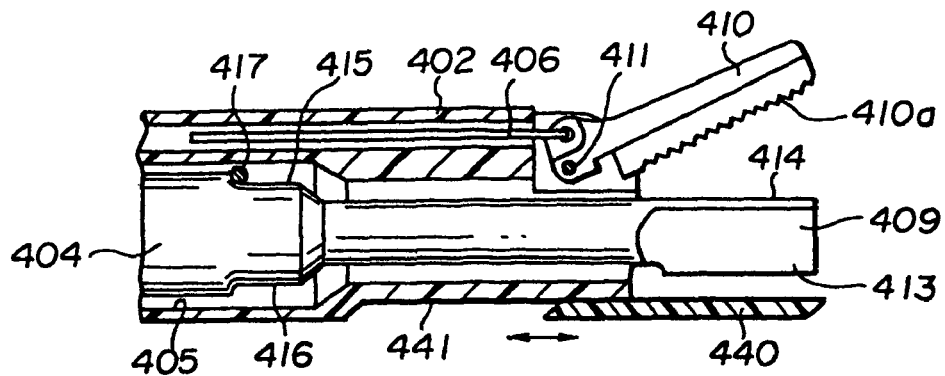
FIG. 67 is a sectional view showing a treatment section of an ultrasound treatment appliance of the twentieth embodiment of the present invention.

Referring to FIG. 67, the twentieth embodiment of the present invention will be described.

In this embodiment, a guard member 440 having the same ability as the aforesaid guard members is attached under the distal portion of the sheath 402 so that the guard member 440 can slide freely along the longitudinal axis of the sheath 402. A sliding engagement section having a concave part 441, with which a convex part formed on the guard member 440 is engaged so that the guard member 440 can slide freely, is formed as a sliding mechanism.

After the convex part is engaged with the concave part, the guard member 440 can freely slide back and forth on the sheath 402 as indicated with arrows in FIG. 67. For use, the guard member 440 is advanced and jutted out. When not used, the guard member 440 is withdrawn and escaped under the sheath 402. Temporary lock may be attained using frictional force induced between the guard member 440 and the concave area 441 with which the guard member 440 engages or using a click stop or the like. Alternatively, any other locking means may be used.

An operator may or may not attach the guard member 440 as he/she likes. Moreover, the operator should merely slide the guard member. The used and unused states of the guard member can be switched readily without the labor for detaching the outer sheath in the second embodiment.

Needless to say, the guard member 440 can not only be slided but also be detached from the sheath 402.

Figure 68:
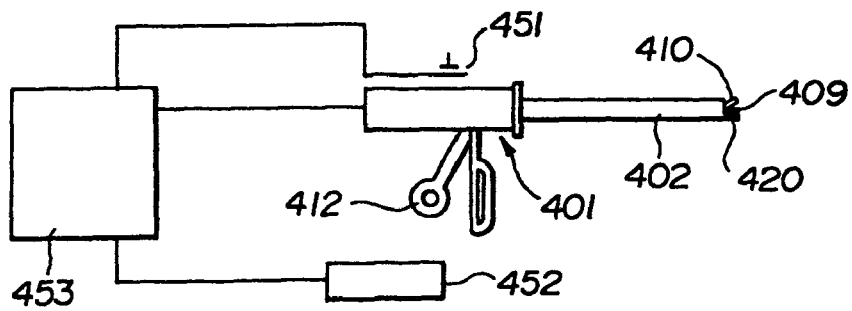
FIG. 68 is an explanatory diagram showing the outline configuration of an ultrasound treatment system of the twenty-first embodiment of the present invention.

Referring to FIG. 68, the twenty-first embodiment of the present invention will be described.

In this embodiment, in an ultrasound treatment system, ultrasonic oscillations can be operated by both a hand switch 451 formed on the operation unit 401 of an ultrasound treatment appliance and a foot switch 452 independent of the hand switch 451.

An ultrasonic oscillator in the ultrasound probe 403 is connected to a main unit 453 including an ultrasonic oscillatory signal source. The hand switch 451 and foot switch 452 are also connected to the main unit 453. On-off control of ultrasound oscillations can be achieved using either the hand switch 451 or foot switch 452. When the hand switch 451 is used, an on-off operation can be performed in parallel with manipulation of forceps by the operation unit 401. The ultrasound treatment appliance has the same structure as those described in other embodiments.

Figure 69:
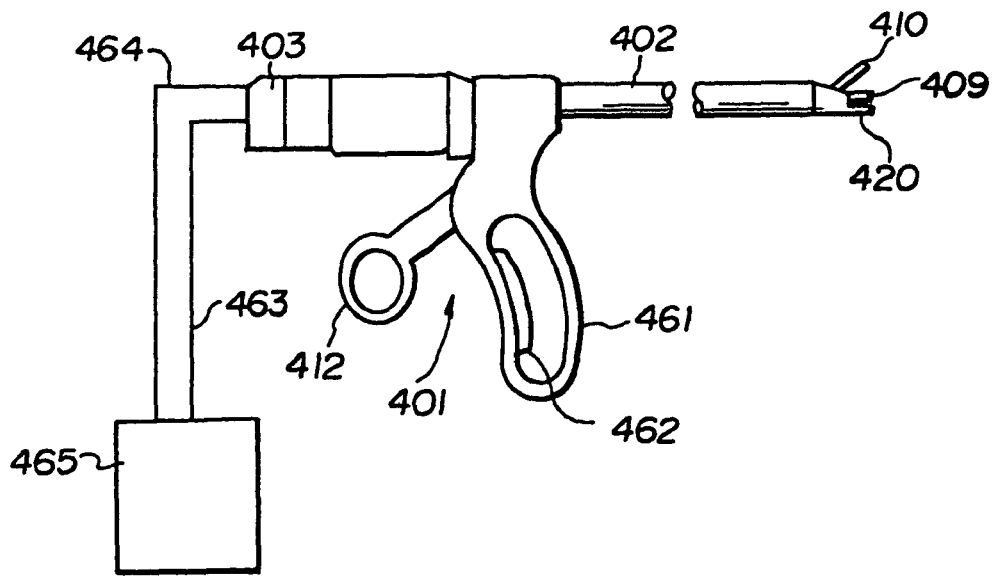
FIG. 69 is an explanatory diagram showing the outline configuration of an ultrasound treatment system of the twenty-second embodiment of the present invention.

Referring to FIG. 69, the twenty-second embodiment of the present invention will be described.

This embodiment attempts to properly perform the on-off operation of ultrasonic oscillations in an ultrasound treatment system according to coagulation or incision of a living tissue.

To be more specific, the operation unit 401 of an ultrasound treatment appliance is provided with a pair of handles; a frontal handle 461 attached on a stationary basis and the open/close manipulation lever 412. A thumb is rested on the open/close manipulation lever 412 serving as a rear handle, and any other fingers are rested on the frontal handle 461 in order to grip the frontal handle 461. A pressure switch 462 realized with a pressure sensor or the like that conducts with application of a certain amount of pressure is formed on the portion of the frontal handle 461 gripped by a hand. A signal sent from the pressure switch 462 is sent to a main unit 465 including an ultrasonic oscillatory signal source over a signal line 464 united with a power cable 463. A vibration occurrence control means in the main unit 465 turns on or off ultrasound oscillations.

In other words, when an object tissue on the treatment section 409 of the ultrasound treatment appliance is clamped by manipulating the pair of manipulation handles; that is, the frontal handle 461 and open/close manipulation lever 412, a certain amount of pressure is applied to the pressure switch 462. After the living tissue is clamped, if the pair of manipulation handles is gripped more strongly, the pressure switch 462 produces an on signal. Consequently, ultrasonic waves are oscillated to enable coagulation or incision of the living tissue. After a treatment is completed, a hand is released or force is alleviated. Oscillations are then automatically turned off. Thus, a more precise force can be exerted.

According to this embodiment, oscillations can be produced only when needed. It becomes unnecessary to press the foot switch or hand switch every time. An incorrect press of the switch will therefore not occur. Consequently, a surgical procedure can be conducted more safely and accurately. Since excessive cords are excluded, it becomes easy to make preparations and straighten things up.

Figure 70A:
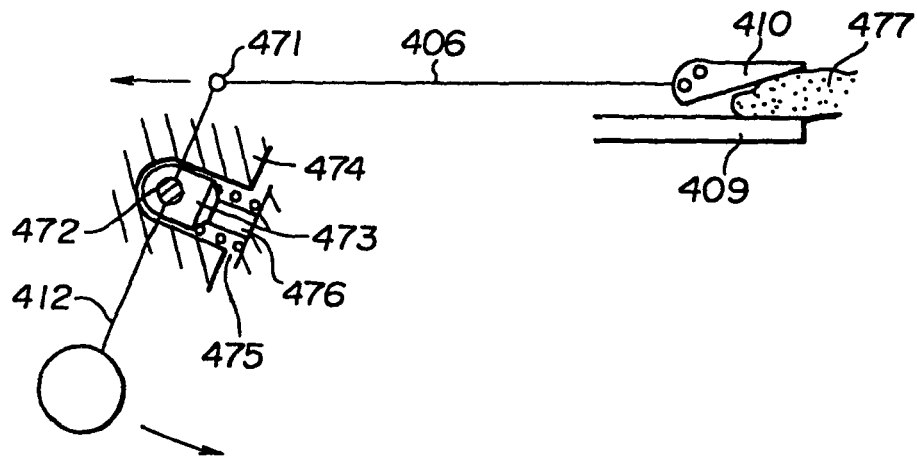
FIGS. 70A and 70B are diagrams for explaining the twenty-third embodiment of the present invention.
Figure 70B:
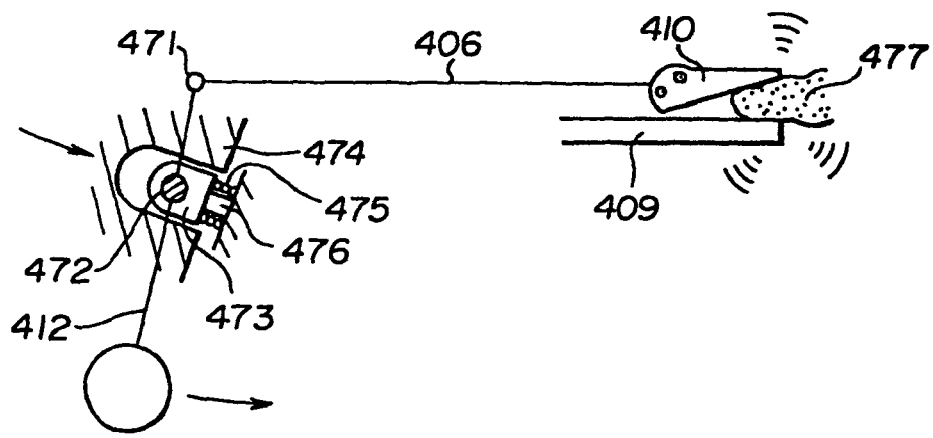

Referring to FIGS. 70A and 70B, the twenty-third embodiment of the present invention will be described.

This embodiment also attempts to properly perform the on-off operation of ultrasonic oscillations in an ultrasound treatment system according to coagulation or incision of a living tissue.

FIGS. 70A and 70B are explanatory diagrams graphically showing a switching mechanism incorporated in an ultrasound treatment appliance similar to the aforesaid one.

Specifically, the holding member 410 is, as mentioned above, opened or closed by manipulating the handles of the operation unit 401. The operation rod 406 is connected to the open/close manipulation lever 412 serving as the rear handle at a supporting point 471 in the operation unit 401. A supporting point 472 is defined in the middle of an arm of the open/close manipulation lever 412. The supporting point 472 is included in a sliding member 473. The sliding member 473 is stowed in a guide section 474 formed in the operation unit 401 so that the sliding member 473 can slide freely. Normally, the sliding member 473 is pressed to the end of the guide section 474 by an elastic constraining means such as a coil spring 475 or blade spring. On the sliding member 473, a on-off button 476 for a switch is located on the opposite side of the sliding member 473 relative to the supporting point 472.

When the open/close manipulation lever 412 serving as a rear handle is moved forward as shown in FIG. 70A, the operation rod 406 moves forward. The holding member 410 closes to clamp an object living tissue 477 in cooperation with the treatment section 409 of the ultrasound probe 403. Thereafter, when more force is applied, the supporting point 472 moves along with the sliding member 473 in a direction in which the coil spring 475 is contracted. Consequently, the on/off button 476 for the switch is pressed. This activates the switch. Ultrasonic waves are oscillated, thus enabling the treatment of the object tissue. When force is alleviated, the supporting point 472 returns to the original position. The on/off button 476 is set to an off state.

Thus, oscillations can be produced only when needed. It becomes unnecessary to press the foot switch or hand switch every time. Moreover, an incorrect press of the switch will not occur. A surgical procedure can therefore be conducted more safely and reliably. Since excessive cords are excluded, it becomes easy to make preparations or straighten things up.

Figure 71:
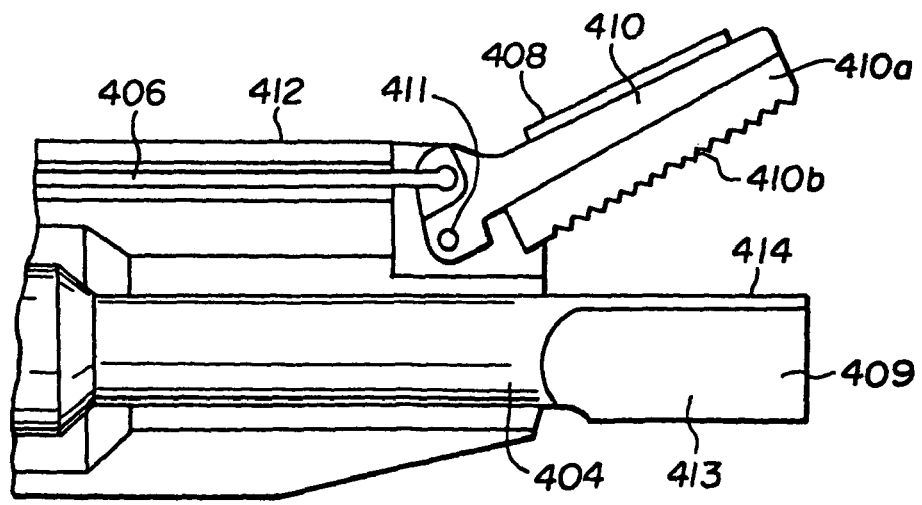
FIG. 71 is a sectional view for explaining the structure of a treatment section of an ultrasound treatment appliance of the twenty-fourth embodiment of the present invention.

Referring to FIG. 71, the twenty-fourth embodiment of the present invention will be described.

This embodiment also attempts to properly perform the on-off operation of ultrasonic oscillations in an ultrasound treatment system according to coagulation or incision of a living tissue.

To be more specific, in this embodiment, as mentioned above, a pressure sensor, for example, a strain gauge 481 is affixed to the holding member 410 of an ultrasound treatment appliance. Owing to this structure, a clamping force can be detected more accurately. When clamping force is applied, the holding member 410 is strained. When the strain reaches a certain value, ultrasonic waves are oscillated in response to a signal indicating the strain.

A pressure sensor may be attached to the holding butt 410a of the holding member 410 or to a holding plane 410b thereof. It is also possible to attach a piezoelectric member to the holding plane 410b in order to sense a pressure. Using the structure for sensing a pressure directly, a clamped state can be detected more reliably than in any other embodiment.

Figure 72:
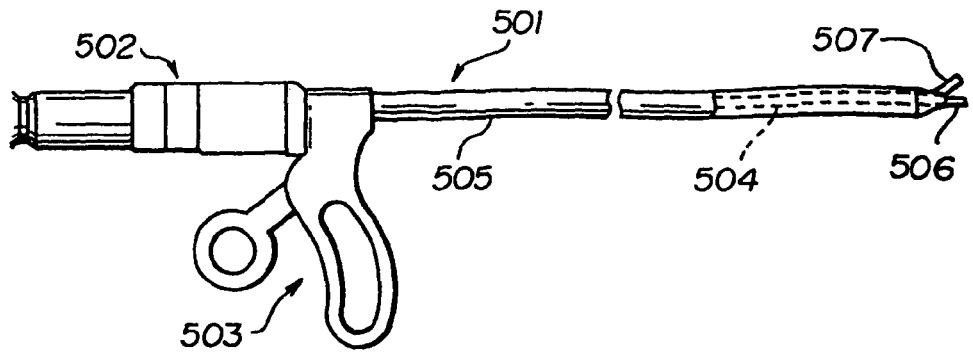
FIGS. 72 to 74 are views showing the twenty-fifth embodiment of the present invention.
Figure 73:
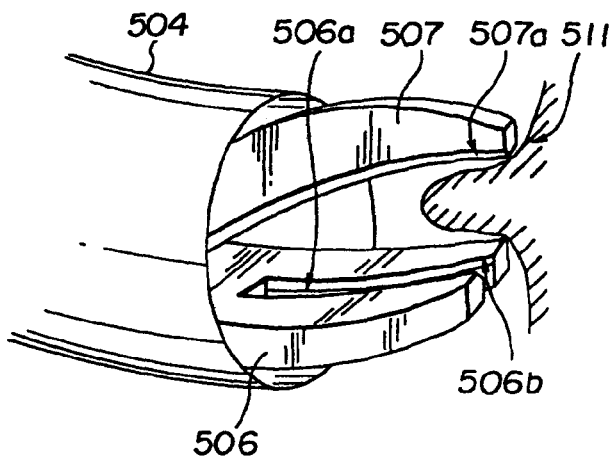
Figure 74:
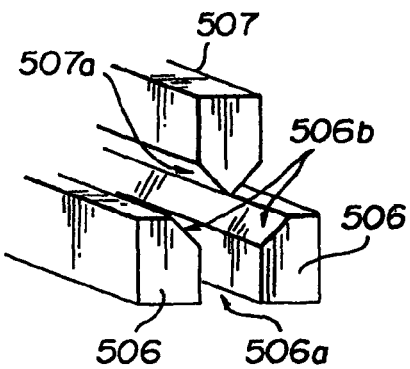

Referring to FIGS. 72 to 74, the twenty-fifth embodiment of the present invention will be described.

As shown in FIG. 72, an ultrasound treatment appliance 501 of this embodiment comprises a grip unit 502 including ultrasonic transducers, an operation unit 503 fixed to the grip unit 502, an elongated ultrasound probe (hereinafter a probe) 504 coupled with the ultrasonic transducers in the grip unit 502 in order to convey ultrasonic vibrations, and a sheath 505 for covering the probe 504. Reference numeral 506 denotes a distal member constituting a stationary section of a treatment unit distal to the probe 504. 507 denotes a holding member constituting a movable section of the treatment unit which is opposed to the distal member 506.

As shown in FIG. 73, the distal member 506 has a slit-like notch 506a in the distal center thereof. The holding member 507 has a width permitting the holding member 507 to intrude into the slit-like notch of the distal member 506.

The tips of the distal member 506 and holding member 507 are curved to facilitate clamping of a living tissue.

As shown in FIG. 74, holding surfaces 507a are formed on the tip of the holding member 507 and holding surfaces 506b are formed on the tip of the distal member 506, so that the holding surfaces 507a and 506a will be opposed to each other. Specifically, the tip of the holding member 507 has a convex part and forms the holding surfaces 507a. The slit-like notch 506a of the distal member 506 serving as a distal member has a concave part and forms the holding surfaces 506b.

Next, the operations of the ultrasound treatment appliance 501 having the foregoing structure will be described.

In FIG. 72, when the operation unit 503 is manipulated, the holding member 507 gradually closes relative to the distal member 506 serving as a distal member. Consequently, a living tissue 511 is clamped. Specifically, at this time, the living tissue 511 is clamped by the holding surfaces 507a of the holding member 507 and the holding surfaces 506a of the distal member 506.

Next, in this state, the ultrasonic transducers incorporated in the grip unit 502 are vibrated. Ultrasonic vibrations stemming from the ultrasonic transducers then propagate the probe 504 and are conveyed to the distal member 506 clamping the living tissue 511. The distal member 506 develops frictional heat due to the ultrasonic vibrations. Thus, the living tissue 511 clamped by the holding member 507 and distal member 506 is coagulated.

Speaking in more detail, the portion of the tissue clamped by the holding surfaces 507a and holding surfaces 506b shown in FIG. 74 is coagulated especially efficiently.

Next, when the grip unit 502 is gripped more intensively, the holding member 507 intrudes into the slit-like notch 506a of the distal member 506 serving as a distal member, and thus incises the living tissue 511.

As mentioned above, in the ultrasound treatment appliance 501 of this embodiment, the holding surfaces 507a of the holding member 507 cooperate with the holding surfaces 506b of the distal member 506 in reliably clamping the living tissue 511. The living tissue 511 is coagulated with frictional heat resulting from ultrasonic vibrations conveyed to the distal member 506. The holding member 507 is intruded into the slit-like notch 506a of the distal member 506 serving as a distal member in order to incise the living tissue 511. The living tissue 511 can therefore be incised reliably even if the living tissue 511 is a ligament containing lots of fibers or the like.

The living tissue 511 is clamped by the holding surfaces 507a of the holding member 507 and the holding surfaces 506a of the distal member 506. The margins of an incision area of the living tissue 511 are then coagulated. Bleeding can therefore be prevented during incision.

Furthermore, since incision and coagulation can be executed on one plane, it becomes possible to shorten a surgery time.

As shown in FIG. 74, in this embodiment, the tip of the holding member 507 has a convex part and forms the holding surfaces 507a. The slit-like notch 506a of the distal member 506 serving as a distal member has a concave part and forms the holding surfaces 506b. The present invention is not limited to this structure but may apply to a reverse structure. Specifically, the tip of the distal member 506 serving as a distal member may have a convex part and form holding surfaces, and a slit-like notch formed in the holding member 507 may have a concave part and form holding surfaces. Even this structure provides the same advantages as those mentioned above.

Moreover, the holding member 507 and the distal member 506 serving as a distal member can be replaced with another ones and are not limited to the foregoing shapes. Furthermore, the distal member 506 serving as a distal member may be shaped as mentioned above by directly machining the probe 504. Even this structure provides the aforesaid advantages.

Figure 75:
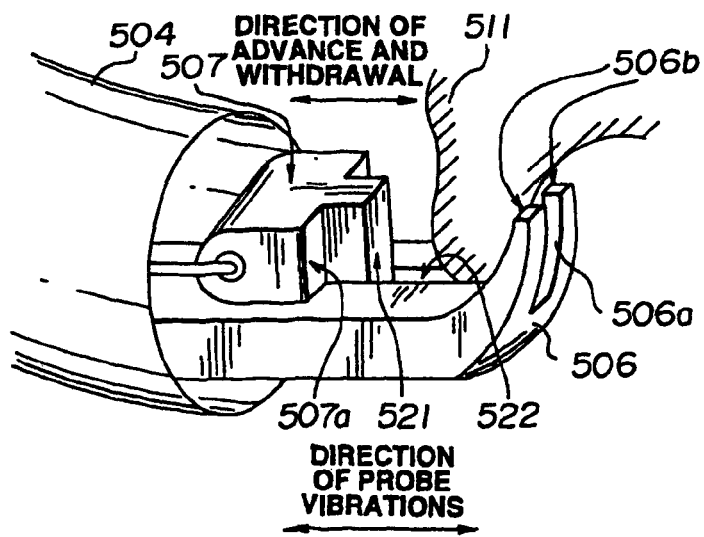
FIG. 75 is a diagram showing the structure of a treatment unit of an ultrasound treatment appliance of the twenty-sixth embodiment of the present invention.

Referring to FIG. 75, the twenty-sixth embodiment of the present invention will be described.

This embodiment is substantially identical to the twenty-fifth embodiment. Only a difference will be described. The same components are assigned the same reference numerals, and the description of the components will be omitted.

As shown in FIG. 75, the holding member 507 is structured so that the holding member 507 can advance or withdraw freely in the same direction as a vibrating direction of the distal member 506. The tip of the holding member 507 on the side of the distal member 506 has a convex part 521. In contrast, the distal member 506 has a concave part 522 serving as a guide for the convex part 521 of the holding member 507. The convex part 521 of the holding member 507 advances or withdraws along the concave part 522 serving as a guide. In this embodiment, holding surfaces 507a are formed on the margins of the convex part 521 of the holding member 507. Holding surfaces 506b are formed on an inner side of the distal member 506 opposed to the holding surfaces 507a. The other components are identical to those in the twenty-fifth embodiment.

In this embodiment, when the operation unit 503 is manipulated, as shown in FIG. 75, the convex part 521 of the holding member 507 advances or withdraws along the concave part 522 serving as a guide. The holding surfaces 507a on the margins of the convex part 521 and the holding surfaces 506b of the distal member 506 having the similar shape as the one in the twenty-fifth embodiment cooperate with each other in clamping the living tissue 511. The living tissue 511 is then coagulated with frictional heat resulting from ultrasonic vibrations conveyed to the distal member 506. The holding member 507 is intruded into the slit-like notch 506a of the distal member 506 serving as a distal member in order to incise the living tissue 511. When the grip unit 502 is gripped further intensively, the convex part 521 of the holding member 507 intrudes into the slit-like notch 506a of the distal member 506 serving as a distal member so as to incise the living tissue 511. The other operations are identical to those of the twenty-fifth embodiment.

As mentioned above, this embodiment has the same advantages as the twenty-fifth embodiment. Moreover, the holding surfaces 507a on the margins of the convex part 521 of the holding member 507 are used to clamp the living tissue 511. Thus, larger holding surfaces can be ensured for clamping the living tissue 511. This results in more reliable coagulation.

Incidentally, the guide for the convex part 521 may be formed on a sheath 505 shown in FIG. 72 but may not be the concave part 522 formed to advance or withdraw the holding member 507.

Figure 76:
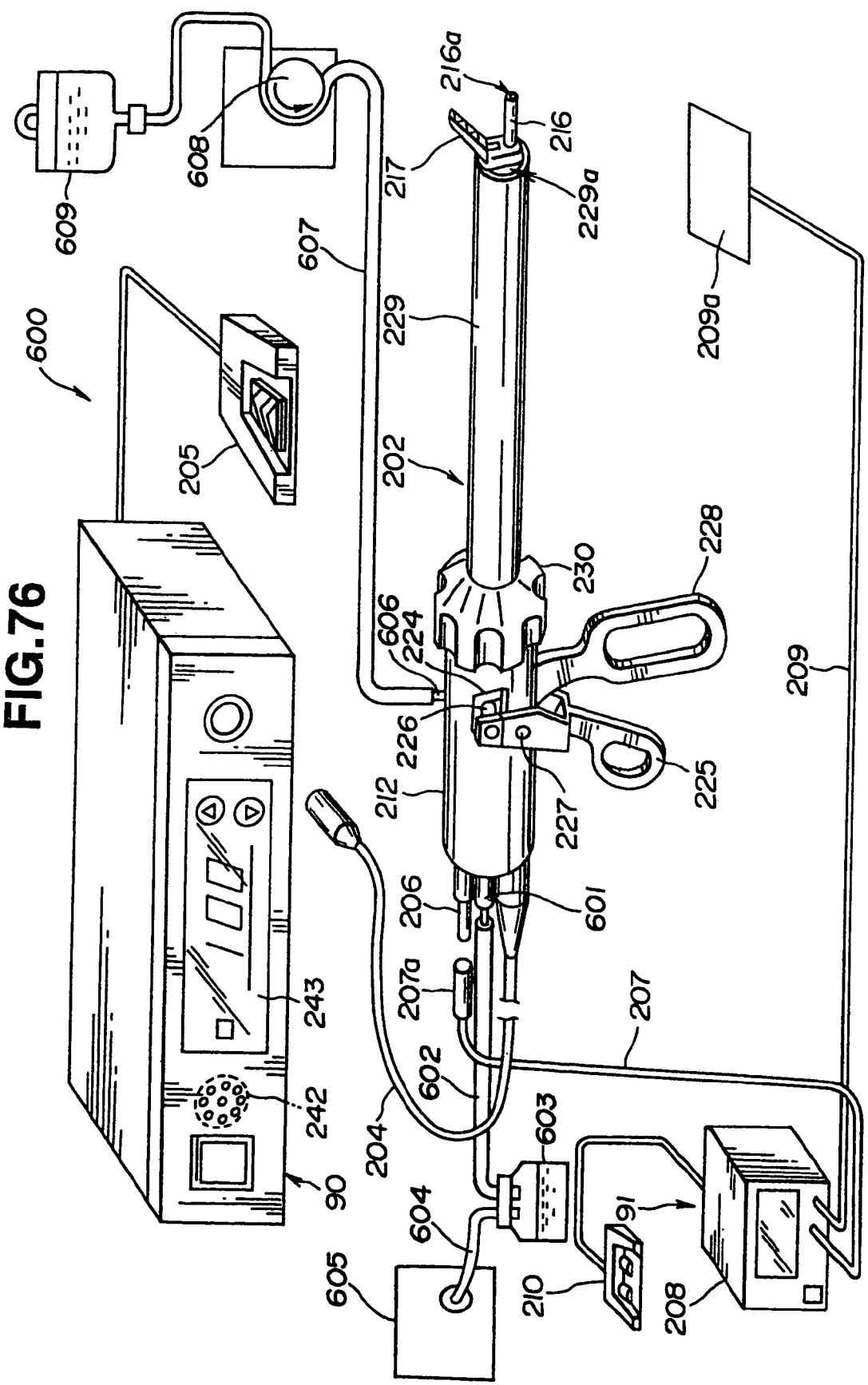
FIG. 76 is a view showing the overall configuration of an ultrasound treatment system of the twenty-seventh embodiment of the present invention.

Referring to FIG. 76, the twenty-seventh embodiment of the present invention will be described.

As illustrated, a probe 216 of an ultrasonic incision/coagulation unit 202, in which transducers for generating ultrasonic vibrations so as to enable coagulation and incision are incorporated, in an ultrasound treatment system 600 of this embodiment is, as shown in FIGS. 38A and 41, formed with a pipe member having a through hole 216a. The through hole 216a bored in the probe 216 communicates with a bore of a suction base 601 jutting from the back end of the transducer cover 212 that is a handpiece by way of through holes bored in the transducers inside the transducer cover 212.

One end of a suction tube 602 is joined with the suction base 601. The other end of the suction tube 602 is connected to a suction pump 605 via a suction vial 603 and communication tube 604.

By the way, a perfusion base 606 is jutting from the outer circumference of the transducer cover 212. One end of a perfusion tube 607 is joined with the perfusion base 606, and the other end thereof is connected to a perfusion tank 609, in which a perfusion fluid such as physiological saline is preserved, by way of a roller pump 608. The bore of the perfusion base 606 communicates with the bore of the sheath 229.

The other components are identical to those in the fourteenth embodiment. The same reference numerals will be assigned to the same members. The description of the members will be omitted.

Since the ultrasound treatment system 600 has the foregoing components, when a living tissue clamped by the probe 216 and holding member 217 is crashed by ultrasonic vibrations, the suction pump 605 is driven so that the crashed tissue can be sucked through the through hole 216a of the probe 216 and evacuated to the suction vial 603. Moreover, when the roller pump 608 is driven, the perfusion fluid such as physiological saline preserved in the perfusion tank 609 can be jetted to a region to be treated or the like through a distal opening 229a by ways of the bore of the sheath 229.

An ultrasonic coagulation/incision function and suction function make it possible to continuously carry out the sequential work of exposing a blood vessel and then coagulating or incising the blood vessel or a tissue. This contributes to improvement of maneuverability and a great decrease in surgical operation time.

The twenty-eighth embodiment of the present invention will be described with reference to FIG. 77 to FIG. 84.

This embodiment relates to a handpiece 601 of an ultrasonic incision/coagulation system that is an example of ultrasound treatment systems. The handpiece 601 includes an external unit 604 and an internal unit 605 shown in FIG. 78A. The internal unit 605 is mounted in the external unit 604 so that the internal unit 605 can be dismounted freely.

Figure 78A:
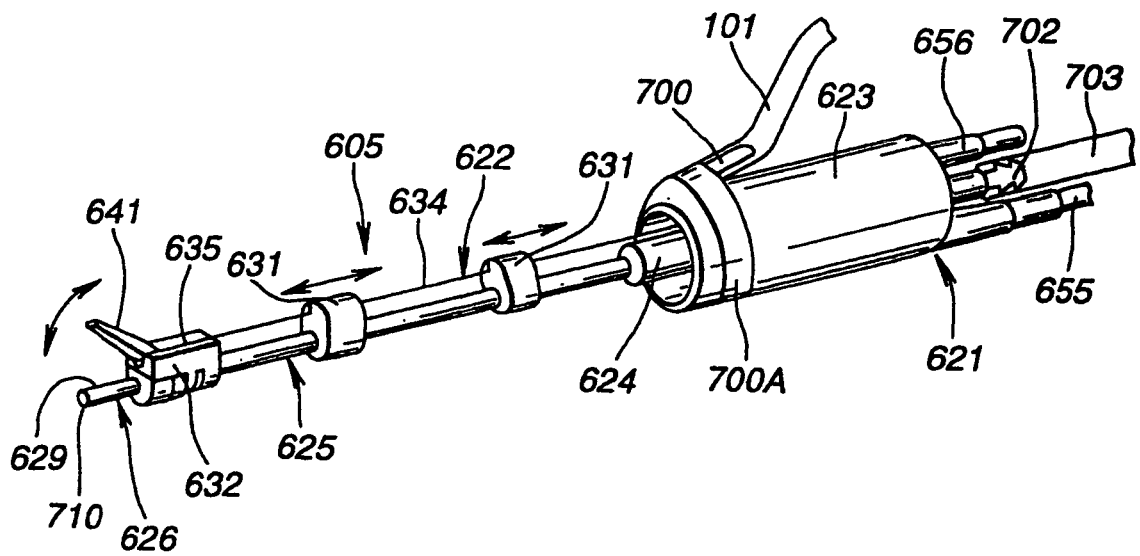
FIG. 78A is an oblique view showing an internal unit of the handpiece of the ultrasonic incision/coagulation system.
Figure 78B:
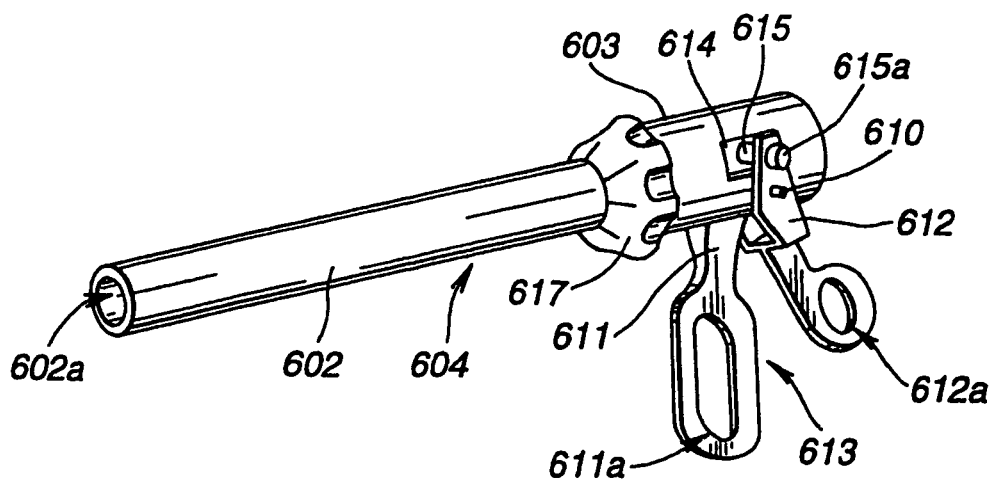
FIG. 78B is an oblique view showing an external unit of the ultrasonic incision/coagulation system.

Moreover, the external unit 604 is, as shown in FIG. 78B, composed of an elongated cylindrical insertion-unit sheath 602 and a cylindrical holding-unit sheath 603. The insertion-unit sheath 602 serves as an insertion unit protecting member, and the holding-unit sheath 603 is attached to the proximal end of the insertion-unit sheath 602. Furthermore, the holding-unit sheath 603 is provided with a clamping member operating means 613 composed of a stationary handle 611 and movable operation handle 612.

The stationary handle 611 is fixed to the holding-unit sheath 603, while the movable operation handle 612 is pivoted to the holding-unit sheath 603 using a pin 610. Furthermore, the stationary handle 611 and movable operation handle 612 have finger-rest ring portions 611a and 612a respectively.

Figure 81A:
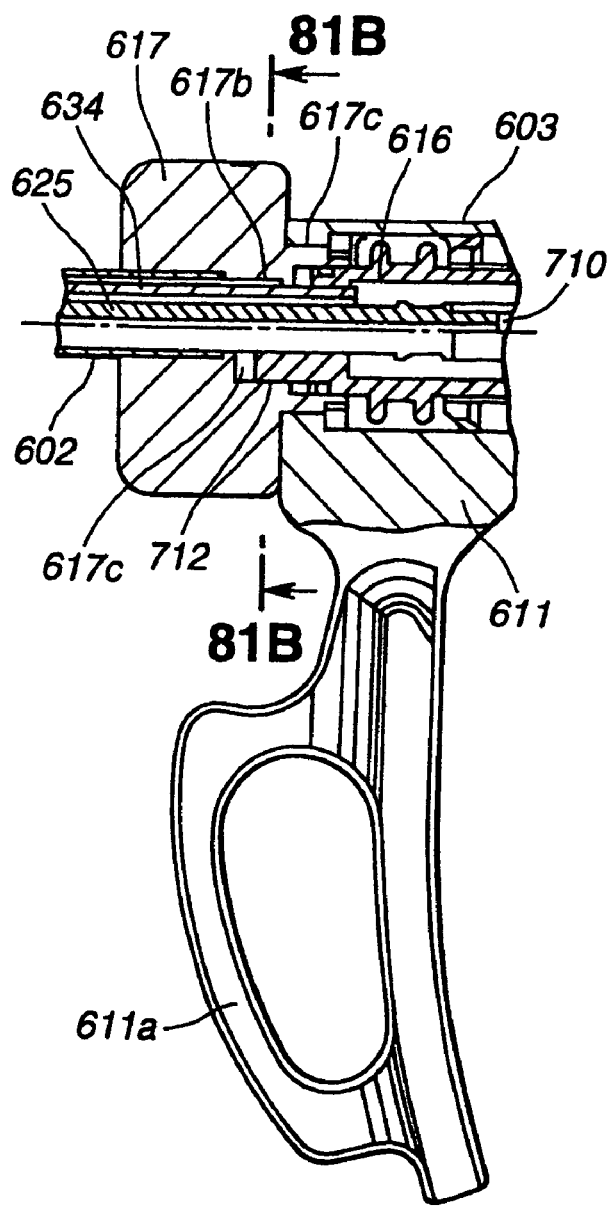
FIG. 81A is a longitudinal sectional view showing major components located near a stationary handle included in the external unit of the handpiece of the ultrasonic incision/coagulation system.

Moreover, a turning knob 617 is, as shown in FIG. 81A, fixed to the proximal part of the insertion-unit sheath 602. A cylindrical coupling portion 617a is projected from the back end of the turning knob 617. Furthermore, the distal end of the holding-unit sheath 603 is coupled to the coupling portion 617a of the turning knob 617 so that the turning knob 617 can be turned freely. The proximal part of the insertion-unit sheath 602 is attached to the holding-unit sheath 603 via the coupling portion 617a of the turning knob 617, so that the insertion-unit sheath 602 can be freely turned about the axis of the holding-unit sheath 603. The turning knob 617 realizes an operating means for turning the insertion-unit sheath 602 about the axis of the holding-unit sheath 603.

Moreover, the internal unit 605 includes an ultrasonic transducer unit 621 and a clamping member unit 622. The ultrasonic transducer unit 621 has an ultrasonic transducer that is not shown, a horn 624, and a probe 625 serving as a vibration transmitting member. The ultrasonic transducer is locked in a cover sheath 623 of the handpiece 601. Furthermore, an ultrasonic treatment portion 626 is formed as the distal part of the probe 625 ultrasonic vibrations generated by the ultrasonic transducer are intensified by the horn 624 and transmitted to the ultrasonic treatment portion 626 that is the distal part of the probe 625.

Titanium, aluminum, or an alloy thereof that offers an excellent acoustic effect and has a superb nature acceptable by a living body is often made into the horn 624 for transmitting vibration generated by the ultrasonic transducer, and the probe 625.

Figure 80:
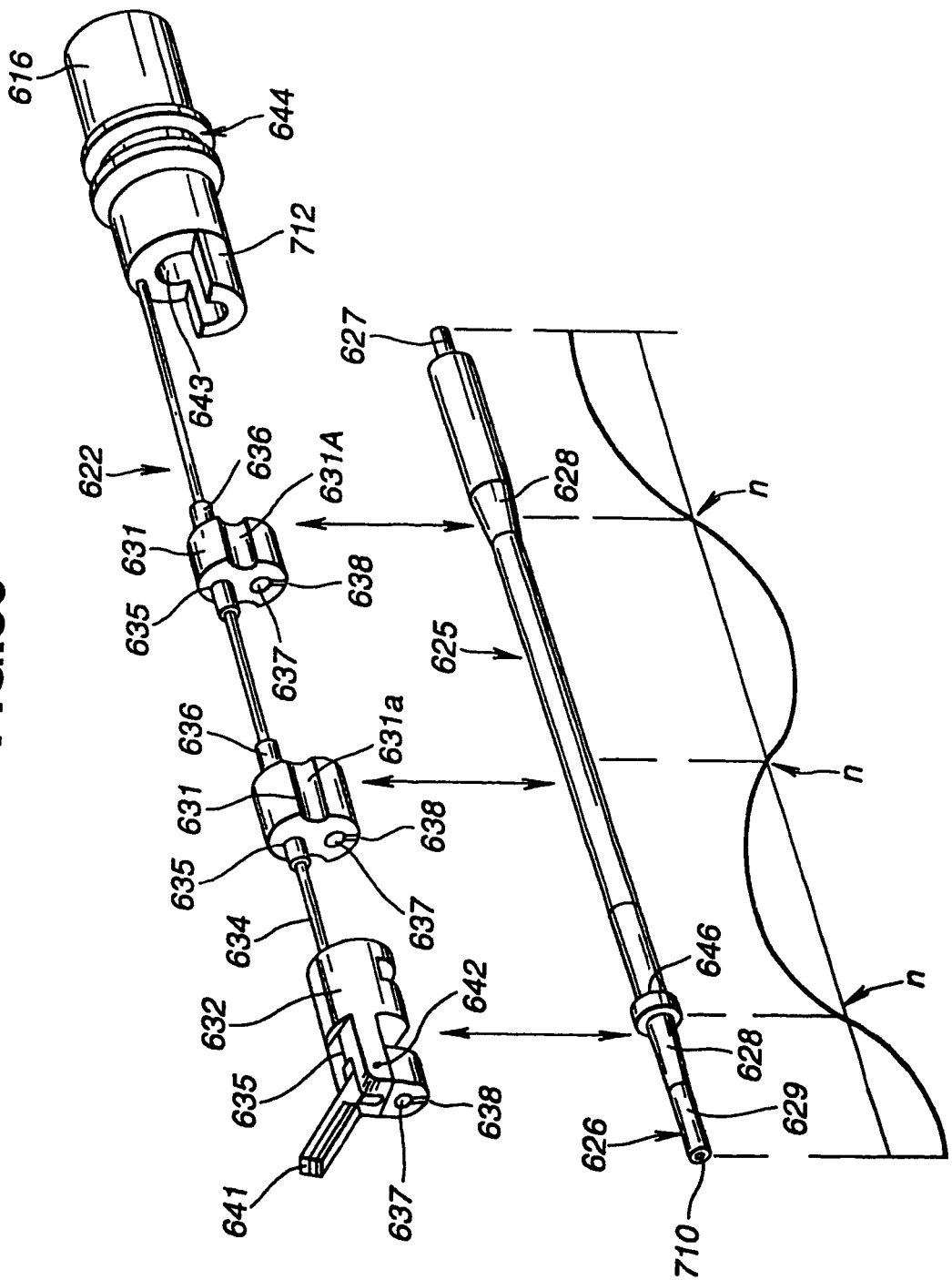

Moreover, a screw 627 is, as shown in FIG. 80, threaded in the proximal part of the probe 625. Using the screw 27, the proximal part of the probe 625 is screwed to the distal part of the horn 624. The probe 625 serving as a vibration transmitting member is realized with a substantially straight rod having a tapered horn 628 formed as an integral part thereof but not having a stepped portion or a groove-like small-diameter portion. Owing to this structure, the probe 625 enjoys intensified strength.

Moreover, the slender ultrasonic treatment portion 626 is formed as the extremely distal part of the probe 625. The ultrasonic treatment portion 626 is a portion serving as a stationary blade 629. The stationary blade 629 may be a blade having a round cross section. Preferably, the stationary blade 629 should be made available in various shapes, such as, a rectangular blade having a narrow width, an elliptic blade, and a triangular blade. This is preferred from the viewpoint of improving treatment efficiency and designing a treatment work unit compactly. Moreover, blades having various shapes or forms other than the round blade are often adopted to balance the operation of incision and the operation of coagulation.

Incidentally, the stationary blade 629 may not be formed as an integral part of the probe 625 but may be formed as a separate member. The separate member may be coupled to the probe 625 using a screw or the like, so that the stationary blade 629 can be replaced with another stationary blade 629 having a different shape.

Figure 79A:
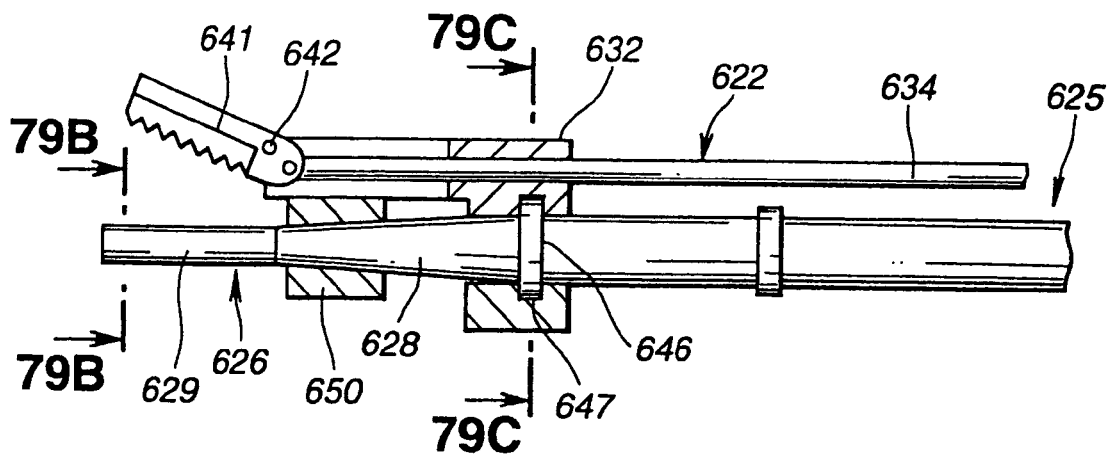
FIG. 79A is a longitudinal sectional view showing the distal part of the internal unit included in the handpiece of the ultrasonic incision/coagulation system.
Figure 79B:
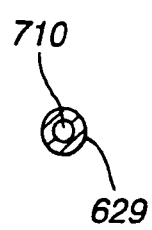
FIG. 79B is a 79B-79B sectional view of the distal part shown in FIG. 79A.

Moreover, the clamping member unit 622 has, as shown in FIG. 79A, a metallic movable blade (clamping member) 641 and an operation rod 634 (clamping member driving means). The movable blade 641 is opposed to the stationary blade 629, and serves as a jaw that clamps a living tissue in cooperation with the stationary blade 629 or frees the living tissue. The operation rod 634 serves as an operation force transmitting member for driving the movable blade 641 to open or close it.

Furthermore, the clamping member unit 622 has, as shown in FIG. 80, a plurality of spacers 631 arranged at nodes n of ultrasonic vibrations. A clamping member support base 632 that is one spacer is located at the position of the extremely distal node n of ultrasonic vibrations in the probe 625.

Moreover, a groove 635 in which the operation rod 634 is fitted and retained is cut in the top of each spacer 631. An outer locking member 636 formed with a small-diameter pipe is, as shown in FIG. 60, fitted in each groove 635. The operation rod 634 is inserted into the outer locking members 636 and immobilized. In other words, the operation rod 634 is fitted along the axes of the spacers 631 in the spacers 631 other than the clamping member support base 632 that is the extremely distal spacer.

The spacers 631 should merely retain the operation rod 632 for fear the operation rod may be displaced from the positions of the nodes n of ultrasonic vibrations in the probe 625. An alternative attaching means for the spacers 631 is such that the spacers 631 are fixed to the operation rod 634 directly or via the outer locking members 636. Alternatively, a locking means may be adopted so that the spacers 631 will not be fixed to the operation rod 634 but will be merely retained at the positions of the nodes of ultrasonic vibrations so as not to be displaced therefrom. The spacers 631 are thus positioned and fixed to the operation rod 634. This obviates the necessity of creating concave and convex parts, which are used for positioning the spacers 631, in the probe 635. This results in the simpler structure and reduced costs. Moreover, the strengths of the probe 625 and spacers 631 can be improved.

Moreover, a through hole 637 in which the probe 625 is inserted and retained, and an attachment/detachment slit 638 are formed in the lower part of each spacer 631. The probe 625 is inserted into the through holes 637 so that it can slide along the axes thereof. The spacers 631 are made of a fluoroplastic material offering excellent sliding smoothness, such as, so-called Teflon (polytetrafluoroethylene), and thus formed as members that rub against the probe 625.

Moreover, the proximal end of the movable blade 641 is pivoted to the clamping member support base 632, which is the extremely distal spacer, using a pin 642. Moreover, the distal part of the operation rod 634 is coupled to the proximal part of the movable blade 641 so that the operation rod 634 can be turned freely.

Moreover, a sliding cylinder 616 shown in FIG. 80 is coupled to the proximal end of the operation rod 634. The sliding cylinder 616 is inserted into the holding-unit sheath 603 so that the sliding cylinder 616 can freely slide back and forth. A passage hole 643 through which the probe 625 is passed is bored in the axial center of the sliding cylinder 616.

Moreover, an annular groove 644 by which the sliding cylinder 616 is coupled to the movable operation handle 612 is cut in the outer circumference of the sliding cylinder 616. Windows 614 through which the movable operation handle is coupled are located on both sides of the flank of the holding-unit sheath 603. Locking pins (locking members) 615 piercing the distal parts of the movable operation handle 612 are inserted through the windows 614. Furthermore, the distal ends of the locking pins 615 are fitted and locked in the annular groove 644 of the sliding cylinder 616. When the movable operation handle 612 is turned with the pin 610 as a center, the sliding cylinder 616 is slid back and forth by means of the locking pins 615. The operation rod 634 is slid back and forth together with the sliding cylinder 616. This causes the movable blade 641 opposed to the stationary blade 629 to open or close.

The locking pins 615 are screwed to the distal parts of the movable operation handle 612. By turning the heads 615a of the locking pins 615, the tips of the locking pins 615 are jutted to be fitted in the annular groove 644 of the sliding cylinder 616. On the contrary, the tips of the locking pins 615 are withdrawn to be freed from the annular groove 646 of the sliding cylinder 616.

Moreover, the movable blade 641 has, as shown in FIG. 82 and FIG. 83A, a curved surface 652 formed on its side coming into contact with the stationary blade 629 of the probe 625. The curved surface 652 comes into contact, directly with the stationary blade 629. The curved surface 652 should preferably be designed to have its contour varied depending on the shape of the stationary blade 629. Furthermore, the movable blade 641 has wavy tooth-like portions 654 formed on both sides of the curved surface 652 that comes into direct contact with the stationary blade 629. The tooth-like portions help the movable blade 641 and stationary blade 629 to clamp living tissue reliably. The curved surface 652 of the movable blade 641 and the tooth-like portions 652 should preferably be made of Teflon (polytetrafluoroethylene) or any other material offering excellent sliding smoothness.

Figure 79C:
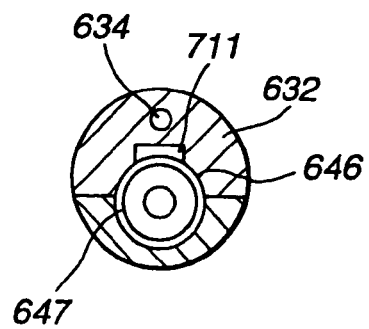
FIG. 79C is a 79C-79C sectional view of the distal part shown in FIG. 79A.

Moreover, a circular flange 646 is formed at the position of the extremely distal node n of ultrasonic vibrations in the distal part of the probe 625. A fitting groove 647 shaped in line with the flange 646 is cut in the lower inner surface of the clamping member support base 632 that is the extremely distal spacer for supporting the movable blade 641. As shown in FIG. 79C, the flange 646 is fitted and locked in the fitting groove 647 of the clamping member support base 632. The probe 625 is therefore held in the clamping member support base 632 to be turnable.

The clamping member support base 632 is therefore mounted so that it can be turned about the axis of the probe 652 together with the insertion-unit sheath 602. The orientation of the stationary blade 629 relative to the movable blade 641 may assume any angle within 360°. The movable blade 641 can be turned for use so that it can be used easily by an operator.

Figure 81B:
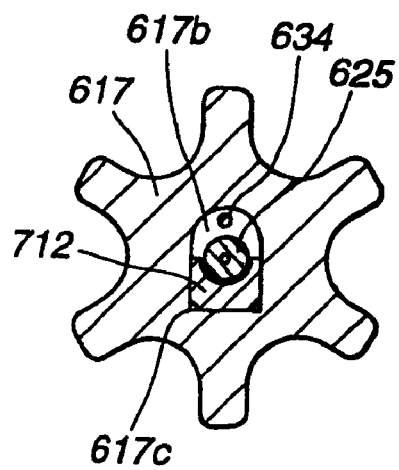
FIG. 81B is a 81B-81B sectional view of the major components shown in FIG. 81A.

Moreover, as shown in FIG. 81A, a projecting portion 712 is projecting from one side of the distal end of the sliding cylinder 616 with respect to the center axis of the sliding cylinder 616. An axial center hole 617b is, as shown in FIG. 81B, bored in the axial center of the turning knob 617. The probe 625 and operation rod 634 are passed through the axial center hole 617b. Furthermore, a fitting groove 617c shaped in line with the projecting portion 712 of the sliding cylinder 616 is cut in one side of the axial center hole 617b. The projecting portion 712 of the sliding cylinder 616 is fitted into the fitting groove 617c of the turning knob 617, thus preventing the sliding cylinder 616 and turning knob 617 from relatively turning about the axes thereof. The projecting portion 712 of the sliding cylinder 616 is turned while fitted in the fitting groove 617c of the turning knob 617. All turnable components except the insertion-unit sheath 602 and the probe 625 included in the internal unit 605 can therefore be turned simultaneously.

Furthermore, as shown in FIG. 83B, a locking end surface 648 that is substantially flat is formed as the bottom of the clamping member support base 632. The locking end surface 648 is locked with an anti-turn member 649 fixed to the inner surface of the insertion-unit sheath 602. When the insertion-unit sheath 602 and clamping member support base 632 are turned about the axes thereof, they turn together with the locking member for the turning knob 617. The internal unit 605 will therefore not be twisted.

Moreover, an anti-swing member 650 made of a material permitting smooth sliding, such as, so-called Teflon (polytetrafluoroethylene) is formed as an integral part of the clamping member support base 632. This is intended to prevent the stationary blade 629 of the probe 625 from swinging. The anti-swing member 650 bears a horn 628 formed as the distal part of the probe 625, and prevents a warp.

Moreover, in this embodiment, a through hole 710 is bored along the axial centers of the ultrasonic transducer, horn 624, and probe 625 included in the ultrasonic transducer unit 621. Furthermore, a suction base 702 communicating with the through hole 710 is jutted from the back end of the ultrasonic transducer unit 621. One end of a suction tube 703 is coupled to the suction base 702.

Moreover, a ring-shaped channel coupling member 700A is mounted on the outer circumference of the distal part of the cover sheath 623 so that the channel coupling member 700A can be turned. A liquid is supplied to the lumen of a cover sheath 623 through the channel coupling member 700A. A perfusion base 700 is jutted from the channel coupling member 700A. One end of a perfusion tube 701 is coupled to the perfusion bass 700.

Furthermore, a penetrating perfusion hole is bored in the cover sheath 623 inside the channel coupling member 700A. A liquid supplied over the perfusion tube 701 is fed into the channel coupling member 700A through the perfusion base 700. The liquid is then supplied to the inside of the cover, sheath 632 through the perfusion hole bored inside the channel coupling member 700A.

Moreover, a perfusion channel is formed between the insertion-unit sheath 602 and probe 625. Herein, a groove 631a for creating a path is, as shown in FIG. 80, cut in the flank of each spacer 631. Supply of a liquid is thus carried out smoothly. Furthermore, a key groove 711 is, as shown in FIG. 79C, penetrating through the clamping member support base 632. This helps a perfusive liquid to flow smoothly.

FIG. 84 shows, similarly to FIG. 76, the outline overall configuration of an ultrasonic incision/coagulation system. In FIG. 84, there are shown an ultrasonic treatment power supply apparatus 721 and a high-frequency treatment power supply apparatus 714.

Figure 77:
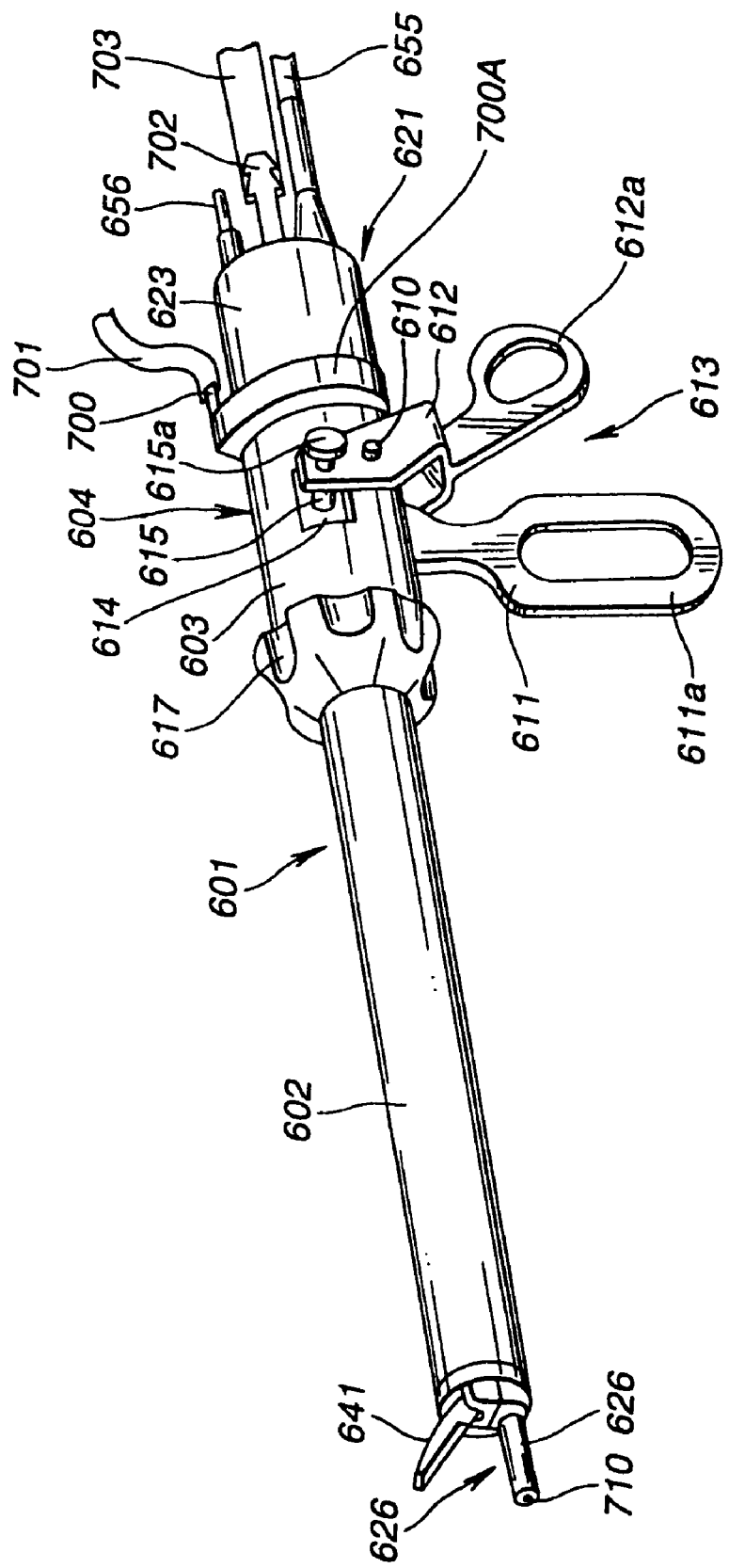

Moreover, ends of an ultrasonic driving power cord 655 and high-frequency treatment power cord 656 which are shown in FIG. 77 are coupled to the back end of the handpiece 601. The other end of the ultrasonic driving power cord 655 is connected to the ultrasonic treatment power supply apparatus 721. The other end of the high-frequency treatment power supply cord 656 is spliced to a power cord 713 extending from the high-frequency treatment power supply apparatus 714. A foot switch 722 used to control ultrasonic waves is connected to the ultrasonic treatment power supply apparatus 721. A foot switch 718 used to control a high-frequency voltage is connected to the high-frequency treatment power supply apparatus 714. Furthermore, a counter electrode plate 720 is connected to the high-frequency treatment power supply apparatus 714 over a lead 719.

As shown in FIG. 84, the other end of the perfusion tube 701 coupled to the perfusion base 700 of the handpiece 601 is coupled to a perfusion tank 724 via a roller pump 723. Physiological saline or any other perfusive liquid is reserved in the perfusion tank 724. Thus, a perfusing means is realized. Specifically, when the roller pump 723 is driven, physiological saline or the like in the perfusion tank 724 is supplied over the perfusion channel created between the insertion-unit sheath 602 and probe 625.

Furthermore, the other end of the suction tube 703 coupled to the suction base 702 is coupled to a suction pump 716 by way of a suction bin 715 and communication tube 717. Thus, a sucking means is realized. Specifically, a living tissue crushed by ultrasonic violations is sucked over the through hole 710 of the probe 625 by driving the suction pump 716, and discharged into the suction bin 715.

Next, a description will be made of the operations of the ultrasonic incision/coagulation system having the foregoing components.

When the ultrasonic incision/coagulation system of this embodiment is in use, the movable operation handle 612 pivots with the pin 610 as a center relative to the stationary handle 611. This causes the movable blade 641, which is opposed to the stationary blade 629 that is the extremely distal part of the probe 621, to open dr close. A living tissue is clamped by the stationary blade 629 and movable blade 641, and crushed by ultrasonic vibrations. At this time, the suction pump 716 is driven in order to suck the crushed living tissue over the through hole 710 of the prove 625. The crushed living tissue can then be discharged into the suction bin 715.

Moreover, when the roller pump 723 is driven, physiological saline or any other perfusive liquid reserved in the perfusion tank 724 is supplied to the inside of the cover sheath 623 via the suction tube 701, suction base 700, and channel coupling member 700A. The liquid can be jetted out through a distal opening 602a of the insertion-unit sheath 602 over the lumen of the insertion-unit sheath 602, and perfused to a region to be treated.

The ultrasonic incision/coagulation system having the foregoing components provides the advantage described below.

Specifically, in this embodiment, the roller pump 723 is driven for treating a living tissue ultrasonically. Thus, physiological saline or the like is supplied from the perfusion tank 724 over the perfusion channel lying between the insertion-unit sheath 602 and prove 625 by way of the perfusion tube 701. Assume that a living tissue is clamped by the stationary blade 629 that is the extremely distal part of the prove 625 and the movable blade 641 and then crushed by ultrasonic vibrations. In this case, blood or a fatty tissue can be prevented from flowing between the insertion-unit sheath 602 and prove 625. At this time, the inflow of blood or a fatty tissue can be prevented by the flow of physiological saline or any other perfusive liquid supplied over the perfusion channel created between the insertion-unit sheath 602 and probe 625. A rise in the impedance of the probe 625 can be suppressed. Besides, smooth ultrasonic driving can be realized but the resonant frequency characteristic will not be disordered. Eventually, deterioration in a treating ability can be prevented.

Furthermore, it can be prevented that when the probe 625 of the ultrasonic incision/coagulation system is vibrated ultrasonically, the probe 625 oscillates at any frequency other than a predetermined frequency. It can therefore be prevented that an unbearable abnormal sound occurs during ultrasonic treatment. Consequently, high-efficiency ultrasonic driving can be realized, and deterioration in a treating ability can be prevented.

Moreover, regions surrounding the ultrasonic treatment portion can be cooled efficiently with physiological saline or any other perfusive liquid jetted out over the lumen of the insertion-unit sheath 602. A coagulated range of a living tissue can be confined to an operator's intended area. This contributes to improvement in maneuverability and a drastic decrease in the time required for a surgery. Nevertheless, it will not take place that a nervous tissue is injured thermally.

Furthermore, for treating a living tissue ultrasonically, the living tissue is clamped by the stationary blade 629 that is the extremely distal part of the probe 625 and the movable blade 641. The living tissue is crushed by ultrasonic vibrations. At this time, the suction pump 716 is driven in order to suck the crushed living tissue over the through hole 710 of the probe 625 and discharge it outside. The living tissue sucked into the through hole 710 of the probe 625 can therefore be discharged smoothly. Consequently, a rise in the impedance of the probe 625 can be suppressed and high-efficiency ultrasonic driving can be realized. Eventually, deterioration in a treating ability can be prevented.

Moreover, the function of perfusion or suction may be used in combination with ultrasonic coagulation in order to coagulate or incise a living tissue of an intended region. In this case, the sole employment of the handpiece 601 of this embodiment makes it possible to carry out a series of work steps uninterruptedly without the necessity of changing treatment appliances. The series of work steps includes steps of peeling and exposing the living tissue, emulsifying it, crushing it, sucking it, and then discharging it to outside the body. Incidentally, when the series of work steps is carried out in order to coagulate or incise a living tissue, if a plurality of treatment appliances must be changed during surgery, it is annoying. The employment of the handpiece 601 omits the annoying work of changing treatment appliances during surgery. Consequently, the maneuverability of the ultrasonic incision/coagulation system can be further improved and the time required for surgery can be drastically shortened.

Moreover, in this embodiment, the ring-shaped channel coupling member 700A is fitted on the holding-unit sheath 603 of the handpiece 601 to be turnable. The perfusion base 700 is projected from the channel coupling member 700A. The position at which the perfusion tube 701 and perfusion base 700 are coupled to each other can be shifted to any position along the circumference of the holding-unit sheath 603. The perfusion tube 701 can therefore be moved to a position at which it will not interfere with user's manipulations during ultrasonic treatment. Consequently, the ease-of-use of the handpiece 601 can be further improved.

Figure 85:
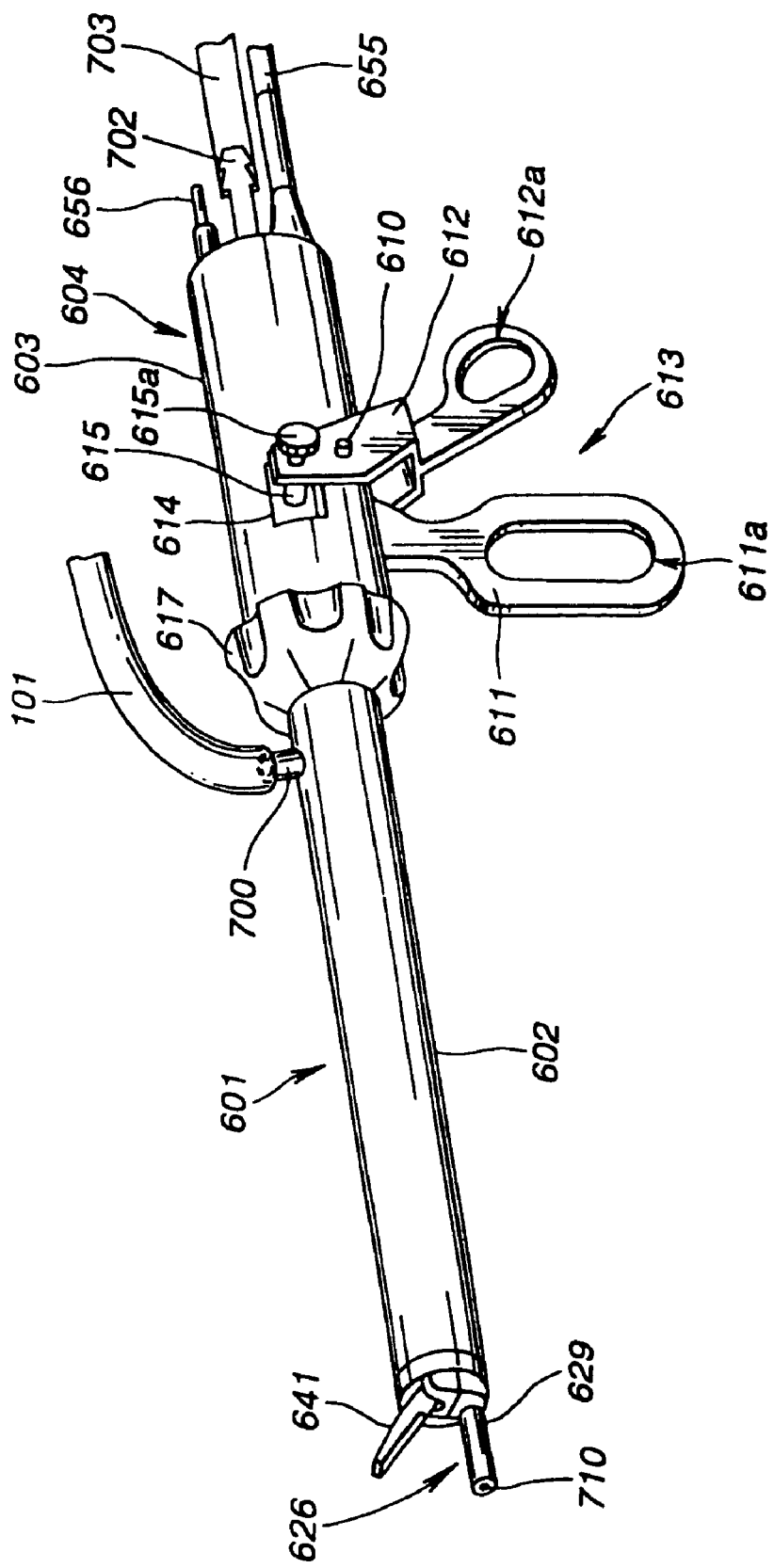
FIG. 85 is an oblique view showing a handpiece of the ultrasonic incision/coagulation system in accordance with the twenty-ninth embodiment of the present invention.

Moreover, the twenty-ninth embodiment of the present invention will be described with reference to FIG. 85.

In this embodiment, the handpiece 601 of the ultrasonic incision/coagulation system of the twenty-eighth embodiment has been modified as described below.

Specifically, the perfusion base 700 is projected from the insertion-unit sheath 602 of the handpiece 601 of the twenty-eighth embodiment. An end of the perfusion tube 701 is coupled to the perfusion base 700. The other components are identical to those of the handpiece 601 of the twenty-eighth embodiment. The same reference numerals will be assigned to the identical components. The description of the components will be omitted.

In this embodiment, the holding unit of the handpiece 601 has a simpler structure than that of the handpiece 601 of the twenty-eighth embodiment. Specifically, in the twenty-eighth embodiment, the ring-shaped channel coupling member 700A is fitted on the holding-unit sheath 603 of the handpiece 601 to be turnable. The perfusion base 700 is projected from the channel coupling member 700A.

Figure 86:
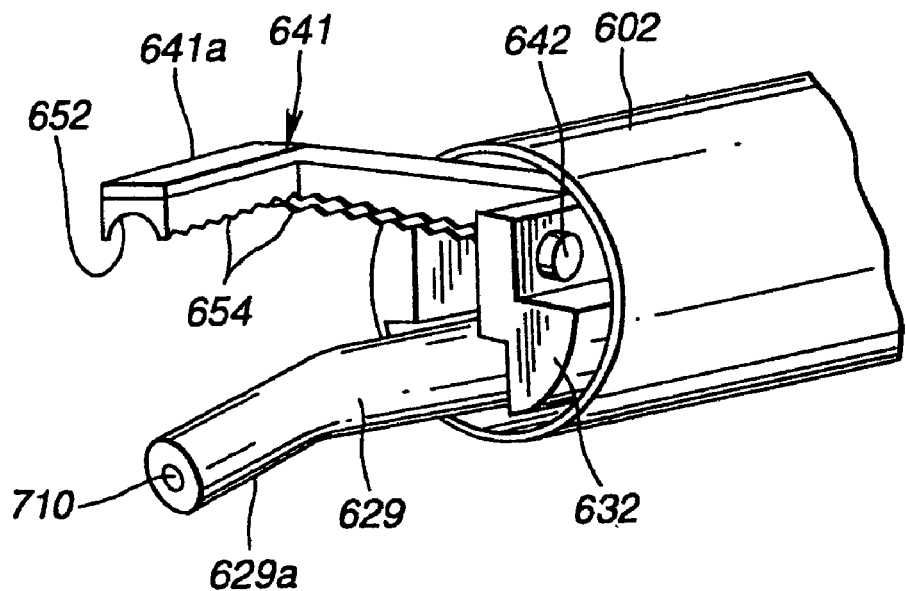

The thirtieth embodiment of the present invention will be described with reference to FIG. 86.

In this embodiment, the handpiece 601 of the ultrasonic incision/coagulation system of the twenty-eighth embodiment, has been modified as described below.

Specifically, the distal part of the stationary blade 629 is formed as a curved portion 629a that is curved obliquely relative to the center line of the stationary blade 629. The stationary blade 629 is the ultrasonic treatment portion 626 that is the extremely distal part of the probe 625 included in the handpiece 601 of the twenty-eighth embodiment. The distal part of the movable blade 641 is formed as a curved portion 641a curved in the same direction as the curved portion 629a of the stationary blade 629. The other components are identical to those of the handpiece 601 of the twenty-eighth embodiment. The same reference numerals will be assigned to the identical components. The description of the components will be omitted.

In this embodiment, the distal parts of the stationary blade 629 and movable blade 641 of the handpiece 601 are formed as the curved portions 629a and 641a respectively that are curved in the same direction. This is helpful in facilitating the work of clamping or peeling a living tissue by means of the stationary blade 629 that is the extremely distal part of the probe 625 and the movable blade 641.

Figure 87:
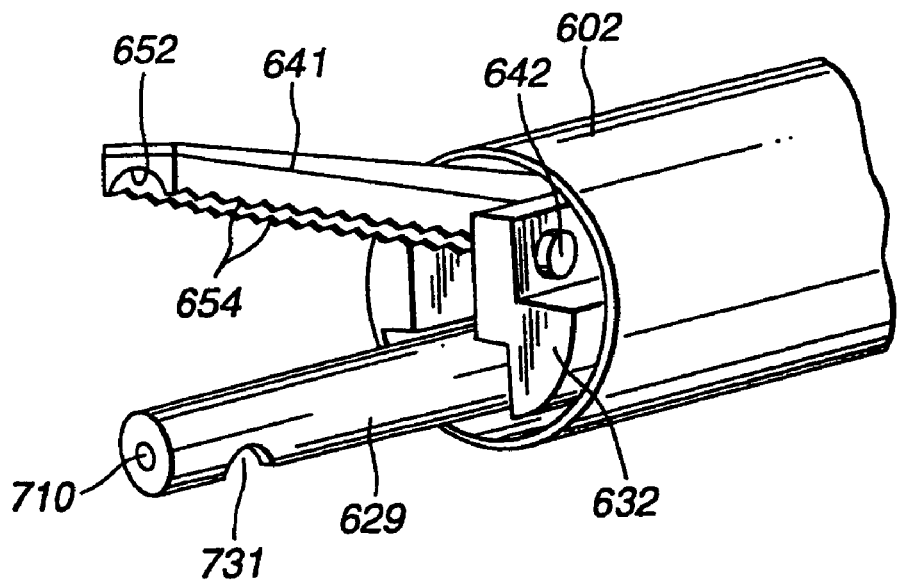

The thirty-first embodiment of the present invention will be described with reference to FIG. 87.

In this embodiment, the handpiece 601 of the ultrasonic incision/coagulation system of the twenty-eighth embodiment has been modified as mentioned below.

Specifically, a notch 731 that is a notched portion of the outer circumference of the probe 625 is formed in the distal part of the stationary blade 629. The stationary blade 629 is the extremely distal ultrasonic treatment portion 626 of the probe 625 included in the handpiece 601 of the twenty-eighth embodiment. The other components are identical to those of the handpiece 601 of the twenty-eighth embodiment. The same reference numerals will be assigned to the identical components. The description of the components will be omitted.

In this embodiment, the work of resection can be carried out by immobilizing a living tissue using the notch 731 of the stationary blade 629 of the probe 625 included in the handpiece 601. This results in a further increase in the number of kinds of treatments that can be conducted by employing the handpiece 601 of this embodiment. The frequency of the work of changing treatment appliances during surgery can be further reduced. This contributes to further improvement in maneuverability and a drastic reduction in the time required for surgery.

In the present invention, it will be apparent that a large range of different embodiments can be formed on the basis of the invention without any departure from the spirit and scope of the invention. This invention will be limited to the appended claims but not restricted to any specific embodiments.

What is claimed is:

1. An ultrasound treatment system to clamp living tissue, the system comprising:
   an ultrasonic transducer for generating ultrasonic vibrations, the ultrasonic transducer having a first through hole bored therein;
   a probe having a distal portion and a proximal portion, the probe having a second through hole bored therein, the probe having a distal opening at the distal portion and a proximal opening at the proximal portion which form parts of the second through hole respectively, the probe being coupled to the ultrasonic transducer to transmit the ultrasonic vibrations to the distal portion of the probe, and the first through hole communicating with the second through hole via the proximal opening when the probe is connected to the ultrasonic transducer;
   a clamp provided to be movable relative to the probe to clamp the living tissue with the distal portion of the probe, the distal opening being provided in the probe spaced apart from a predetermined area on the probe, the predetermined area located to clamp the living tissue with the clamp;
   a handle for operating the clamp; and
   an actuating member coupled to the clamp, the actuating member actuating the clamp in response to the operation of the handle;
   wherein the distal portion includes a distal end, the distal end includes an end surface, and the distal opening is located on the end surface;
   wherein the distal opening of the second through hole is located away from the predetermined area, whereby suction continues as the distal opening remains open even while the living tissue is clamped by the clamp and the distal portion of the probe, and the distal opening sucks the living tissue emulsified or crushed by the treatment of the distal opening and the end surface;
   wherein the predetermined area extends along a longitudinal direction of the probe and includes a side surface of the distal portion of the probe;
   wherein the probe includes a first treatment portion to hold the living tissue between the side surface and the clamp; and
   wherein the probe includes a second treatment portion located on the end surface which is positioned further towards a distal end of the probe than the first treatment portion and the second treatment portion includes the distal opening provided on the end surface.

2. An ultrasound treatment system according to claim 1, wherein the distal portion of the probe is of a curve shape.

3. An ultrasound treatment system according to claim 1, wherein the clamp is deformed so as to match the shape of the distal portion of the probe.

4. An ultrasound treatment system according to claim 1, wherein the probe has a notch formed at the distal portion thereof.

5. An ultrasound treatment system according to claim 4, wherein the notch is formed at the distal portion of the probe spaced apart from the predetermined area on the probe.

6. An ultrasound treatment system according to claim 1, further comprising:
   a base coupled to the first through hole.

7. An ultrasound treatment system according to claim 6, further comprising:
   a suction pump connected to the base.

8. An ultrasonic treatment system according to claim 1, further comprising:
   a holding member which pivotally supports the clamp, the holding member being fixed at a predetermined position of the probe.

9. The ultrasound treatment system of claim 1, wherein the ultrasound appliance further comprises:
   a suction base being formed at an end portion of the ultrasound appliance,
   wherein the suction base communicates with the second through hole of the probe.

10. The ultrasound treatment system of claim 9, further comprising:
a suction pump to suck the freed tissue through the suction base and the second through hole of the probe; and
a suction vial storing the freed tissue sucked by the suction pump.

11. The ultrasound treatment system of claim 1, wherein the ultrasound appliance further comprises a perfusion base being formed on an outer circumference of the sheath and communicating with the inner space of the sheath.

12. The ultrasound treatment system of claim 11, further comprising a roller pump jetting liquid through the perfusion base, the inner space of the sheath, and a distal opening formed by the sheath.

13. The ultrasound treatment system of claim 1, the ultrasound appliance further comprising:
an operating rod transmitting force from the manipulator to the clamp when the manipulating of the clamp is performed; and
spacers coupling the operating rod to the probe at nodes of the ultrasonic vibrations.

14. The ultrasound treatment system of claim 13, wherein the clamp includes a curved surface contacting the distal end section of the probe when the clamp is manipulated to contact the probe.

15. The ultrasound treatment system of claim 14, wherein the clamp includes wavy portions.

16. The ultrasound treatment system of claim 13, further comprising:
a first pump pumping liquid through the inner space of the sheath and to a distal opening formed by the sheath; and
a second pump pumping the freed tissue through a through hole formed in the distal end section of the probe, and forcing the freed tissue to be placed into a vial.

17. The ultrasound treatment system as in claim 4, wherein the notch is located in an outer circumference of the distal portion of the probe and is located on a side of the probe opposed to the clamp,
whereby resection can be carried out by immobilizing the living tissue using the notch.

* * * * *